(12) United States Patent
Kennedy et al.

(10) Patent No.: US 8,785,630 B2
(45) Date of Patent: Jul. 22, 2014

(54) INSECTICIDAL TRIAZINES AND PYRIMIDINES

(71) Applicant: Vestaron Corporation, Kalamazoo, MI (US)

(72) Inventors: Robert M. Kennedy, Dexter, MI (US); Bruce A. Steinbaugh, Portage, MI (US)

(73) Assignee: Vestaron Corporation, Kalamazoo, MI (US)

( * ) Notice: Subject to any disclaimer, the term of this patent is extended or adjusted under 35 U.S.C. 154(b) by 0 days.

(21) Appl. No.: 13/760,925

(22) Filed: Feb. 6, 2013

(65) Prior Publication Data

US 2013/0150365 A1    Jun. 13, 2013

Related U.S. Application Data

(62) Division of application No. 13/187,091, filed on Jul. 20, 2011, now Pat. No. 8,389,718.

(51) Int. Cl.
| | | |
|---|---|---|
| *C07D 239/48* | (2006.01) | |
| *A61K 31/505* | (2006.01) | |
| *A61K 31/506* | (2006.01) | |
| *A01N 43/54* | (2006.01) | |

(52) U.S. Cl.
USPC ........... 544/323; 544/324; 544/326; 544/328; 544/330; 544/331; 514/256; 514/275

(58) Field of Classification Search
USPC ................. 544/323, 324, 326, 328, 330, 331; 514/239, 256, 275
See application file for complete search history.

(56) References Cited

U.S. PATENT DOCUMENTS

| | | | |
|---|---|---|---|
| 3,530,121 | A | 9/1970 | Heimberger |
| 3,957,765 | A | 5/1976 | Hofer et al. |
| 4,999,275 | A | 3/1991 | Kasama et al. |
| 5,366,982 | A | 11/1994 | Dereu et al. |
| 5,492,915 | A | 2/1996 | Dereu et al. |
| 6,335,339 | B1 | 1/2002 | Arenas et al. |
| 6,384,032 | B1 | 5/2002 | Ono et al. |
| 6,451,829 | B2 | 9/2002 | Campbell et al. |
| 6,660,733 | B2 | 12/2003 | Sun et al. |
| 6,680,315 | B2 | 1/2004 | Ono et al. |
| 6,693,097 | B2 | 2/2004 | Ono et al. |
| 6,825,190 | B2 | 11/2004 | Moon et al. |
| 6,858,606 | B2 | 2/2005 | Sun et al. |
| 6,861,389 | B2 | 3/2005 | Giencke et al. |
| 6,884,758 | B2 | 4/2005 | Giencke et al. |
| 6,958,332 | B2 | 10/2005 | Sun et al. |
| 7,045,517 | B2 | 5/2006 | Ono et al. |
| 7,067,514 | B2 | 6/2006 | Ono et al. |
| 7,259,258 | B2 | 8/2007 | Kozlov et al. |
| 7,338,951 | B2 | 3/2008 | Ono et al. |
| 7,465,725 | B2 | 12/2008 | Ono et al. |
| 7,470,681 | B2 | 12/2008 | Sun et al. |
| 7,470,685 | B2 | 12/2008 | Sun et al. |
| 7,504,499 | B2 | 3/2009 | Zhao et al. |
| 7,642,220 | B2 | 1/2010 | Epp et al. |
| 7,687,498 | B2 | 3/2010 | Ono et al. |
| 7,745,436 | B2 | 6/2010 | Kostik et al. |
| 7,846,915 | B2 | 12/2010 | Wong et al. |
| 7,851,466 | B2 | 12/2010 | Wada et al. |
| 7,863,058 | B2 | 1/2011 | Zhao et al. |
| 7,872,005 | B2 | 1/2011 | Sun et al. |
| 7,919,487 | B2 | 4/2011 | Sun et al. |
| 7,923,557 | B2 | 4/2011 | Zhang et al. |
| 7,977,476 | B2 | 7/2011 | Zhao et al. |
| 8,013,154 | B2 | 9/2011 | Niyaz et al. |
| 8,058,279 | B2 | 11/2011 | Guenthenspberger et al. |
| 8,067,588 | B2 | 11/2011 | Niyaz et al. |
| 8,093,273 | B2 | 1/2012 | Wong et al. |
| 8,173,651 | B2 | 5/2012 | Ono et al. |
| 8,188,273 | B2 | 5/2012 | Niyaz et al. |
| 2002/0010343 | A1 | 1/2002 | Sircar et al. |
| 2002/0082259 | A1 | 6/2002 | Ono et al. |
| 2002/0091260 | A1 | 7/2002 | Giencke et al. |
| 2002/0115567 | A1 | 8/2002 | Giencke et al. |
| 2003/0104945 | A1 | 6/2003 | Giencke et al. |
| 2003/0114446 | A1 | 6/2003 | Sun et al. |
| 2003/0162661 | A1 | 8/2003 | Giencke et al. |
| 2003/0204083 | A1 | 10/2003 | Giencke et al. |
| 2004/0024206 | A1 | 2/2004 | Sun et al. |
| 2004/0034222 | A1 | 2/2004 | Hollander et al. |
| 2004/0167132 | A1 | 8/2004 | Shankar et al. |

(Continued)

FOREIGN PATENT DOCUMENTS

| | | |
|---|---|---|
| BE | 561091 | 10/1957 |
| CN | 101684098 A | 3/2010 |

(Continued)

OTHER PUBLICATIONS

Abdel-Fattah et al., "4-Chloro- and 4-hydrazino-pyrimidines as azolopyrimidine precursors" Journal of Chemical Research, Synopses, (1994), pp. 412-413, vol. (11).
Bohrmann et al., "Self-assembly of Beta-amyloid 42 is retarded by small molecular ligands at the stage of structural intermediates" Journal of Structural Biology (2000), 130, 232-246.
Cerny et al., "The small chemical vacuolin-1 inhibits Ca2+-dependent lysosomal exocytosis but not cell resealing" EMBO reports (2005), 6(9), 898.
Cerny et al., "The small chemical vacuolin-1 inhibits Ca2+-dependent lysosomal exocytosis but not cell resealing" EMBO reports (2004), 5(9), 883-888.
Craig et al., "Potential anticancer agents. III. 2-Phthalimido-aldehydes and derivatives" Hournal of Medicinal Chemistry, (1967), pp. 1071-1073, vol. 10(6). (No. 12).
Dayam et al., "Discovery of Small Molecule Integrin alpha-v-beta-3 Antagonissts as Novel Anticancer Agents" Journal of Medicinal Chemistry, (2006), SIR49(15), 4526-4534.

(Continued)

*Primary Examiner* — Venkataraman Balasubramanian
(74) *Attorney, Agent, or Firm* — Honigman Miller Schwartz & Cohn, LLP; Thomas A. Wootton; Jonathan P. O'Brien

(57) ABSTRACT

The present invention describes novel triazines, their related pyrimidines and their use in controlling insects. This invention also includes new synthetic procedures, intermediates for preparing the compounds, pesticide compositions containing the compounds, and methods of controlling insects using the compounds.

24 Claims, No Drawings

(56) References Cited

U.S. PATENT DOCUMENTS

| | | |
|---|---|---|
| 2004/0171489 A1 | 9/2004 | Hacker et al. |
| 2005/0101518 A1 | 5/2005 | Solow-Cordero et al. |
| 2005/0228005 A1 | 10/2005 | Moon et al. |
| 2005/0261298 A1 | 11/2005 | Solow-Cordero et al. |
| 2005/0282802 A1 | 12/2005 | Kostik et al. |
| 2006/0063739 A1 | 3/2006 | Sun et al. |
| 2006/0069090 A1 | 3/2006 | Ono et al. |
| 2006/0122156 A1* | 6/2006 | Sun et al. ............. 514/150 |
| 2007/0032493 A1 | 2/2007 | Foley et al. |
| 2007/0259962 A1 | 11/2007 | Deyn et al. |
| 2007/0293399 A1 | 12/2007 | Minn et al. |
| 2008/0058297 A1 | 3/2008 | Ono et al. |
| 2008/0119457 A1 | 5/2008 | Huang et al. |
| 2008/0167300 A1 | 7/2008 | Ono et al. |
| 2008/0176744 A1 | 7/2008 | Schwogler et al. |
| 2008/0287474 A1 | 11/2008 | Healey et al. |
| 2008/0293711 A1 | 11/2008 | Clark et al. |
| 2009/0012148 A1 | 1/2009 | Maxfield et al. |
| 2009/0042918 A1 | 2/2009 | Kearney et al. |
| 2009/0062125 A1 | 3/2009 | Epp et al. |
| 2009/0069180 A1 | 3/2009 | Rheinheimer et al. |
| 2009/0093480 A1 | 4/2009 | Guenthenspberger et al. |
| 2009/0093481 A1 | 4/2009 | Niyaz et al. |
| 2009/0093486 A1 | 4/2009 | Niyaz et al. |
| 2009/0163545 A1 | 6/2009 | Goldfarb |
| 2009/0163708 A1 | 6/2009 | Kostik et al. |
| 2009/0169558 A1 | 7/2009 | Heng et al. |
| 2009/0215765 A1 | 8/2009 | Kerrison et al. |
| 2009/0259048 A1 | 10/2009 | Wong et al. |
| 2010/0010220 A1 | 1/2010 | Zierke et al. |
| 2010/0035906 A1 | 2/2010 | Flamme et al. |
| 2010/0093803 A1 | 4/2010 | Thede et al. |
| 2010/0099774 A1 | 4/2010 | Cotter et al. |
| 2010/0120722 A1 | 5/2010 | Ono et al. |
| 2010/0121058 A1 | 5/2010 | Guenthenspberger et al. |
| 2010/0216792 A1 | 8/2010 | Gorgens et al. |
| 2010/0227860 A1 | 9/2010 | Kostik et al. |
| 2010/0267671 A1 | 10/2010 | Wu et al. |
| 2010/0292253 A1 | 11/2010 | Trullinger et al. |
| 2011/0082176 A1 | 4/2011 | Wong et al. |
| 2011/0098267 A1 | 4/2011 | Babu et al. |
| 2011/0268903 A1 | 11/2011 | Zhao et al. |
| 2011/0288081 A1 | 11/2011 | Wada et al. |
| 2011/0319515 A1 | 12/2011 | Carter et al. |
| 2011/0319615 A1 | 12/2011 | Guenthenspberger et al. |
| 2012/0021434 A1 | 1/2012 | Foley et al. |
| 2012/0040837 A1 | 2/2012 | Niyaz et al. |

FOREIGN PATENT DOCUMENTS

| | | |
|---|---|---|
| CN | 101766602 A | 7/2010 |
| CS | 86863 B | 8/1957 |
| GB | 1164594 A | 9/1969 |
| GB | 2397301 A | 7/2004 |
| JP | 51068582 A | 6/1976 |
| JP | 52083581 A | 7/1977 |
| JP | 05323515 A | 12/1993 |
| JP | 03051896 B2 | 6/2000 |
| WO | 9324468 A1 | 12/1993 |
| WO | 9936410 A1 | 7/1999 |
| WO | 9961013 A2 | 12/1999 |
| WO | 0047579 A1 | 8/2000 |
| WO | 0078757 A1 | 12/2000 |
| WO | 0127093 A1 | 4/2001 |
| WO | 03030909 A1 | 4/2003 |
| WO | 03075828 A2 | 9/2003 |
| WO | 2004024680 A1 | 3/2004 |
| WO | 2005037801 A1 | 4/2005 |
| WO | 2006021848 A1 | 3/2006 |
| WO | 2006128129 A2 | 11/2006 |
| WO | 2007008529 A2 | 1/2007 |
| WO | 2007051333 A1 | 5/2007 |
| WO | 2007071199 A1 | 6/2007 |
| WO | 2008021250 A2 | 2/2008 |
| WO | 2008074403 A2 | 6/2008 |
| WO | 2009019099 A1 | 2/2009 |
| WO | 2009020267 A1 | 2/2009 |
| WO | 2009048750 A2 | 4/2009 |
| WO | 2009048751 A1 | 4/2009 |
| WO | 2011026835 A1 | 3/2011 |
| WO | 2011032169 A2 | 3/2011 |
| WO | 2011039735 A2 | 4/2011 |
| WO | 2011044157 A1 | 4/2011 |
| WO | 2011074752 A1 | 6/2011 |
| WO | 2012008468 A1 | 1/2012 |
| WO | 2012009258 A2 | 1/2012 |

OTHER PUBLICATIONS

Desai et al., "Identification of Novel Parasitic Cysteine Protease Inhibitors Using Virtual Screening" Journal of Medicinal Chemistry, (2004), 47(27), 6609-6615.

Huang et al., "In Silico Discovery of Beta-Secretase Inhibitors" Journal of the American Chemical Society (2006), 128(16), 5436-5443.

International Search Report for Application No. PCT/US2011/044675 dated Oct. 12, 2011.

Konishi et al., "Studies on fungicidal pyrimidinylhydrazones. I. Fungicidal activity of aromatic aldehyde pyrimidinylhydrazones" Nippon Noyaku Gakkaishi, (1989), pp. 189-196, vol. 14(2).

Konishi et al., "Studies on fungicidal pyrimidinylhydrazones. III. Fungicidal activity of heteroaromatic aldehyde and ketone pyrimidinylhydrazones" Nippon Noyaku Gakkaishi, (1989), pp. 295-300, vol. 14(3).

Kremlev et al. "Phenols Reactions with 1, 1-Difluorodichloroethene, 1, 2-Di(fluorochloro)ethene, and Trifluorochloroethene." Russian Journal of Organic Chemistry, (2003), 39(8), 1125-1129.

Kuyper et al., "Pyrrolo[2, 3-d]pyrimidines and pyrido[2, 3-d]pyrimidines as conformationally restricted analogs of the antibacterial agent trimethoprim" Bioorganic & Medicinal Chemistry, (1996), pp. 593-602, vol. 4(4), Elsevier.

Maga et al., "Toward the Discovery of Novel Anti-HIV Drugs. Second-Generation Inhibitors of the Cellular ATPase DDX3 with Improved Anti-HIV Activity" ChemMedChem (2011), 6(8), 1371-1389.

Pitts et al. "Rapid Synthesis of Triazine Inhibitors of Inosine Monophosphate Dehydrogenase." Bioorganic & Medicinal Chemistry Letters, 12, (2002), p. 2.

Tobe, A., "Pharmacological studies of triazine derivatives. I.. General pharmacological actions" Yakugaku Zasshi, (1976), pp. 223-231, vol. 96(2).

Tsujikawa et al., "Studies on heterocyclic compounds. IV. Geometrical isomers of 2-(2, 6-chlorobenzylidenehydrazino)-1, 4, 5, 6-tetrahydropyrimidine hydrochloride and its related hydrazones" Yakugaku Zasshi, (1976), pp. 125-123, vol. 96(2).

Yarrow et al., "Phenotypic screening of small molecule libraries by high throughput cell imaging" Combinatorial Chemistry and High Throughput Screening (2003), 6(4), 279-286.

Zhang et al., "Pharmacore hypothesis generation of BACE-1 inhibitors and pharnacore-driven identification of potent multi-target neuroprotective agents" Medicinal Chemistry Research, (2011), Online.

* cited by examiner

INSECTICIDAL TRIAZINES AND PYRIMIDINES

CROSS-REFERENCE TO RELATED APPLICATIONS

This application is a divisional of U.S. Ser. No. 13/187,091 filed Jul. 20, 2011. This application claims priority of U.S. Provisional Application Serial No. U.S. 61/365,924, filed Jul. 20, 2010, which is incorporated herein by reference in its entirety.

BACKGROUND OF THE INVENTION

There is an acute need for new insecticides and acaricides. Insects and mites are developing resistance to known insecticides and acaricides. At least 400 species of arthropods are resistant to one or more insecticides. The development of resistance to some of the older insecticides, such as DDT, the carbamates, and the organophosphates, is well known. Resistance has even developed to some of the newer pyrethroid insecticides and acaricides. Therefore a need exists for new insecticides and acaricides, and particularly for compounds that have new or atypical modes of action.

The present invention provides novel compounds with broad-spectrum activity against insects.

SUMMARY OF THE INVENTION

The present invention describes novel triazines and their related pyrimidines and their use in controlling insects. This invention also includes new synthetic procedures, intermediates for preparing the compounds, pesticide compositions containing the compounds, and methods of controlling insects using the compounds.

This invention describes compounds useful for the control of insects. More specifically, the invention concerns compounds of the Formula I Formula I

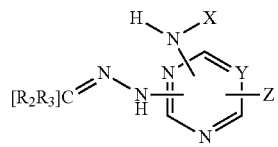

Wherein a compound of Formula I,
including its physiologically acceptable salts, compositions of matter and formulations
suitable for control of insects wherein:
Y is N or $CR_1$;
$R_1$, is —H, Halo or —$C_1$-$C_4$ alkyl;
Z is -aryl, —$C_1$-$C_8$ alkylaryl, —$C_3$-$C_8$ cycloalkyl, —$C_3$-$C_8$ cycloalkyl, heterocyclic, —$C_1$-$C_8$ alkylheterocyclic,
X, is —H, —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, —$NR^iR^j$ or —$C_1$-$C_8$ alkyl$NR^iR^j$;
$R_2$ and $R_3$ are independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkyl$NR^iR^j$, but $R_2$ and $R_3$ are not both H;
$R^i$ and $R^j$ are independently —H, or —$C_1$-$C_8$ alkyl;
wherein heterocyclic is a 5-10 member cyclic or bicyclic aromatic or saturated —$C_1$-$C_8$ cycloaliphatic ring moiety containing 1, 2, or 3 heteroatoms selected from N, O, or S;
wherein aryl, —$C_3$-$C_8$ cycloalkyl and heterocyclic are optionally independently substituted with one to five substituents independently selected from -halo, —CN, —OH, —$OCH_2CH=CHCl$, —$C_1$-$C_6$ alkyl, —O—$C_1$-$C_6$ alkyl, or —S—$C_1$-$C_6$ alkyl; and at each occurrence alkyl is optionally substituted with 1-5 halo, —CN, or —OH.

Compounds of Formula I wherein the triazine ring substituents have the positions shown in Formula XVI.

Formula XVI

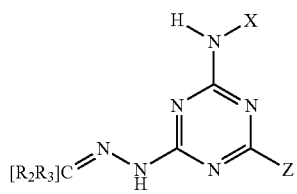

Compounds of Formula I wherein the heteroaromatic ring substituents have the positions shown in Formula II and Formula II-CR1

Formula II & II-CR1

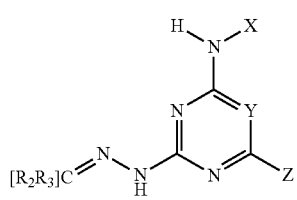

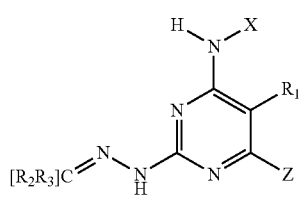

Compounds of Formula I wherein the heteroaromatic ring substituents have the positions shown in Formula III.

Formula III & III-CR₁

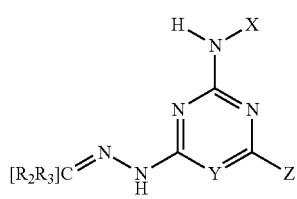

-continued

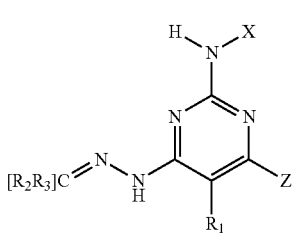

III-CR1

Compounds of Formula I wherein the heteroaromatic ring substituents have the positions shown in Formula IV.

Formula IV & IV-CR₁

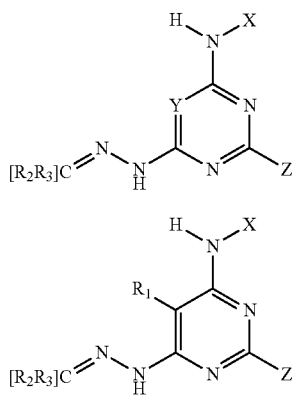

IV

IV-CR1

The compounds of Formula XVI, Formula II, Formula III, and Formula IV are preferred. The invention also provides new processes and intermediates for preparing compounds of Formula I as well as new compositions and methods of use, all described in detail herein.

DETAILED DESCRIPTION OF THE INVENTION

Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Methods of synthesis of related compounds may also be found in WO 2009/048750 A2, published on 16 Apr. 2009, Applicant Dow Agrosciences LLC US 2009-0093481 A1, incorporated by reference in its entirety and WO 2009/048751 A1, published 16 Apr. 2009, Applicant Dow Agrosciences LLC US 2009-0093480 A1, incorporated by reference in its entirety.

As described herein, compounds of the invention may optionally be substituted with one or more substituents, such as are illustrated generally above, or as exemplified by particular classes, subclasses, and species of the invention.

Throughout this document, all temperatures are given in degrees Celsius, and all percentages are weight percentages unless otherwise stated.

As used herein, the terms "heterocyclic" and "heterocycle" refer to an optionally substituted heterocycloaliphatic or an optionally substituted heteroaryl. A heterocycle can be fused to a phenyl ring to provide a bicyclic heteroaryl (e.g., indoline or indoline-yl), or a heterocycle can be fused to a heteroaryl ring to provide a bicyclic heteroaryl (e.g., 2,3-dihydro-1H-pyrrolo[2,3-b]pyridine or 2,3-dihydro-1H-pyrrolo[2,3-b]pyridine-yl).

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, or heterocycloaliphaticamino]; sulfonyl [e.g., aliphatic-S(O)₂-]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroarylalkoxy; alkoxycarbonyl; alkylcarbonyloxy; or hydroxy. Without limitation, some examples of substituted alkyls include carboxyalkyl (such as HOOC-alkyl, alkoxycarbonylalkyl, and alkylcarbonyloxyalkyl); cyanoalkyl; hydroxyalkyl; alkoxyalkyl; acylalkyl; aralkyl; (alkoxyaryl)alkyl; (sulfonylamino)alkyl (such as alkyl-S(O)₂-aminoalkyl); aminoalkyl; amidoalkyl; (cycloaliphatic)alkyl; or haloalkyl.

Unless specifically limited otherwise, the term "alkyl", as well as derivative terms such as "alkoxy" and "thioalkyl", as used herein, include within their scope, straight chain, branched chain and cyclic moieties.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, heterocycloaliphaticamino, or aliphaticsulfonylamino]; sulfonyl [e.g., alkyl-S(O)₂—, cycloaliphatic-S(O)₂—, or aryl-S(O)₂-];

sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroaralkoxy; alkoxycarbonyl; alkylcarbonyloxy; or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-S(O)$_2$-aminoalkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl; heteroaroyl; alkoxy; cycloalkyloxy; heterocycloalkyloxy; aryloxy; heteroaryloxy; aralkyloxy; nitro; carboxy; cyano; halo; hydroxy; sulfo; mercapto; sulfanyl [e.g., aliphatic-S— or cycloaliphatic-S-]; sulfinyl [e.g., aliphatic-S(O)— or cycloaliphatic-S(O)-]; sulfonyl [e.g., aliphatic-S(O)$_2$—, aliphaticamino-S(O)$_2$—, or cycloaliphatic-S(O)$_2$-]; amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl]; urea; thiourea; sulfamoyl; sulfamide; alkoxycarbonyl; alkylcarbonyloxy; cycloaliphatic; heterocycloaliphatic; aryl; heteroaryl; acyl [e.g., (cycloaliphatic)carbonyl or (heterocycloaliphatic)carbonyl]; amino [e.g., aliphaticamino]; sulfoxy; oxo; carbamoyl; (cycloaliphatic)oxy; (heterocycloaliphatic)oxy; or (heteroaryl)alkoxy.

As used herein, an "amido" encompasses both "aminocarbonyl" and "carbonylamino". These terms when used alone or in connection with another group refers to an amido group such as —N($R^i$)—C(O)—$R^j$ or —C(O)—N($R^i$)$_2$, when used terminally, and —C(O)—N($R^i$)— or —N($R^i$)—C(O)— when used internally, wherein $R^i$ and $R^j$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —N$R^i R^j$ wherein each of $R^i$ and $R^j$ is independently hydrogen, alkyl, cycloaliphatic, (cycloaliphatic)aliphatic, aryl, aralphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (aralphatic)carbonyl, (heterocycloaliphatic)carbonyl, ((heterocycloaliphatic)aliphatic)carbonyl, (heteroaryl)carbonyl, or (heteroaralphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —N$R^i$—. $R^j$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (aralphatic)oxy; (heteroaralphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl, (cycloaliphatic)carbonyl, ((cycloaliphatic)aliphatic)carbonyl, (aralphatic)carbonyl, (heterocycloaliphatic)carbonyl, ((heterocycloaliphatic)aliphatic)carbonyl, or (heteroaralphatic)carbonyl]; sulfonyl [e.g., aliphatic-S(O)$_2$— or amino-S(O)$_2$—]; sulfinyl [e.g., aliphatic-S(O)— or cycloaliphatic-S(O)-]; sulfanyl [e.g., aliphatic-S-]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl) carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "aralphatic" such as an "aralkyl" group refers to an aliphatic group (e.g., a $C_{1-4}$ alkyl group) that is substituted with an aryl group. "Aliphatic," "alkyl," and "aryl" are defined herein. An example of an aralphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl]; cycloaliphatic [e.g., cycloalkyl or cycloalkenyl]; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino]; cyano; halo; hydroxy; acyl; mercapto; alkylsulfanyl; sulfoxy; urea; thiourea; sulfamoyl; sulfamide; oxo; or carbamoyl.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2]decyl, bicyclo [2.2.2]octyl, adamantyl, azacycloalkyl, or ((aminocarbonyl) cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as aliphatic [e.g., alkyl, alkenyl, or alkynyl]; cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl]; cyano; halo; hydroxy; mercapto; sulfonyl [e.g., alkyl-S(O)$_2$— and aryl-S(O)$_2$-]; sulfinyl [e.g., alkyl-S(O)-]; sulfanyl [e.g., alkyl-S-]; sulfoxy; urea; thiourea; sulfamoyl; sulfamide; oxo; or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b] thiopheneyl, 2-oxa-bicyclo[2.2.2]octyl, 1-aza-bicyclo[2.2.2] octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety such as tetrahydroisoquinoline to produce a heteroaryl group.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S).

Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic)aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl]; nitro; cyano; halo; hydroxy; mercapto; sulfonyl [e.g., alkylsulfonyl or arylsulfonyl]; sulfinyl [e.g., alkylsulfinyl]; sulfanyl [e.g., alkylsulfanyl]; sulfoxy; urea; thiourea; sulfamoyl; sulfamide; oxo; or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b] thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., al iphatic-carbonyl; (cycloaliphatic)carbonyl; ((cycloaliphatic)aliphatic)carbonyl; (araliphatic)carbonyl; (heterocycloaliphatic) carbonyl; ((heterocycloaliphatic)aliphatic)carbonyl; or (heteroaraliphatic)carbonyl]; sulfonyl [e.g., aliphatic-S(O)$_2$— or amino-S(O)$_2$-]; sulfinyl [e.g., aliphatic-S(O)-];

sulfanyl [e.g., aliphatic-S-]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (e.g., carboxyalkyl, hydroxyalkyl, and haloalkyl such as trifluoromethyl); alkenyl; alkynyl; cycloalkyl; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; aminocarbonyl; alkylcarbonylamino; cycloalkylcarbonylamino; (cycloalkylalkyl)carbonylamino; arylcarbonylamino; aralkylcarbonylamino; (heterocycloalkyl)carbonylamino; (heterocycloalkylalkyl)carbonylamino; heteroarylcarbonylamino; heteroaralkylcarbonylamino; cyano; halo; hydroxy; acyl; mercapto; alkylsulfanyl; sulfoxy; urea; thiourea; sulfamoyl; sulfamide; oxo; or carbamoyl.

As used herein, an "acyl" group refers to a formyl group or $R^X$—C(O)— (such as -alkyl-C(O)—, also referred to as "alkylcarbonyl") where Rx and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$OR—NR$^X$—CO—O—R$^Z$ wherein R$^X$ and R$^Y$ have been defined above and R$^Z$ can be aliphatic, aryl, aralphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —S(O)$_2$—NR$^X$R$^Y$OR—NR$^X$—S(O)$_2$—R$^Z$ when used terminally; OR—S(O)$_2$—NR$^X$—OR—NR$^X$—S(O)$_2$— when used internally, wherein R$^X$, R$^Y$, and R$^Z$ are defined above.

As used herein a "sulfanyl" group refers to —S—Rx when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—Rx when used terminally and —S(O)— when used internally, wherein Rx has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—Rx when used terminally and —S(O)$_2$— when used internally, wherein Rx has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen"- or "halo" group refers to fluorine, chlorine, bromine or iodine. Many examples of the particularly useful halogens fluorine and chlorine are provided.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to five halogen atoms.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{20}$, $R_{21}$, $R_{22}$, $R_{23}$, and other variables contained therein encompass specific groups, such as alkyl and aryl. Unless otherwise noted, each of the specific groups for the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{20}$, $R_{21}$, $R_{22}$, $R_{23}$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational forms. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

"Dipolar aprotic solvents" are polar organic solvents which do not contain an exchangeable hydrogen. Among these are: tetrahydrofuran, N,N-dimethylformamide, dimethylsulfoxide and 1,4-dioxane.

Obtaining and Preparing the Starting Materials

The starting materials used to make the compounds of the Formula (I) are widely available. The compounds of Formula (I) can be synthesized according to the chemical processes outlined in Schemes A-B below.

References that may be useful in performing some of the reactions are provided here, such as cyanuric chloride by coupling with an organometallic. See, "Rapid Synthesis of Triazine Inhibitors of Inosine Monophophate Dehydrogenase" by Pitts, William J.; Guo, Junqing, Dhar, T. G. Murali; Shen, Zhongqi; Gu, Henry, H.; Watterson, Scott H.; Bednarz, Mark S.; Chen, Bang-Chi; Barrish, Joel C.; Bassoline, Donna; Cheney, Daniel; Fleener, Catherine A.; Rouleau, Katherine A.; Hollenbaugh, Diena L.; Iwanowicz, Edwin J; Biog. & Med. Chem. Letters 12 (2002) p. 2137-2140. This can be followed by the stepwise addition of nucleophiles. See, "Triazine Antiviral Compounds" Arenas, Jaime, E.; Fleming, Elizabeth, S.; International Application Publication WO 9936410, "Triazine Antiviral Compounds" Arenas, Jaime, E.; Fleming, Elizabeth, S; Xiang, Yi, B.; U.S. Pat. No. 6,335,339 B1 and "Inhibitors of IL-12 Production" Ono, Mitsunori, Wada, Yumiko, Brunkhorst, Beatrice, Warchol, Tadeusz, Wrona, Wojciech, Zhou, Dan, Vo, Nha, H. International Application Publication WO 0078757 A1. For preparation of phenoxy ethers see: "Phenols Reactions with 1,1-Difluoroethene, 1,2-Di(fluorochloro)ethane, and Trifluorochloroethene" by M. M. Kremlev; A. I. Mushta and L. I. Moklyarchuk; Russian Journal of Organic Chemistry, (2003), 39(8), 1196-1200. Methods of synthesis of related compounds may also be found in WO 2009/048750 A2, published on 16 Apr. 2009, Applicant Dow Agrosciences LLC US 2009-0093481 A1, incorporated by reference in its entirety and WO 2009/048751 A1, published 16 Apr. 2009, Applicant Dow Agrosciences LLC US 2009-0093480 A1, incorporated by reference in its entirety.

Method of Preparation

The following General Schemes with Formula are provided: General Scheme A, with Methods 1A, 1B and 1C; General Scheme B with Methods 2, 3, and 4; Example Scheme 1 for Example 1.

General Scheme A and Method 1.

General Scheme A provides several routes to make the insecticidal compounds described herein. The compounds are prepared in three steps from known compounds. Method 1 Steps 1A, 2A and 3A is the preferred route to preparation of compounds wherein Y is N.

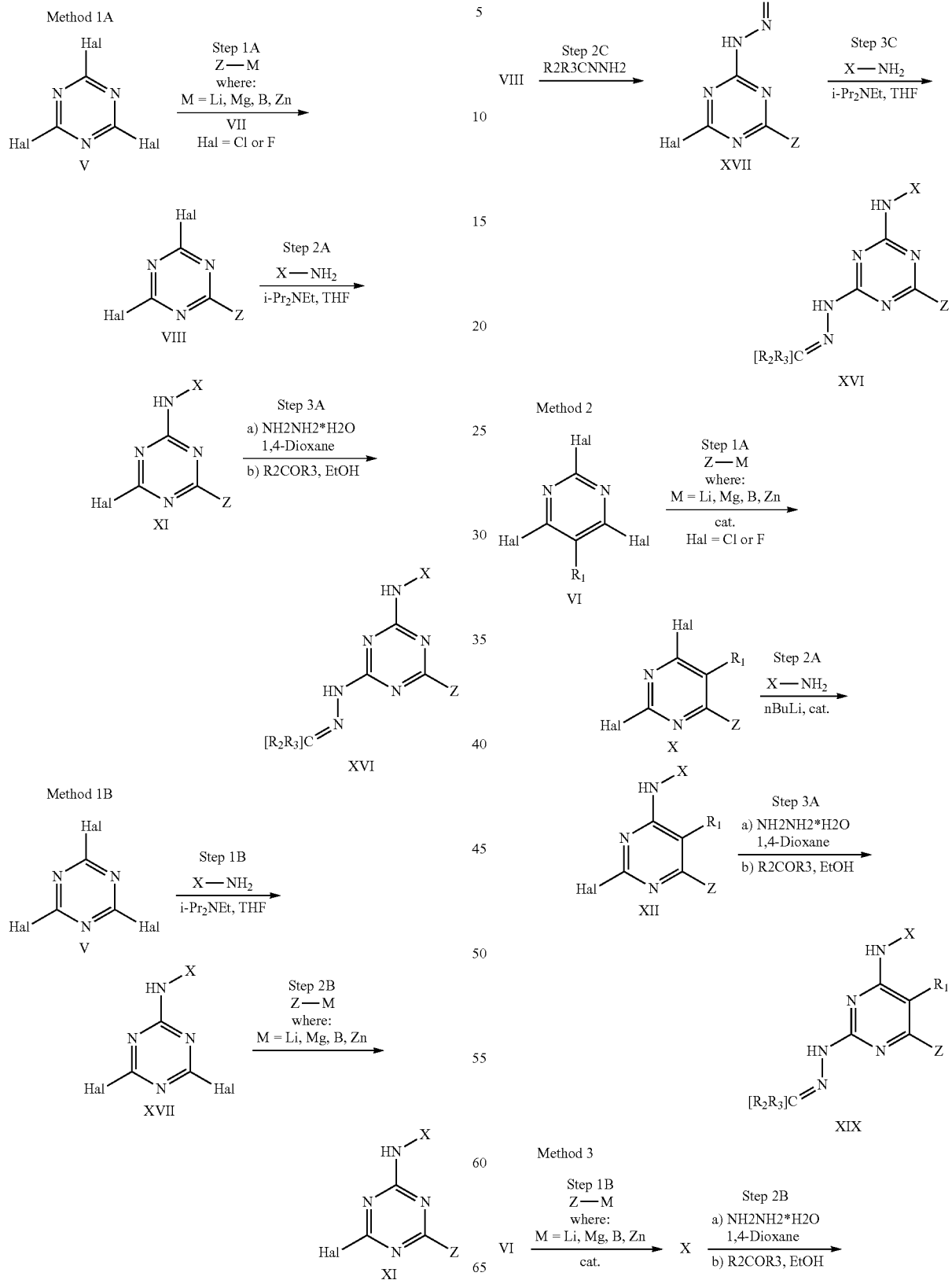

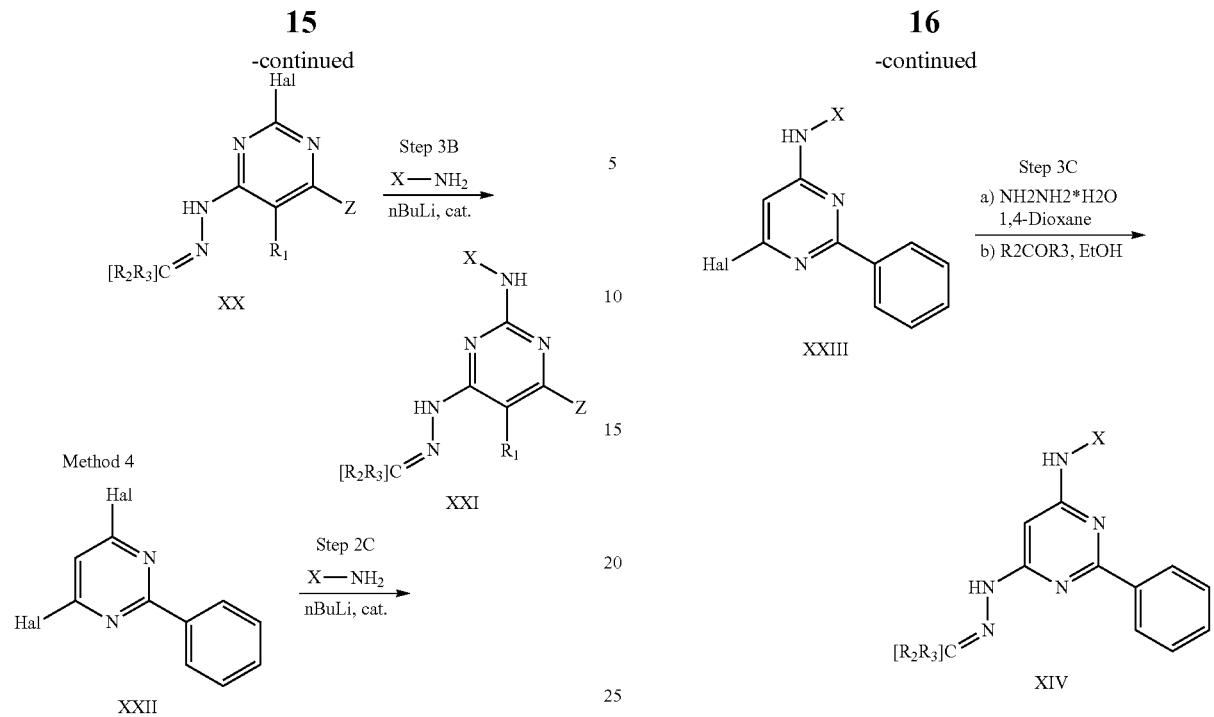
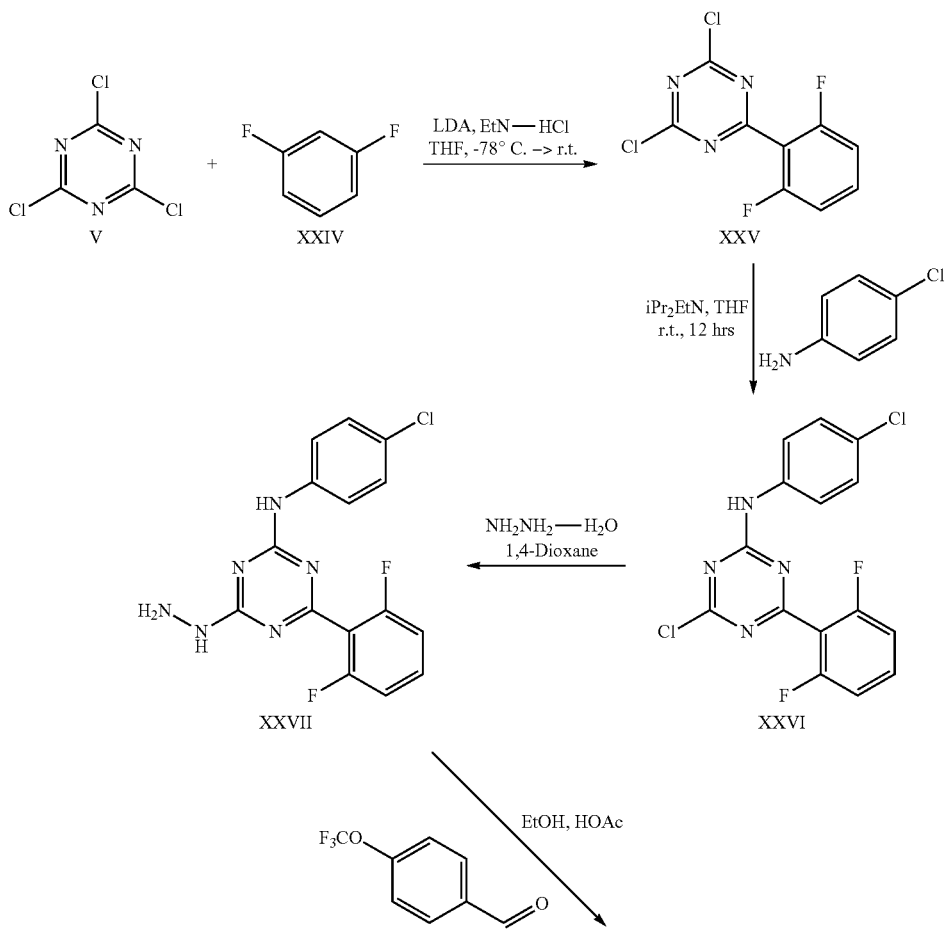
Example Scheme 1 (Example 1)

-continued

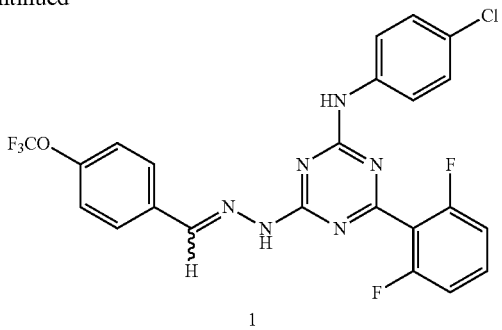

General Description for the Preparation of the Compounds, Schemes and Examples.

In General Method 1, Step 1A. The compounds of the Formula V are condensed with one equivalent of an organometallic of the Formula (VII) in a polar aprotic solvent to afford the aryl triazine derivative of the Formula (VIII). Lithium or magnesium is the preferred metal but other metals may also be used including but not limited to potassium, sodium, boron, zinc and tin. The reaction is allowed to proceed through the catalysis of palladium or other coupling catalysts known to those skilled in organic synthesis.

In General Method 1, Step 2A. The 2-aryl-4,6-dichloro-1,3,5-triazine of the Formula (VIII) is treated with a primary alkyl, aryl or heteroaryl amine in a polar aprotic solvent to afford the compound of the Formula (XI). The preferred base and solvent for the reaction of amines X—$NH_2$ are i-$Pr_2EtN$ and THF, respectively, although other bases and polar aprotic solvents can be used.

In General Method 1, Step 3A(a-b). The triazine derivative of the Formula (XI) is first treated with excess hydrazine monohydrate in 1,4-dioxane to give an intermediate hydrazine 1,3,5-triazine derivative (XVIII—structure not shown). In most cases the product is not isolated but rather collected by a simple filtration and drying.

In General Method 1, the last Step. The hydrazino 1,3,5-triazine intermediate derivative (XVIII—structure not shown) is treated with an aldehyde or ketone in ethanol or a mixture of ethanol and another solvent such as tetrahydrofuran or dichloromethane to give the arylamino-1,3,5-triazino-hydrazone of the Formula XVI. While Steps 1-3 depict a particular sequence, Steps 1 and 2 can be conducted in either order. It is, however, preferable to conduct Step 3 after Steps 1 & 2 have been completed.

The compounds of Formula (XVI) may also be made by treating the starting trihalotriazine (V) or the secondarily formed dihaloheterocycles (VIII) with the preformed hydrazone, $R_2R_3CNNH_2$ in the presence of base in an aprotic solvent such as 1,4-dioxane to form haloheterocycles as shown in Steps 2C and 3C of General Method IC. The aryl hydrazone of the Formula, $R_2R_3C$=NNH—, can be prepared from the corresponding aldehyde or ketone (*J. Org. Chem.* 1966, 31, 677). The final compounds of Formula (I) may be completed by the addition of primary amines X—$NH_2$ under the conditions described previously.

There are no regioisomeric possibilities with the triazine core products (XVI) and the above described sequence in Method 1A is preferred. It is sometimes desirable to switch the order of addition of the Z and XNH— substituents as illustrated in Steps 1B and 2B of Method 1B. The order of addition of groups to the starting trihalo compounds is strongly determinative of the relative regiopositioning of the pendant groups in pyrimidines of Formulas (I) and consequent placement into structural classes (II-IV). In order to prepare the pyrimidine regioisomers II-IV, the order of attachment of the pendant groups Z, X—$NH_2$ and the hydrazone must be changed. This is illustrated in Methods 2, 3 and 4, below.

General Method 1A Step 1A.1. Also Example 1 For this general method we also provide a specific detailed example, i.e. Example 1, which is the compound named N-(4-chlorophenyl)-4-(2,6-difluorophenyl)-6-(2-(4-(trifluoromethoxy)benzylidene)hydrazinyl)-1,3,5-triazin-2-amine (1). See also Example Scheme 1, above. A solution of lithium diisopropylamine in tetrahydrofuran (THF) (15 mL, 2M, 30 mmol) was added dropwise to a room temperature stirred suspension of triethylamine hydrochloride (0.25 g, 1.8 mmol) in dry tetrahydrofuran (THF; 10 mL). When the mixture became homogeneous, the solution was cooled to −78° C. in a dry-ice/acetone bath. Neat 1,3-difluorobenzene (3 mL, 30.4 mmol) was added dropwise and the solution stirred for 15 minutes. The −78° C. solution was poured rapidly into a −78° C. solution of cyanuric chloride (5.5 g, 30 mmol) in dry THF (25 mL). The dry-ice/acetone cold bath was removed and the mixture allowed to come to room temperature. Once at room temperature the orange-red mixture was poured into 100 mL of saturated aqueous bicarbonate solution. The mixture was allowed to stand for 15 minutes. Hexanes (100 mL) were added and after thorough mixing the organic layer was separated from the aqueous layer. The organic layer was dried over magnesium sulfate and then filtered to remove the magnesium sulfate. The solution was concentrated on a rotary evaporator to yield an oil. The oil was dissolved in a minimal amount of methylene chloride and loaded onto 100 g of silica gel. The silica gel was eluted with 10% ethyl acetate in hexanes. The organic eluent was concentrated on a rotary evaporator and the product precipitated from methylene chloride and hexane to yield 0.7 g of 2,4-dichloro-6-(2,6-difluorophenyl)-1,3,5-triazine (XXV). ESI/MS 261.9, 263.9, 265.8 (M+H).

General Method 1A Step 1A.2. A solution of n-BuLi (15 mL, 2M, 30 mmol) in cyclohexane was added dropwise to a room temperature stirred suspension of triethylamine hydrochloride (0.25 g, 1.8 mmol). When the mixture became homogeneous, the solution was cooled to −78° C. in a dry-ice/acetone bath and 20 mL of anhydrous THF was added. Neat 1,3-difluorobenzene (3 mL, 30.4 mmol) was added dropwise and the solution stirred for 15 minutes. The −78° C. solution was transferred by cannula into a −78° C. solution of cyanuric chloride (5.5 g, 30 mmol) in dry THF (25 mL). The dry-ice/acetone cold bath was removed and the mixture allowed to come to room temperature. Once at room temperature the orange-red mixture was poured into 100 mL of half saturated aqueous bicarbonate solution. The mixture was allowed to stand for 15 minutes. Hexanes (100 mL) were added and after thorough mixing the organic layer was separated from the aqueous layer. The organic layer was dried over magnesium sulfate and then filtered to remove the magnesium sulfate. The solution was concentrated on a rotary evaporator to yield an oil. The oil was dissolved in a minimal amount of methylene chloride and loaded onto 100 g of silica gel. The silica gel was eluted with 10% ethyl acetate in hexanes. The organic eluent was concentrated on a rotary evaporator and the product precipitated from methylene chloride and hexane to yield 0.7 g of 2,4-dichloro-6-(2,6-difluorophenyl)-1,3,5-triazine (XXV). ESI/MS 262.0, 263.9, 265.9 (M+H).

General Method 1A Step 1A.3. A solution of cyanuric chloride (3.69 g, 20 mmol) in dry THF (20 mL) under nitrogen was treated dropwise with a solution of 3-methoxyphenylmagnesium bromide in THF (20 mL, 1M, 20 mmol). The solution became warm and was stirred for 30 minutes at room temperature followed by stirring overnight at ~40° C. The reaction was poured into a mixture of saturated sodium bicarbonate (50 mL) and water (50 mL) forming a solid. The mixture was stirred for 20 minutes and separated layers. The aqueous layer was extracted with ethyl acetate (EtOAc) twice. The combined organic layers was dried over magnesium sulfate, filtered and concentrated on a rotary evaporator to yield a tan solid. The solid was dissolved in chloroform and loaded onto 100 g of silica gel. The silica gel was eluted with 10% ethyl acetate/hexanes followed by 20% ethyl acetate/hexanes. The appropriate fractions were concentrated on a rotary evaporator to yield 2,4-dichloro-6-(3-methoxyphenyl)-1,3,5-triazine (VIII) as a white solid (0.52 g, 4.50 g). ESI/MS 256.1, 258.1, 260.1 (M+H).

General Method 1A Step 1A.4. A solution of 1-iodo-2-fluorobenzene (2.22 g, 10 mmol) in THF (15 mL) was cooled in a dry-ice/acetone bath and then treated dropwise with a solution of nBuLi in cyclohexane (5 mL, 2M, 10 mmol) under nitrogen. The mixture was stirred cold for 30 minutes and then transferred by cannula into a solution of cyanuric chloride (1.84 g, 10 mmol) in THF (20 mL) along with a rinse with THF (5 mL). The mixture was stirred cold for 10 minutes and then allowed to warm to room temperature for 2 hours. The reaction was poured into a mixture of saturated sodium bicarbonate (25 mL) and water (25 mL) and stirred for 15 minutes. Treated with hexanes (50 mL), shaken in a separatory funnel and separated layers. The organic layer was dried over magnesium sulfate, filtered and concentrated on a rotary evaporator to yield yellow oil. The oil was diluted with a small amount of dichloromethane and loaded onto 100 g of silica gel. The silica gel was eluted with 10% ethyl acetate/hexanes. The appropriate fractions were concentrated on a rotary evaporator to yield slightly yellow oil. The oil was diluted with chloroform and loaded onto 100 g of silica gel. The silica gel was eluted with ethyl acetate/hexanes (2.5%, 5%, 7.5%). The appropriate fractions were concentrated on a rotary evaporator to yield 2,4-dichloro-6-(2-fluorophenyl)-1,3,5-triazine (VIII) as a white solid (0.842 g). ESI/MS 244.0, 246.0, 248.0 (M+H).

4-chloro-N-(4-chlorophenyl)-6-(2,6-difluorophenyl)-1,3,5-triazin-2-amine (XXVI)

General Method 1A Step 2A.1. To a solution of 262 mg (1 mmol) of (2,4-dicholoro-6-(2,6-difluorophenyl)-1,3,5-triazine (XXV) in 3 mL of dry THF was added at room temperature 129 mg (1 mmol) of iPr₂NEt (Hunig's base) in 0.5 mL of dry THF. To this was added dropwise a solution of 127 mg (1 mmol) of 4-chloroaniline in 1.5 mL of dry THF. The reaction was stirred for 12 hr at room temperature and poured into a mixture of ethyl acetate and saturated aqueous sodium bicarbonate. The layers were separated. The aqueous layer was extracted twice with additional ethyl acetate and the combined organic layers were dried over magnesium sulfate. Filtration and evaporation provided a viscous film. The material was redissolved in dichloromethane and loaded onto a small plug of silica gel in a filter funnel. The silica gel was eluted with 10% ethyl acetate in hexanes and then 20% ethyl acetate in hexanes to afford 140 mg of the desired product (XXVI). ESI/MS 353.0, 354.9, 356.9 (M+H), 351.0, 353.0, 355.0 (M−H).

General Method 1A Step 2A.2. To a solution of 2 mmol of the 2,4-dichloro-6-(2-chloro-6-fluorophenyl)-1,3,5-triazine in 10 mL of methylene chloride was added 2 mmol of the 4-chloroaniline followed by 300 mg of triethylamine. The solution spontaneously came to reflux. After coming to room temperature the material was partitioned between saturated aqueous sodium bicarbonate and ethyl acetate. The organic layers were dried over magnesium sulfate, concentrated at reduced pressure to afford material that was subjected to silica gel chromatography. After loading onto a plug of silica gel in a filter funnel, the silica gel was eluted with 10% ethyl acetate/hexanes to afford 80 mg of the desired product 4-chloro-6-(2-chloro-6-fluorophenyl)-N-(4-chlorophenyl)-1,3,5-triazin-2-amine (XI) precipitated from a mixture of ethyl acetate and hexanes. ESI/MS 369.0, 371.0, 372.9 (M+H), 367.0, 369.0, 371.0 (M−H).

General Method 1A Step 2A.3. A solution of 2-amino-5-chloropyridine (46.28 mg, 0.36 mmol) in dry THF (3 mL) was cooled in a dry-ice/acetone bath and then treated dropwise with a solution of nBuLi in cyclohexane (0.2 mL, 2M, 0.4 mmol) under nitrogen. The mixture was stirred cold for 15 minutes and then treated dropwise with a solution of 2,4-dichloro-6-(2-chloro-6-fluorophenyl)-1,3,5-triazine (VIII) (100 mg, 0.36 mmol) in dry THF (2 mL). The mixture was stirred cold for 10 minutes and then overnight at room temperature. The reaction was poured into a mixture of saturated sodium bicarbonate and ethyl acetate. After separating layers, the aqueous layer was extracted twice with ethyl acetate. The combined organics were dried over magnesium sulfate, filtered and concentrated on a rotary evaporator to yield an orange film. The orange film was dissolved in a small amount of chloroform and loaded onto a small column of silica gel. The silica gel was eluted with ethyl acetate/hexanes (10%, 20%, 30%) and the appropriate fractions were concentrated on a rotary evaporator to yield 4-chloro-6-(2-chloro-6-fluorophenyl)-N-(5-chloropyridin-2-yl)-1,3,5-triazin-2-amine (XI) as a yellow solid (19.81 mg). ESI/MS 369.9, 371.9, 373.9 (M+H), 367.9, 369.9, 372.0 (M−H).

N-(4-chlorophenyl)-4-(2,6-difluorophenyl)-6-hydrazinyl-1,3,5-triazin-2-amine (XXVII)

General Method 1A Step 3A.1 part a. To a solution of 151 mg (0.4 mmol) of triazine (XXVI) in 4 mL of 1,4-dioxane was quickly added 100 uL (2 mmol) of hydrazine monohydrate. The reaction was stirred at room temperature for 12 hours and 30 mL of water was added and the mixture stirred for an additional 30 minutes. The resultant solid was collected by filtration and washed with several portions of water. The white solid was dried overnight to afford 231 mg of N-(4-chlorophenyl)-4-(2,6-difluorophenyl)-6-hydrazinyl-1,3,5-triazin-2-amine (XXVII). If the hydrazine did not form a solid that could be filtered, then the mixture was extracted three times with ethyl acetate. The combined organics were dried over magnesium sulfate, filtered and concentrated on a rotary evaporator to yield the hydrazine intermediate.

N-(4-chlorophenyl)-4-(2,6-difluorophenyl)-6-(2-(4-(trifluoromethoxy)benzylidene)hydrazinyl)-1,3,5-triazin-2-amine (1)

General Method 1A Step 3A.1 part b. To a suspension of 1.16 g of wet hydrazine (XXVII) (1.4 mmol) in 15 mL of absolute ethanol was added 540 mg (2.84 mmol) of 4-trifluoromethoxybenzaldehyde in 3 mL of THF. Six drops of glacial acetic acid was added and the mixture was stirred for 12 hours. To the stirred mixture was added 30 mL of water and stirred an additional 30 minutes. An additional 20 mL portion of water was added and the mixture stirred for 30 minutes. The mixture was extracted with three equivolume portions of ethyl acetate. The combined organic layers were dried over magnesium sulfate, filtered and concentrated on a rotorary evaporator to yield 720 mg of a foam. The foam was redissolved in chloroform and loaded onto a plug of silica gel in a filter funnel. The silica gel was eluted with 10% ethyl acetate/hexanes followed by 30% and 50% ethyl acetate/hexanes. Fractions containing the hydrazone 1 were concentrated to yield 675 mg (1.3 mmol, 93%) of (1) as an amorphous solid. ESI/MS 520.8, 521.2, 523.0 (M+H), 519.2 (M−H).

General Method 1A Step 3A.2. To a solution of 0.14 mmol of 4-chloro-6-(2-chloro-6-fluorophenyl)-N-(4-chlorophenyl)-1,3,5-triazin-2-amine in 1 mL of methylene chloride was added 0.27 mmol of the preformed hydrazone, (4-(trifluoromethoxy)benzylidene)hydrazine. The mixture was stirred overnight and chromatographed on silica gel to afford the final triazine hydrazone. See Example 4. 4-(2-chloro-6-fluorophenyl)-N-(4-chlorophenyl)-6-(2-(4-(trifluoromethoxy)benzylidene)hydrazinyl 1,3,5-triazine-2-amine. ESI/MS 537.1, 539.0, 541.0 (M+H), 535.1, 537.0 (M−H).

The preformed hydrazone, (4-(trifluoromethoxy)benzylidene)hydrazine, above was prepared according to the following: A solution of hydrazine monohydrate (17.0 mL, 350.5 mmol) in ethanol (20 mL) was treated dropwise with 4-trifluoromethoxybenzaldehyde (5.0 mL, 35 mmol). Treated with absolute ethanol (4 mL) and stirred at room temperature for 2 hours. The reaction was concentrated on a rotary evaporator. The residue was taken up in diethyl ether and washed with water. The aqueous layer was extracted 3 times with diethyl ether. The combined organic layers was dried over magnesium sulfate, filtered and concentrated on a rotary evaporator to yield (4-(trifluoromethoxy)benzylidene)hydrazine as a liquid (7.04 g). ESI/MS 205.2 (M+H).

General Method IC Step 2C. A solution of 2,4-dichloro-6-(2-chloro-6-fluorophenyl)-1,3,5-triazine (VIII) (1.5 g, 5.39 mmol) in 1,4-dioxane (30 mL) was treated with a solution of iPr$_2$NEt (1.04 g, 8.08 mmol) in 1,4-dioxane (5 mL). The mixture was treated with (4-(trifluoromethoxy)benzylidene)hydrazine (1.1 g, 5.39 mmol) in 1,4-dioxane (15 mL). The reaction was stirred overnight at room temperature. The reaction was concentrated on a rotary evaporator to yield a thick oil which was taken up in diethyl ether and washed with brine. The organic layer was dried over magnesium sulfate, filtered and concentrated on a rotary evaporator to yield a foam. The foam was dissolved in a small amount of chloroform and loaded onto 100 g of silica gel. The silica gel was eluted with ethyl acetate/hexanes (10%, 20%, 30%, 50%). The appropriate fractions were concentrated on a rotary evaporator to yield 2-chloro-4-(2-chloro-6-fluorophenyl)-6-(2-(4-(trifluoromethoxy)benzylidene)hydrazinyl)-1,3,5-triazine (XVII) as a foam/film (2.347 g). ESI/MS 446.1, 448.1, 450.1 (M+H), 444.2, 446.2 (M−H).

General Method 1C Step 3C. A solution of 2-chloro-4-(2-chloro-6-fluorophenyl)-6-(2-(4-(trifluoromethoxy)benzylidene)hydrazinyl)-1,3,5-triazine (XVII) (250 mg, 0.56 mmol) in 1,4-dioxane (2 mL) was treated with a solution of iPr$_2$NEt (144.8 mg, 1.12 mmol) in 1,4-dioxane (1 mL). The mixture was treated with a solution of 5-aminomethyl-2-chloropyridine (80.37 mg, 0.564 mmol) in 1,4-dioxane (1 mL). The reaction was stirred overnight at room temperature. The reaction was concentrated on a rotary evaporator and the residue was taken up in ethyl acetate and washed with brine. The aqueous layer was extracted twice with ethyl acetate. The combined organics was dried over magnesium sulfate, filtered and concentrated on a rotary evaporator to yield a white solid. The solid was taken up in chloroform and loaded onto 100 g of silica gel. The silica gel was eluted with ethyl acetate/hexanes (30%, 40%, 50%, 70%). The appropriate fractions were concentrated on a rotary evaporator to yield 4-(2-chloro-6-fluorophenyl)-N-((6-chloropyridin-3-yl)methyl)-6-(2-(4-(trifluoromethoxy)benzylidene)hydrazinyl)-1,3,5-triazin-2-amine (Example 22) as a white solid (305 mg). ESI/MS 552.3, 554.2 (M+H), 550.4, 552.4 (M−H).

General Method 2 Step 1A.2. To a −78° C. solution of 5 mmol of 1-chloro-3-fluorobenzene in 10 mL of dry THF was added 5 mmol (2 mL, 2.5M) nBuLi. After 15 min added 2 mL dry THF solution of 5 mmol of 2,4-dichloropyrimidine. The solution was allowed to come to room temperature. The starting material had disappeared by TLC analysis. The reaction mixture was poured into a biphasic mixture of 0.1% acetic acid in water and ethyl acetate. The organic layer was separated and cooled in an ice bath. To the cooled ethyl acetate solution was added 5 mmol of DDQ and stirred for 15 min. A new product emerged was visible by TLC analysis (5% ethyl acetate/hexanes). The reaction was diluted with an equal portion of hexanes and filtered through silica gel. The resultant eluent was concentrated under reduced pressure and subjected to chromatography on silica gel with 5% ethyl acetate/hexanes to afford 280 mg of 2,4-dichloro-6-(2-chloro-6-fluorophenyl)pyrimidine (X) as a white solid. ESI/MS 276.9901 (M+H).

General Method 2 Step 1A.3 A mixture of 2,4,6-trichloropyrimidine (1.834 g, 10 mmol) and bis(triphenylphosphine)palladium(II) dichloride (60 mg, 0.085 mmol) in dry THF (20 mL) under nitrogen was treated dropwise with a solution of PhMgBr in THF (11 mL, 1M, 11 mmol) which generated some heat. The mixture was stirred for 1 hour and then partitioned between saturated sodium bicarbonate and ethyl acetate. Separated layers and the aqueous layer was extracted twice with ethyl acetate. The combined organics was dried over magnesium sulfate, filtered and concentrated on a rotary evaporator to yield a film (2.32 g). The film was taken up in chloroform and loaded onto 100 g of silica gel. The silica gel was eluted with ethyl acetate/hexanes (2%, 2.5%, 3%, 5%). The appropriate fractions were concentrated on a rotary evaporator to yield a white solid. The solid was triturated with hexanes, filtered and washed with more hexanes to yield 2,4-dichloro-6-phenylpyrimidine (X) as a white solid (382.97 mg). ESI/MS 225.0, 227.0, 229.0 (M+H).

General Method 2 Step 2A.1. Cooled a solution of 5-amino-2-chloropyridine (218.55 mg, 1.7 mmol) in dry THF (4.3 mL) in a dry-ice/acetone bath under nitrogen. The mixture was treated with a solution of nBuLi in hexanes (0.68 mL, 2.5M, 1.7 mmol) dropwise and stirred cold for 10 minutes. Allowed to warm to room temperature and ~1.7 mL of the mixture was added dropwise to a solution of 2,4-dichloro-6-phenylpyrimidine (X) (190 mg, 0.844 mmol) in dry THF (2 mL). The mixture was stirred for 15 minutes and treated with an additional ~0.3 mL of the lithium anilide solution and stirred for another 15 minutes. The reaction was poured into a mixture of saturated sodium bicarbonate and ethyl acetate. The layers were separated and the aqueous layer was extracted twice with ethyl acetate. The combined organics was dried over magnesium sulfate, filtered and concentrated to yield a film. The film was taken up in chloroform and loaded onto 100 g of silica gel. The silica gel was eluted with ethyl acetate/hexanes (10%, 20%, 30%, 40%). The appropriate fractions were concentrated on a rotary evapororator to yield 2-chloro-N-(6-chloropyridin-3-yl)-6-phenylpyrimidin-4-amine (XII) as a film (41.15 mg). ESI/MS 317.0756, 319.0810 (M+H).

General Method 2 Step 2A.2. To 1 mmol of 2,4-dichloro-6-phenylpyrimidine (X) and 4-chloroaniline in 4 mL of dry THF was added 1 mmol (0.5 mL, 2M in THF/heptane/ethylbenzene) of lithium diisopropylamide. The reaction was followed by TLC (30% ethyl acetate/hexane). The reaction mixture was partitioned between ethyl acetate and saturated aqueous sodium bicarbonate and the organic layers were dried over magnesium sulfate and concentrated under reduced pressure. The mixture was purified by chromatography on silica gel with elution by 30% ethyl acetate/hexanes to afford 70 mg of 2-chloro-N-(4-chlorophenyl)-6-phenylpyrimidin-4-amine (XII) as an amorphous solid. ESI/MS 315.883, 317.915 (M+H).

General Method 2 Step 3A. A solution of 2-chloro-N-(6-chloropyridin-3-yl)-6-phenylpyrimidin-4-amine (XII)(41 mg, 0.13 mmol) in 1,4-dioxane (2 mL), was treated with hydrazine monohydrate (50 uL, 1.03 mmol) and stirred at room temperature for 30 minutes. The reaction was treated with additional hydrazine monohydrate (50 uL, 1.03 mmol) and stirred at ~40° C. for 30 minutes and then at ~50° C. for 2 hours. The reaction was treated with water (10 mL) and extracted 3 times with ethyl acetate. The combined organics was dried over magnesium sulfate, filtered and concentrated on a rotary evaporator to yield a solid (26.7 mg). The solid (26.7 mg, 0.085 mmol) was treated with absolute ethanol (1.5 mL) and then a solution of 4-trifluoromethoxybenzaldehyde (40 mg, 0.21 mmol) in absolute ethanol (1.5 mL). The reaction was treated with 2 drops of acetic acid and stirred overnight at room temperature. The reaction was treated with water (10 mL) and stirred for 30 minutes. The mixture was extracted 3 times with ethyl acetate. The combined organics was dried over magnesium sulfate, filtered and concentrated on a rotary evaporator to yield a film. The film was taken up in chloroform and loaded onto a small column of silica gel. The silica gel was eluted with ethyl acetate (10%, 30%, 50%). The appropriate fractions were concentrated on a rotary evaporator to yield N-(6-chloropyridin-3-yl)-6-phenyl-2-(2-(4-(trifluoromethoxy)benzylidene)hydrazinyl)pyrimidin-4-amine (Example 47) as an off-white solid (34.87 mg). ESI/MS 485.2, 487.2 (M+H), 483.0, 485.0 (M–H).

General Method 3 Step 2B. To a solution of 2,4-dichloro-6-phenylpyrimidine (224 mg, 1 mmol) in 1 mL of 1,4-dioxane was added 300 uL of hydrazine hydrate. Stirring was continued at room temperature and the reaction monitored by thin layer chromatography (30% ethyl acetate/hexanes). When the starting material was consumed, 2 mL of water was added and the resultant precipitate was collected on a filter to afford 2-chloro-4-hydrazinyl-6-phenylpyrimidine as a yellow solid. The damp solid was suspended in 2 mL of ethanol, to which was added 220 mg of 4-trifluoromethoxybenzaldehyde. Within 5 minutes the solution became clear and then reprecipitated material. The product, 2-chloro-4-phenyl-6-(2-(4-(trifluoromethoxy)benzylidene)hydrazinyl)pyrimidine (XX), was collected by filtration and dried to afford 150 mg of a solid. ESI/MS 392.973, 395.002 (M+H).

General Method 3 Step 2C. To a –78° C. THF solution of 4-chloroaniline was added 1 equivalent of nBuLi to prepare the lithium anilide. The solution was allowed to come to room temperature under nitrogen atmosphere. Aliquots of the lithium anilide were added portion wise to a THF solution of 2-chloro-4-phenyl-6-(2-(4-(trifluoromethoxy)benzylidene) hydrazinyl)pyrimidine (XX) containing 0.05 equivalents (relative to (XX)) of Bis(triphenylphosphine) palladium(II) dichloride. The reaction was followed by thin layer chromatography. When the starting material XX was consumed the reaction was poured into a saturated aqueous solution of sodium bicarbonate and extracted with ethyl acetate. The organic layers were dried over magnesium sulfate, filtered and concentrated at reduced pressure. The product, N-(4-chlorophenyl)-4-phenyl-6-(2-(4-(trifluoromethoxy)benzylidene)hydrazinyl)pyrimidin-2-amine (Example 58) was obtained as a solid. ESI/MS 483.9728, 485.9988 (M+H).

General Method 4 Step 2C. A solution of 4-chloroaniline (127.6 mg, 1 mmol) in dry THF (2 mL) was cooled in a dry-ice/acetone bath and treated dropwise with a solution of nBuLi in cyclohexane (0.5 mL, 2M, 1 mmol). The mixture was treated with additional dry THF (2 mL) and was allowed to warm slightly (~15 minutes) till the material went into solution. The material was then transferred by cannula into a solution of fenclorim (XXII) (225 mg, 1 mmol) and bis(triphenylphosphine)palladium(II) dichloride (35 mg, 0.05 mmol) in dry THF (2 mL). Rinsed with dry THF (2 mL) and stirred at room temperature for 30 minutes. The reaction was partitioned between saturated sodium bicarbonate and ethyl acetate. Added brine to help clear an emulsion. Separated layers and the aqueous layer was extracted twice with ethyl acetate. The combined organics was dried over magnesium sulfate, filtered and concentrated on a rotary evaporator to yield a film. The film was taken up in chloroform and loaded onto 100 g of silica gel. The silica gel was eluted with 10% ethyl acetate/hexanes followed by 20% ethyl acetate/hexanes. The appropriate fractions were concentrated to yield 6-chloro-N-(4-chlorophenyl)-2-phenylpyrimidin-4-amine (XXIII) as a film (161.87 mg). ESI/MS 315.9, 317.9 (M+H), 314.0, 316.0 (M–H).

General Method 4 Step 3C. A solution of 6-chloro-N-(4-chlorophenyl)-2-phenylpyrimidin-4-amine (XXIII) (161.87 mg, 0.51 mmol) in 1,4-dioxane (5 mL) was treated with hydrazine monohydrate (120 uL, 2.47 mmol) and stirred at room temperature for 1 hour. The reaction was then stirred at 40° C. for 135 minutes and treated with additional hydrazine monohydrate (300 uL, 6.18 mmol). Stirred with heat for 30 minutes and treated with additional hydrazine monohydrate (700 uL, 14.43 mmol). Stirred with heat for 30 minutes and treated with additional hydrazine monohydrate (1.5 mL, 30.9 mmol) and stirred for 15 minutes. Treated with hydrazine monohydrate (500 uL, 10.3 mmol, new bottle) and stirred overnight at ~50° C. The reaction was cooled and partitioned between water and dichloromethane. The organic layer was concentrated on a rotary evaporator to yield a film (229.26 mg). The film (assumed 0.51 mmol) was treated with absolute ethanol (5 mL). The mixture was treated with a solution of with 4-trifluoromethoxybenzaldehyde (194.7 mg, 1.02 mmol) in absolute ethanol (3 mL). The mixture was treated with 3 drops of acetic acid and stirred at room temperature for 3 hours. The reaction was treated with water (35 mL) and stirred for 30 minutes. The aqueous solution was extracted 3 times with ethyl acetate. The combined organics was dried over magnesium sulfate, filtered and concentrated to yield a film. The film was taken up in chloroform and loaded onto 100 g of silica gel. The silica gel was eluted with ethyl acetate/hexanes (10%, 15%, 20%, 30%). The appropriate fractions were concentrated to yield N-(4-chlorophenyl)-2-phenyl-6-(2-(4-(trifluoromethoxy)benzylidene)hydrazinyl)pyrimidin-4-amine (Example 46) as a film (233.6 mg). ESI/MS 483.6, 485.9 (M+H), 482.0, 484.0 (M−H).

This invention comprises all of the compounds, procedures and uses for these compounds which are described herein. The compounds of this invention may be described in general or generic terms or varying specificity as well as with specific examples. Terms and expressions are described with particularity below in various combinations and with various descriptive Formula. A description of the invention follows:

A compound of Formula I,

Formula I

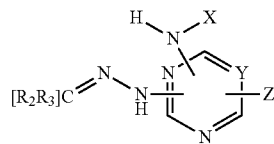

including its physiologically acceptable salt wherein:
Y is N or $CR_1$; $R_1$, is —H, halo or —$C_1$-$C_4$ alkyl; Z is -aryl, —$C_1$-$C_8$ alkylaryl, —$C_3$-$C_8$ cycloalkyl, —$C_1$-$C_6$ alkyl$C_6$cycloalkyl, heterocyclic, —$C_1$-$C_8$ alkylheterocyclic, X, is —H, —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, —$NR^iR^j$ or —$C_1$-$C_8$ alkyl$NR^iR^j$; $R^i$ and $R^j$ are independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkyl$NR^iR^j$, but $R_2$ and $R_3$ are not both H; $R^i$ and $R^j$ are independently —H, or —$C_1$-$C_8$ alkyl; wherein heterocyclic is a 5-10 member cyclic or bicyclic aromatic or saturated —$C_1$-$C_8$ cycloaliphatic ring moiety containing 1, 2, or 3 heteroatoms selected from N, O, or S; wherein aryl, —$C_3$-$C_8$ cycloalkyl and heterocyclic are optionally independently substituted with one to five substituents independently selected from -halo, —CN, —OH, —$OCH_2CH=CHCl$, —$C_1$-$C_6$ alkyl, —O—$C_1$-$C_6$ alkyl, or —S—$C_1$-$C_6$ alkyl; and at each occurrence alkyl is optionally substituted with 1-5 halo, —CN, or —OH.

The six member ring system shown in Formula I and various other formula herein is called the "core moiety." The core moiety has two forms, a ring with 3 Nitrogen (N) atoms and 3 Carbon (C) atoms or a ring with 2 Nitrogen (N) atoms and 4 Carbon (C) atoms. The first form herein is called a triazine and the latter form a pyrimidine ring. These descriptions are not limited to positional isomers although for clarity and specificity those are also described. Referring to Formula I, the triazines have Y is N, and the pyrimidines have Y is $CR_1$ thus two different groups of compounds are described. Much of the description herein refers to the triazines, and there are many examples of triazines which are provided with data. It should be noted however that pyrimidines are also fully described, made and claimed and many examples of these are also provided with data. It should and will be understood by one of skill in the art that the substituents and substitutions described herein for the triazines can just as easily be applied and should just as easily be applied to pyrimidines.

The core moiety generally has three different points of attachment for four other major moieties, which can attach to the core in three general locus. These four moieties are referred to herein as Z, X, $R_2$ and $R_3$. While the points of attachment to the core and specificity of the groups is provided in various examples mostly with the triazines and mostly with aromatic compounds, it should be understood and appreciated that also described, and with just as much particularity and emphasis are the pyrimidines, any many examples of pyrimidines are also provided. Also described are the related but different saturated aliphatic ring systems and compounds, examples of which are also provided.

A compound of Formula I, wherein Y is $CR_1$, herein pyrimidines is shown. $R_1$ may be H, halogen, —$C_1$-$C_4$ alkyl optionally substituted with 1-5 halo, —CN, or —OH. $R_1$, as H, methyl or —$CF_3$ is preferred. Aliphatic saturated and unsaturated compounds, like the aryl of Formula I are described with particularity. For example, we describe compounds of Formula I wherein Y is N. A triazine with various substituents on 1, 2 or 3 C atoms is described, such as where the attached moieties are $R_1$, is —H, Halo or —$C_1$-$C_4$ alkyl; Z is -aryl, —$C_1$-$C_8$ alkylaryl, —$C_3$-$C_8$ cycloalkyl, —$C_1$-$C_6$ alkyl$C_6$cycloalkyl, heterocyclic, —$C_1$-$C_8$ alkylheterocyclic, X, is —H, —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, —$NR^iR^j$ or —$C_1$-$C_8$ alkyl$NR^iR^j$; $R_2$ and $R_3$ are independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ but $R_2$ and $R_3$ are not both H; $R^i$ and $R^j$ are independently —H, or —$C_1$-$C_8$ alkyl;
wherein heterocyclic is a 5-10 member cyclic aromatic or saturated —$C_1$-$C_8$ cycloaliphatic ring moiety containing 1, 2, or 3 heteroatoms selected from N, O, or S;
wherein aryl, —$C_3$-$C_8$ cycloalkyl and heterocyclic are optionally independently substituted with one to five substituents independently selected from -halo, —CN, —OH, —$OCH_2CH=CHCl$, —$C_1$-$C_6$ alkyl, —O—$C_1$-$C_6$ alkyl, or —S—$C_1$-$C_6$ alkyl; and at each occurrence alkyl is optionally substituted with 1-5 halo, —CN, or —OH.

In the description and in the claims chemical groups whether listed independently or as a definition for a variable may replace or depend on one another in any combination, such that generic groups of decreasing size and fewer optional substitutions are described.

An attached heterocyclic may be comprised of a 5, 6 or 10 member ring where the heteroatoms are selected from N, O or S. When the term "aryl" is used it is defined as above and a specific example includes aryls having an optionally substituted 6 or 10 member ring. The halo or halogen as mentioned may be fluorine or fluoride (F), chlorine or chloride (Cl), iodine or iodide (I), or bromine or bromide (Br) or various forms of each thereof, but most frequently F and Cl are used in the examples. Alkyls and alkoxys substituted with F and Cl, such as —$CCl_3$ and —$CF_3$, —$CH_{1-2}F_{1-2}$, —$CH_{1-2}Cl_{1-2}$, —CHClF, —$CH_2$—$CCl_3$, —$CH_2$—$CF_3$, —CHCl—$CF_3$, —CHF—$CF_3$, —CHCl—$CF_3$, CHF—$CF_3$, —CHF—$CF_3$, —CHCl—$CHF_2$, —CHF—$CHF_2$, —CHCl—$CHCl_2$, —CHF—$CHCl_2$, including —CHF—$CH_{1-2}F_{1-2}$, —CHCl—$CH_{1-2}F_{1-2}$, —CHF—$CH_{1-2}Cl_{1-2}$, —CHCl—$CH_{1-2}Cl_{1-2}$, —CHCl—$CH_{1-2}F_{1-2}$, —CHF—CHFCl, and alkoxy versions, i.e. —O—$CCl_3$, —O—$CF_3$, —O—$CH_{1-2}F_{1-2}$, —O—$CH_{1-2}Cl_{1-2}$, —O—CHClF, —O—$CH_2Cl$, —O—$CH_2F$, —O—$CCl_3$, —O—$CH_2$—$CF_3$, —O—CHCl—$CF_3$, —O—CHF—$CF_3$, —O—CHCl—$CCl_3$, —O—CHF—$Cl_3$, —O—CHCl—$CHF_2$, —O—CHF—$CHF_2$, preferred are —O—$CF_2$—$CHF_2$, and O—$CF_2$—CHFCl, and related alkoxys such as —O—CHCl—$CHCl_2$, —O—CHF—$CHCl_2$, —O—CHF—$CH_{1-2}F_{1-2}$, —O—CHCl—$CH_{1-2}F_{1-2}$, —O—CHF—$CH_{1-2}Cl_{1-2}$, —O—CHCl—$CH_{1-2}F_{1-2}$, —O—CHCl—$CH_{1-2}Cl_{1-2}$, —O—CHCl—O—$CH_{1-2}F_{1-2}$, —O—$CH_{1-2}F_{1-2}$, —CHFCl, i.e. —$C_1$-$C_8$ alkyl and —O— —$C_1$-$C_8$ alkyl and all halo substitutions. Including —$C_{0-8}F_{1-5}$ and —$C_{0-8}Cl_{1-5}$ and all combinations thereof of F, Cl, Br, and I. Aryls, such as phenyl and napthyl both unsubstituted and substituted with halo, especially with F and Cl are well described. Both aromatic or unsaturated rings like aryls and aliphatic or saturated rings like cycloalkyls may have these substituents. An example is a saturated ring systems such as $C_6$ cycloalkyl, with or without a halo.

Compounds wherein $R^i$ and $R^j$ are independently —H, or —$C_1$-$C_8$ alkyl are described in any combination and with any other compounds. Compounds wherein $R^i$ and $R^j$ are independently —H, or $C_1$-$C_2$ alkyl are preferred. $R^i$ and $R^j$ are independently, H or $C_1$-$C_4$ alkyl, H or $C_1$-$C_6$ alkyl, H or $C_1$-$C_8$ alkyl.

For compounds throughout the application each occurrence of "alkyl" when specified may be straight or branched $C_1$-$C_2$ alkyl, $C_1$-$C_4$ alkyl, $C_1$-$C_6$ alkyl, $C_1$-$C_8$ alkyl, $C_1$-$C_{10}$ alkyl, or $C_1$-$C_{12}$ alkyl. Similarly the following terms may be used herein in any combination and in any place the terms cycloalkyl or aryl are used, they may be specified that each occurrence of cycloalkyl may be specified as —$C_3$-$C_{12}$ cycloalkyl, —$C_3$-$C_{11}$ cycloalkyl, —$C_3$-$C_{10}$ cycloalkyl, —$C_3$-$C_9$ cycloalkyl, —$C_3$-$C_8$ cycloalkyl, —$C_3$-$C_7$ cycloalkyl, —$C_3$-$C_6$ cycloalkyl, $C_3$-$C_5$ cycloalkyl, —$C_3$-$C_4$ cycloalkyl, —$C_5$-$C_9$ cycloalkyl, —$C_5$-$C_8$ cycloalkyl, $C_5$-$C_7$ cycloalkyl, $C_5$-$C_6$ cycloalkyl, $C_6$-$C_8$ cycloalkyl, $C_8$-$C_{12}$ cycloalkyl, —$C_3$ cycloalkyl, —$C_4$ cycloalkyl, —$C_5$ cycloalkyl, —$C_6$ cycloalkyl, —$C_7$ cycloalkyl, —$C_8$ cycloalkyl, —$C_9$ cycloalkyl, —$C_{10}$ cycloalkyl, —$C_{11}$ cycloalkyl, and —$C_{12}$ cycloalkyl, and each occurrence of cycloalkyl or aryl may be —$C_3$-$C_{12}$ cycloalkyl or —$C_3$-$C_{12}$ aryl, —$C_3$-$C_{10}$ cycloalkyl or —$C_3$-$C_{10}$ aryl, —$C_3$-$C_8$ cycloalkyl or —$C_3$-$C_8$ aryl, —$C_3$-$C_6$ cycloalkyl, —$C_5$-$C_{12}$ cycloalkyl, —$C_5$-$C_{10}$ cycloalkyl or —$C_5$-$C_{10}$ aryl, —$C_5$-$C_8$ cycloalkyl, —$C_5$-$C_6$ cycloalkyl, $C_3$-$C_5$ cycloalkyl, —$C_3$ cycloalkyl, —$C_5$ cycloalkyl, —$C_6$ cycloalkyl, —$C_7$ cycloalkyl, —$C_8$ cycloalkyl, —$C_9$ cycloalkyl, —$C_{10}$ cycloalkyl, —$C_{1-2}$ cycloalkyl, —$C_6$ aryl, $C_{10}$ aryl.

The variables $R_2$ and $R_3$ are independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkylNR$^i$R$^j$, and in some embodiments and groups of claims it should be noted that $R_2$ and $R_3$ are not both H; Compounds are described wherein when $R_2$ is —H or —$C_1$-$C_8$ alkyl, then $R_3$ is —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkylNR$^i$R$^j$; and compounds are described wherein when $R_3$ is —H or —$C_1$-$C_8$ alkyl, then $R_2$ is —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, -heterocyclic, —$C_1$-$C_8$ alkylheterocyclic, and —$C_1$-$C_8$ alkylNR$^i$R$^j$. It should also be understood that with some embodiments of the invention $R_2$ and $R_3$ can be independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkylNR$^i$R$^j$; but when one of $R_2$ and $R_3$ are -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkylNR$^i$R$^j$ then the other of either $R_2$ or $R_3$ is independently —H or —$C_1$-$C_8$ alkyl.

The terms "heterocyclic" or "alkylheterocyclic" refers to an aromatic and unsaturated optionally substituted ring in addition to referring to a non-aromatic and saturated optionally substituted ring where the heteroatom may be N, O, S or any combination of these atoms but the more preferred heteroatoms are N and O, nonadjacent heteroatoms are preferred. Substituents of the core moiety having a morpholino group attached, substituted or unsubstituted are preferred. Aromatic heterocyclic substituents are favored and many examples of heteroatoms, particularly X substituents are described that have one N ring atom in a 6 member aromatic ring. A core moiety substituent may have two or three heteroatoms, with a heterocyclic and for example two non-adjacent atoms like N and N or N and O are described.

We describe with particularity compounds where the core moiety, triazines, pyrimidines or both, have aliphatic or aromatic aryl attachments and that do not contain "heterocyclic" or "alkylheterocyclic" groups, such as, for example, where Z is -aryl, —$C_1$-$C_8$ alkylaryl, —$C_3$-$C_8$ cycloalkyl, or —$C_1$-$C_6$ alkyl$C_6$cycloalkyl. X is —H, —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, —NR$^i$R$^j$ or —$C_1$-$C_8$ alkylNR$^i$R$^j$; when $R_2$ is —H or —$C_1$-$C_8$ alkyl then $R_3$ is —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, and —$C_1$-$C_8$ alkylNR$^i$R$^j$; and when $R_3$ is —H or —$C_1$-$C_8$ alkyl then $R_2$ is —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, and —$C_1$-$C_8$ alkylNR$^i$R$^j$; R$^i$ and R$^j$ are independently —H, or —$C_1$-$C_8$ alkyl; The following examples are of this type, 1-7, 10-11, 14, 17-21, 23, 27-35, 37-39, 41, 43-44, 46, 48, 52, 57-58, and 60-61. Pyrimidine examples are 46, 52, 57, 58 and 61.

In these examples and descriptions the variables Z, X, and $R_3$ and $R_2$ may be as described and considered to be a pendant moiety. In some embodiments, particularly of the type just described above, there can optionally be 1, 2, or 3 substituents to the core moiety, triazines, pyrimidines or both, and the substitutents, Z, X, $R_3$ and $R_2$ may be as described above only where each instance of aryl is phenyl and the phenyl is optionally independently substituted with 1, 2 or 3-halo, —CN, —OH, —OCH$_2$CH=CHCl, —$C_1$-$C_8$ alkyl, —$C_1$-$C_6$ alkyl, —$C_1$-$C_4$ alkyl, —O—$C_1$-$C_8$ alkyl, or —S—$C_1$-$C_8$ alkyl; and at each occurrence alkyl is optionally substituted with 1-5 halo, —CN, or —OH. Examples of this include examples 1-7, 10-11, 14, 17-21, 23, 27-35, 37-39, 41, 43-44, 46, 48, 52, 57-58, 60 and 61. Pyrimidine examples are 46, 52, 57, 58 and 61. Phenyl or —$C_1$-$C_8$ alkylphenyl is optionally independently substituted with 1 or 2-halo, —CN, —OH, —OCH$_2$CH=CHCl, —$C_1$-$C_6$ alkyl, —O—$C_1$-$C_6$ alkyl, or —S—$C_1$-$C_6$ alkyl; and at each occurrence alkyl is optionally substituted with 1-5 halo, —CN, or —OH. Examples 1-7, 10-11, 14, 17-21, 23, 28-35, 37-39, 41, 43-44, 46, 48, 52, 57, 58, 60 and 61. Pyrimidine examples are 46, 52, 57, 58, and 61. Phenyl or —$C_1$-$C_8$ alkylphenyl is optionally independently substituted with 1-halo, —CN, —OH, —OCH$_2$CH=CHCl, —$C_1$-$C_8$ alkyl, —O—$C_1$-$C_8$ alkyl, or —S—$C_1$-$C_8$ alkyl; and at each occurrence alkyl is optionally substituted with 1-5 halo, —CN, or —OH. Examples 2-3, 29-31, 33, 44, 46, 57-58, and 61. Pyrimidine examples are 46, 57, 58 and 61.

Sometimes one or two substituents selected from Z, X, $R_3$ and $R_2$ will be substituted with only one substituent at the same time the other substituent will have two or more attachments, so for example we describe compounds where X is optionally independently substituted with 1-halo, —CN, —OH, —OCH$_2$CH=CHCl, —$C_1$-$C_8$ alkyl, —O—$C_1$-$C_8$ alkyl, or —S—$C_1$-$C_8$ alkyl; $R_2$ or $R_3$ is optionally independently substituted with 1-halo, —CN, —OH, —OCH$_2$CHHCl, —$C_1$-$C_8$ alkyl, —O—$C_1$-$C_8$ alkyl, or —S—$C_1$-$C_8$ alkyl; Z is optionally independently substituted with 2-halo, —CN, —OH, —OCH$_2$CH=CHCl, —$C_1$-$C_8$ alkyl, —O—$C_1$-$C_8$ alkyl, or —S—$C_1$-$C_8$ alkyl; and at each occurrence alkyl is optionally substituted with 1-5 halo, —CN, or —OH. Examples of these types of compounds are provided by examples 1, 2, 4, 6, 7, 10, 11, 14, 17, 18, 19, 20, 21, 23, 28, 32, 37, 41, 43, 52, 57, 58, 60 and 61. Pyrimidine examples of this type are examples 46, 52, 57, 58, and 61.

Compounds are described where some moieties have two substituents attached to one ring and other rings have just one substituent, for example, where X is optionally independently substituted with 1 or 2-halo, —CN, —OH, —OCH$_2$CH=CHCl, —C$_1$-C$_8$ alkyl, —O—C$_1$-C$_8$ alkyl, or —S—C$_1$-C$_8$ alkyl; R$_2$ or R$_3$ is optionally independently substituted with 1-halo, —CN, —OH, —OCH$_2$CH=CHCl, —C$_1$-C$_8$ alkyl, —O—C$_1$-C$_8$ alkyl, or —S—C$_1$-C$_8$ alkyl; Z is optionally independently substituted with 1 or 2-halo, —CN, —OH, —OCH$_2$CH=CHCl, —C$_1$-C$_8$ alkyl, —O—C$_1$-C$_8$ alkyl, or —S—C$_1$-C$_8$ alkyl; and at each occurrence alkyl is optionally substituted with 1-5 halo, —CN, or —OH. And when X is optionally independently substituted with 1-halo, —CN, —OH, —OCH$_2$CHHCl, —C$_1$-C$_8$ alkyl, —O—C$_1$-C$_8$ alkyl, or —S—C$_1$-C$_8$ alkyl; R$_2$ or R$_3$ is optionally independently substituted with 1 or 2-halo, —CN, —OH, —OCH$_2$CH=CHCl, —C$_1$-C$_8$ alkyl, —O—C$_1$-C$_8$ alkyl, or —S—C$_1$-C$_8$ alkyl; Z is optionally independently substituted with 1-halo, —CN, —OH, —OCH$_2$CH=CHCl, —C$_1$-C$_8$ alkyl, —O—C$_1$-C$_8$ alkyl, or —S—C$_1$-C$_8$ alkyl; and at each occurrence alkyl is optionally substituted with 1-5 halo, —CN, or —OH.

We specifically describe compounds of the type described above wherein aryl may have 1, 2, or 3 substitutions according to the compounds, Formula and positions indicated for any of the Formula below. In the Formula below R is -halo, —CN, —OH, —OCH$_2$CH=CHCl, —C$_1$-C$_6$ alkyl, —O—C$_1$-C$_6$ alkyl, or —S—C$_1$-C$_6$ alkyl and at each occurrence, alkyl or —C$_1$-C$_6$ alkyl, is optionally independently substituted with 1-5 halo, CN or —OH. General and specific examples are provided.

Aryl as phenyl with 1-3 groups attached are represented by the structures below where R$_{10}$ is independently selected from -halo, —CN, —OH, —OCH$_2$CH=CHCl, —C$_1$-C$_6$ alkyl, —O—C$_1$-C$_6$ alkyl, or —S—C$_1$-C$_6$ alkyl; and at each occurrence alkyl is optionally substituted with 1-5 halo, —CN, or —OH. R$_{het}$ is selected from N, O, and S, N and O are preferred.

This document has various tables. In the Tables R$_{10}$ may be any substituent as described herein and in other tables, including independently selected from -halo, —CN, —OH, —OCH$_2$CH=CHCl, —C$_1$-C$_6$ alkyl, —O—C$_1$-C$_6$ alkyl, or —S—C$_1$-C$_6$ alkyl; and at each occurrence alkyl is optionally substituted with 1-5 halo, —CN, or —OH. Rhet is N, O, or S, N and O are preferred.

Compounds where aryl is phenyl and substituted as shown below in Table 1, Formulas Phenyl 1-15, are described.

TABLE 1

Phenyl 1-15.

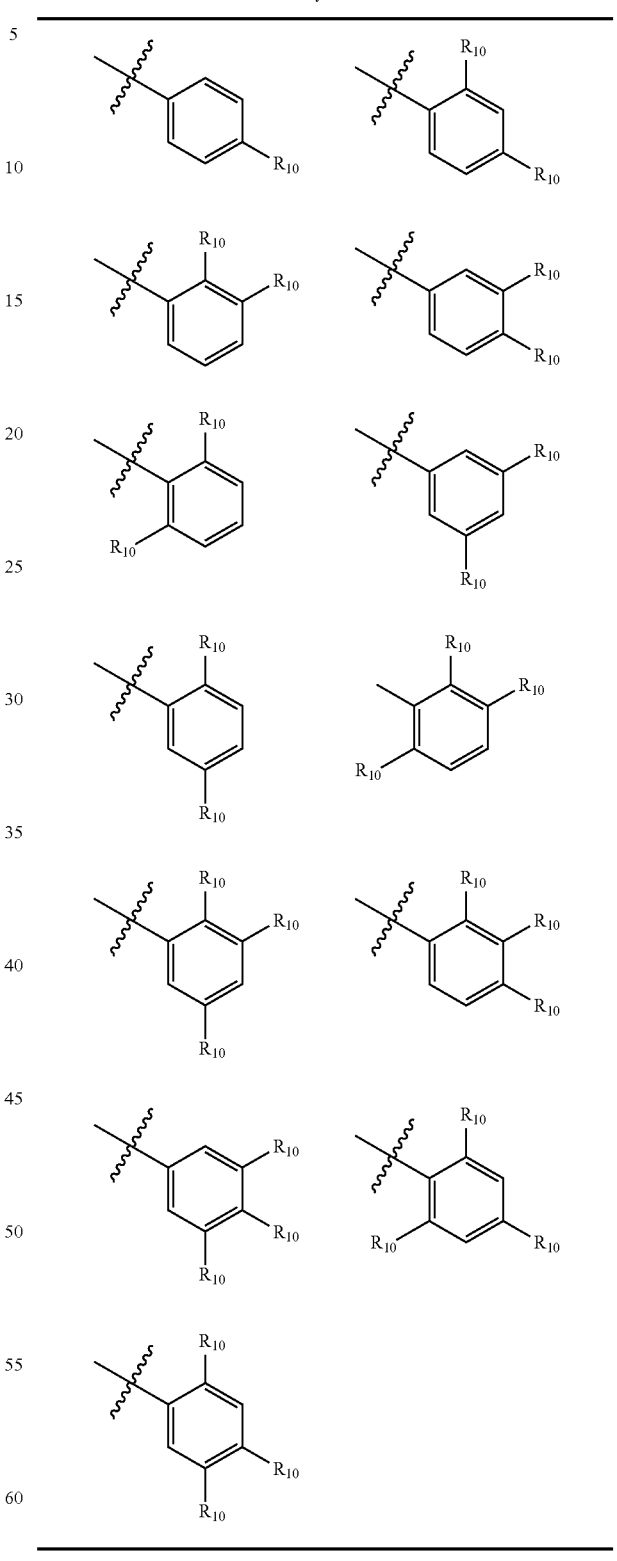

Compounds where heterocyclic is a 5, 6, or 10 member cyclic ring as shown in the Formulas below are described in Table 2. Compounds where heterocyclic is a 6 member cyclic ring. Formulas C$_6$ Hetero 1-83.

TABLE 2
Formulas C$_6$ Hetero 1-83.
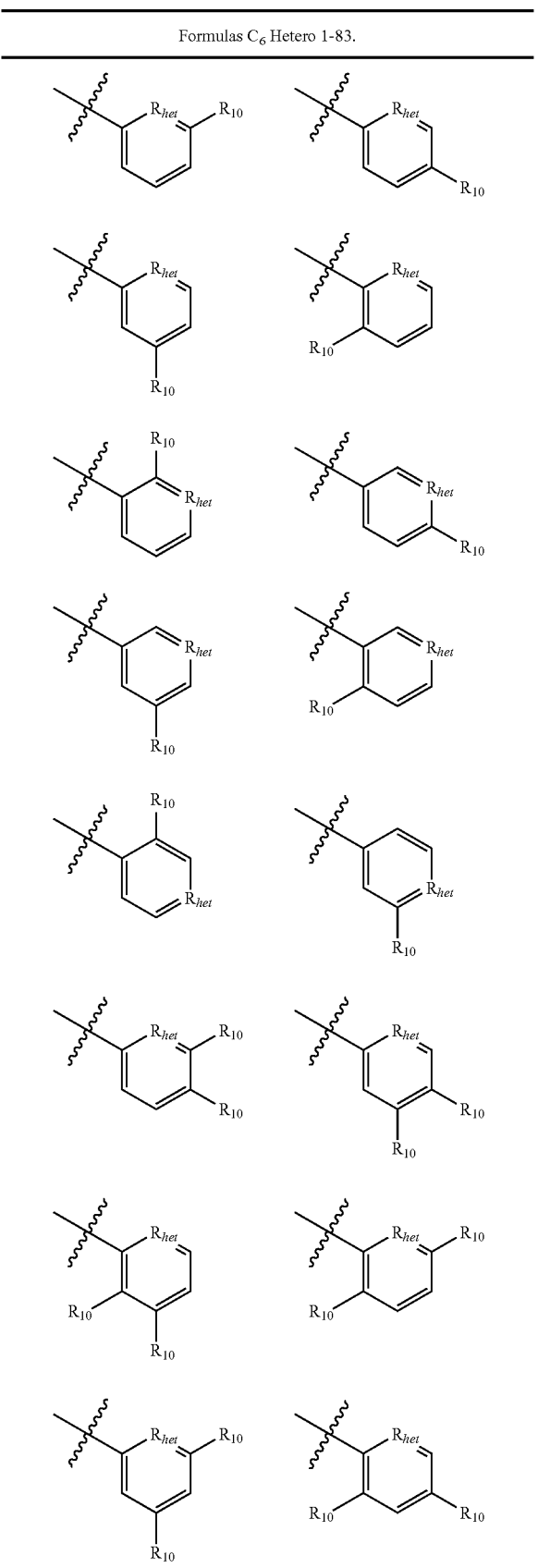
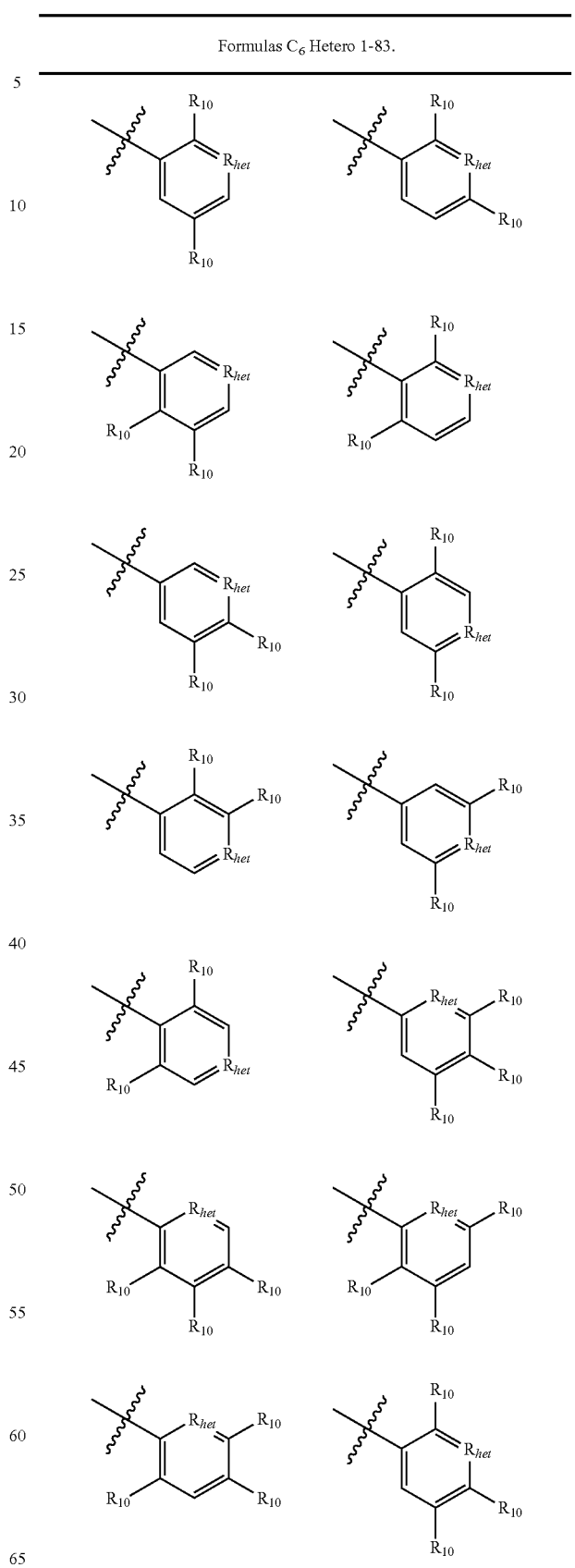

TABLE 2-continued
Formulas C$_6$ Hetero 1-83.
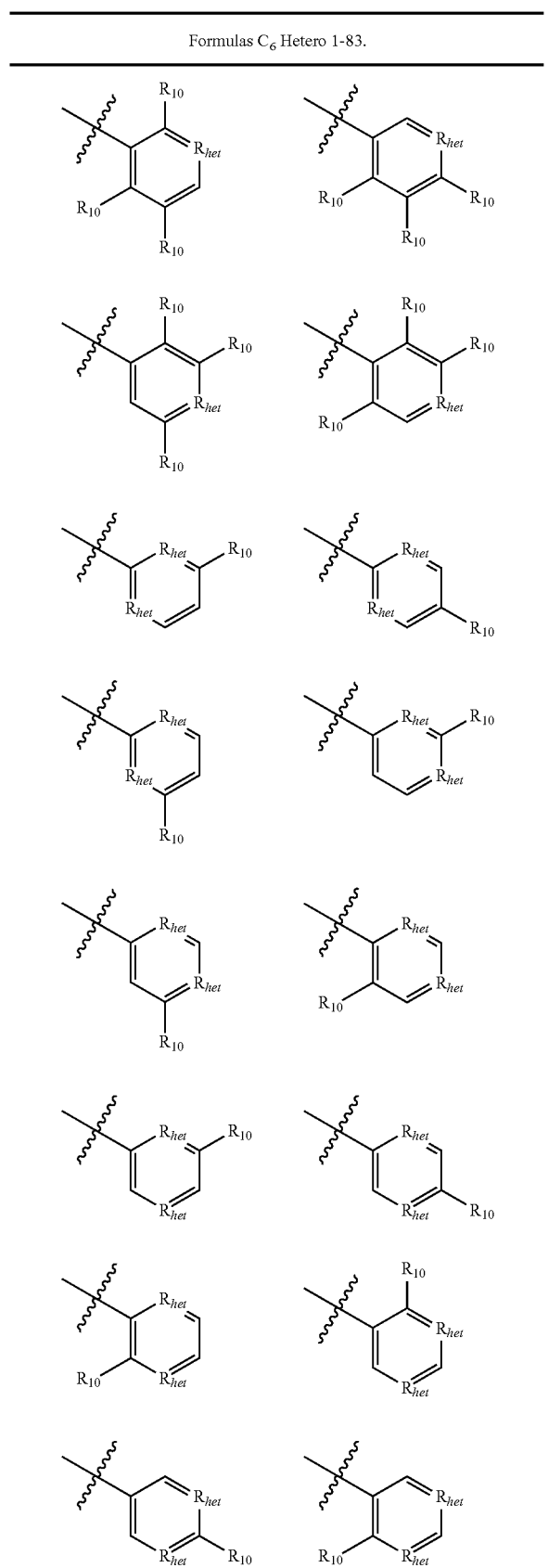
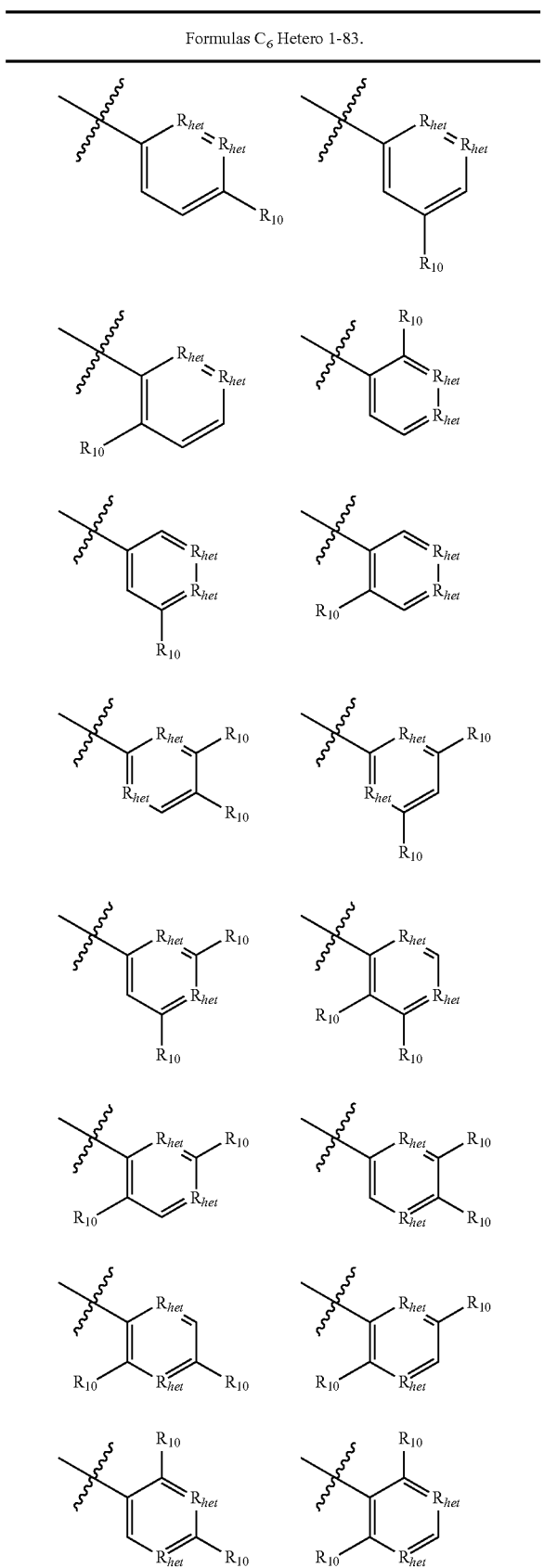

TABLE 2-continued
Formulas C$_6$ Hetero 1-83.
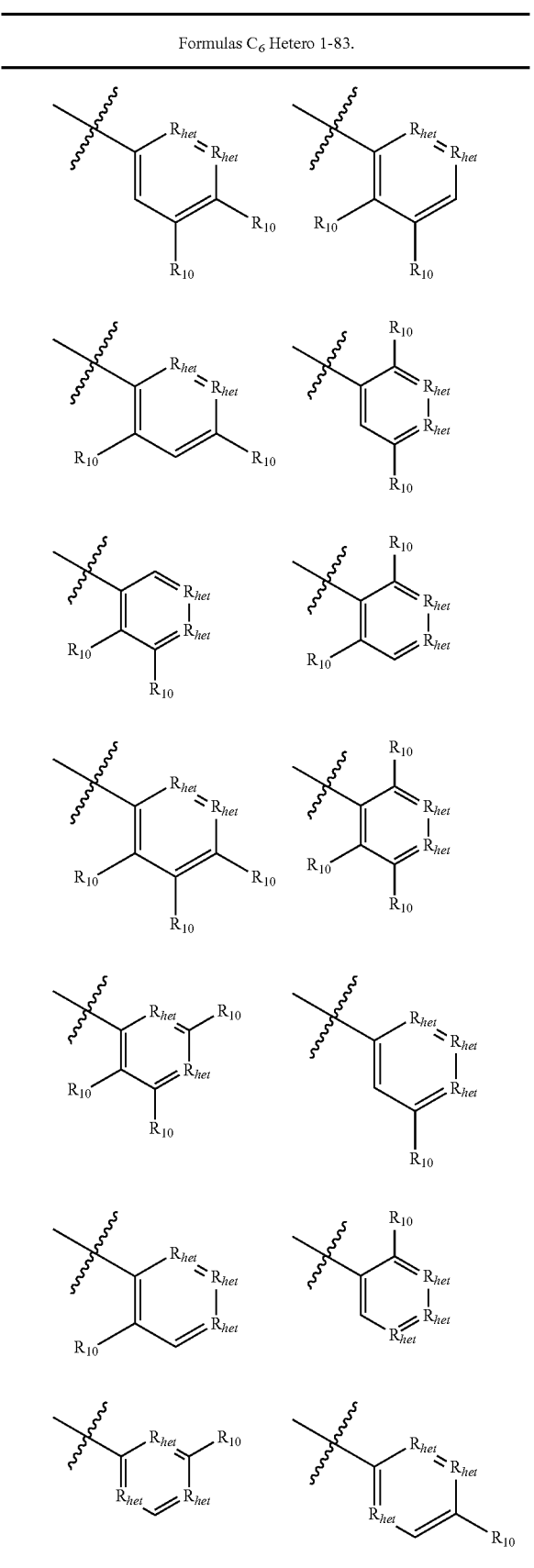
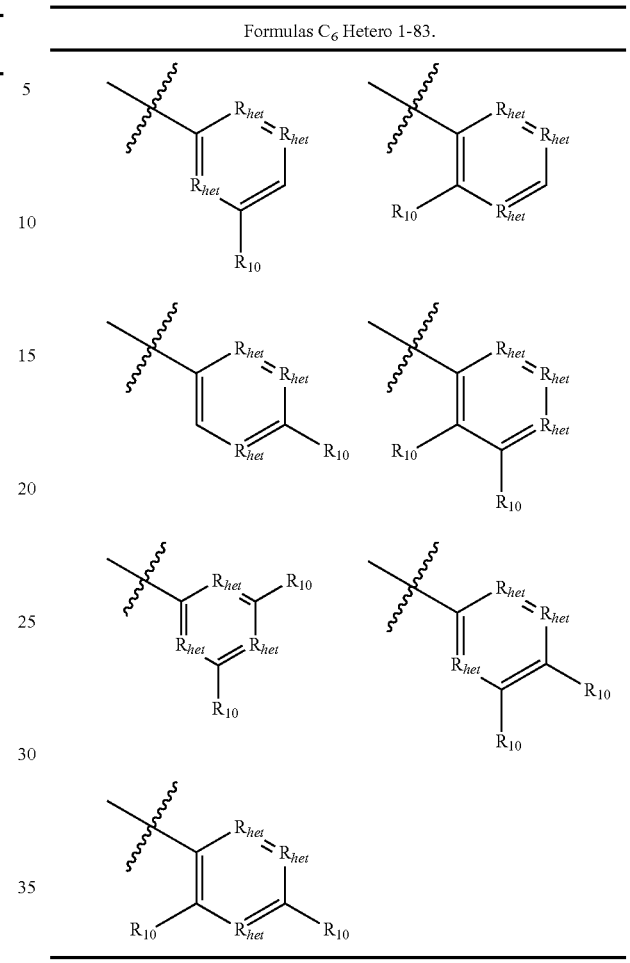
Compounds where heterocyclic is a 5 member cyclic ring are described below in Table 3. Formulas C$_5$ Hetero 1-95.
TABLE 3
Formula C$_5$ 1-95.
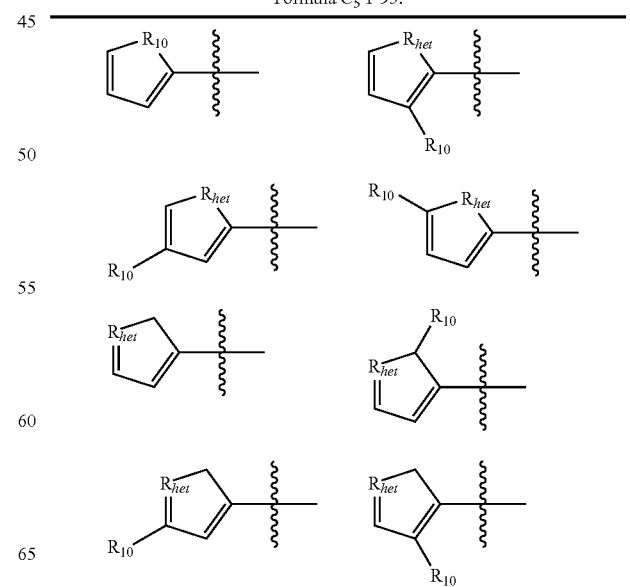

TABLE 3-continued
Formula C₅ 1-95.
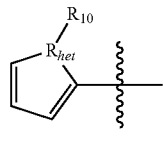 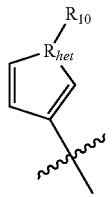
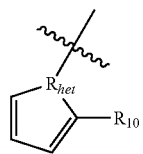 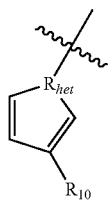
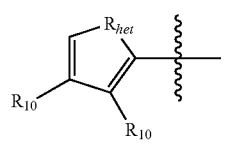 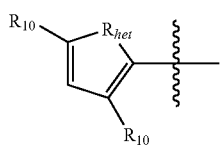
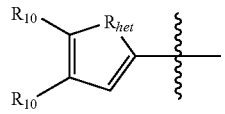 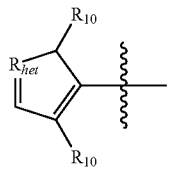
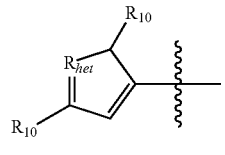 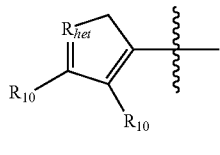
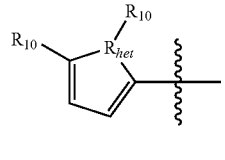 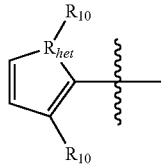
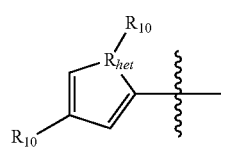 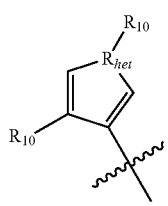
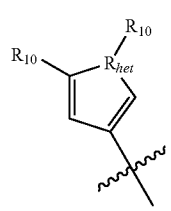 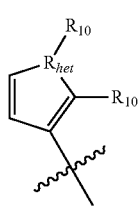
TABLE 3-continued
Formula C₅ 1-95.
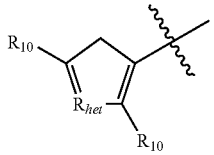 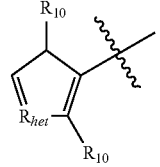
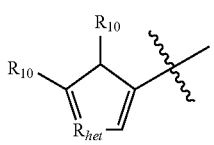 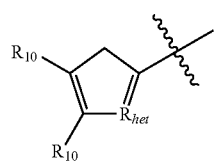
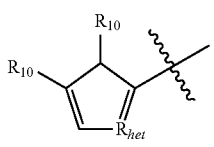 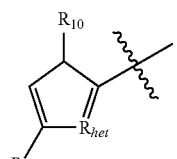
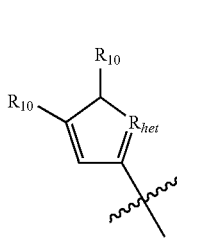 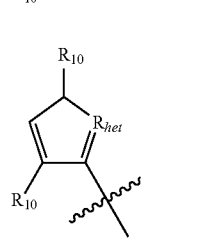
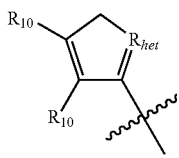 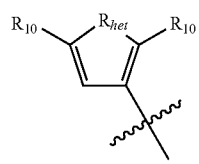
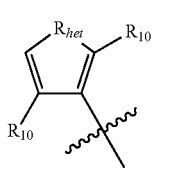 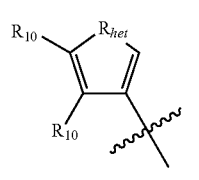
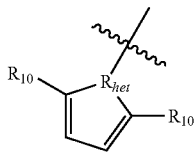 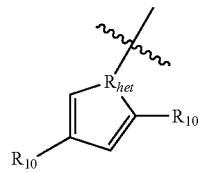
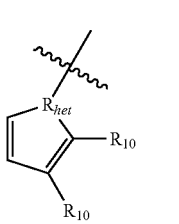 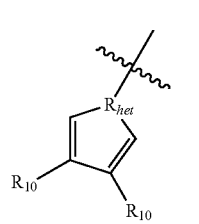

TABLE 3-continued
Formula C₅ 1-95.
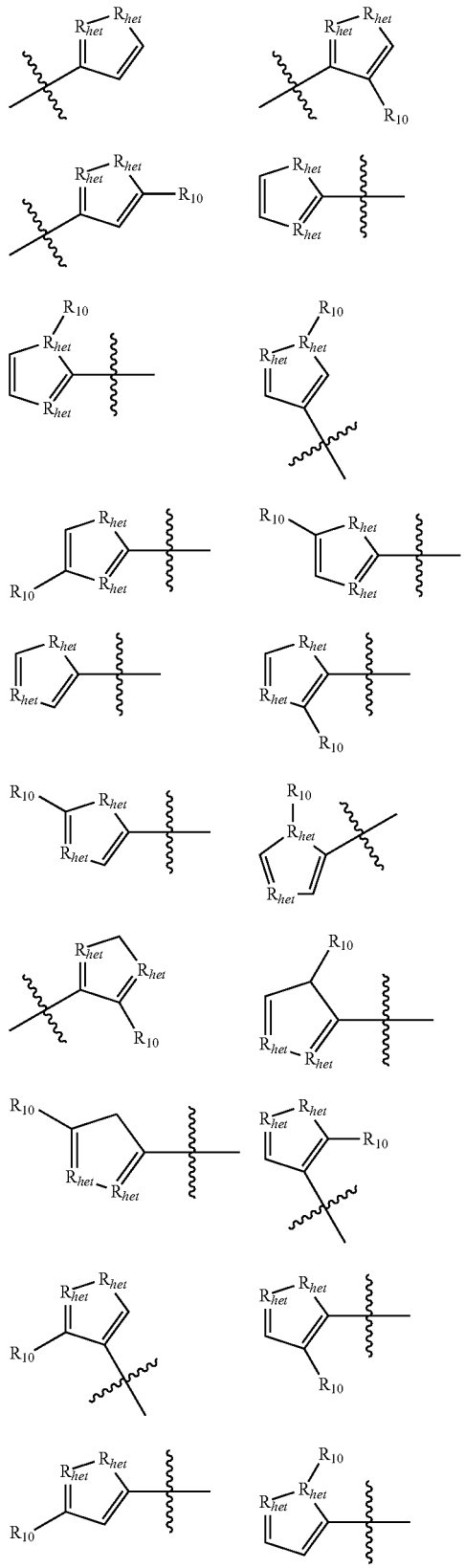
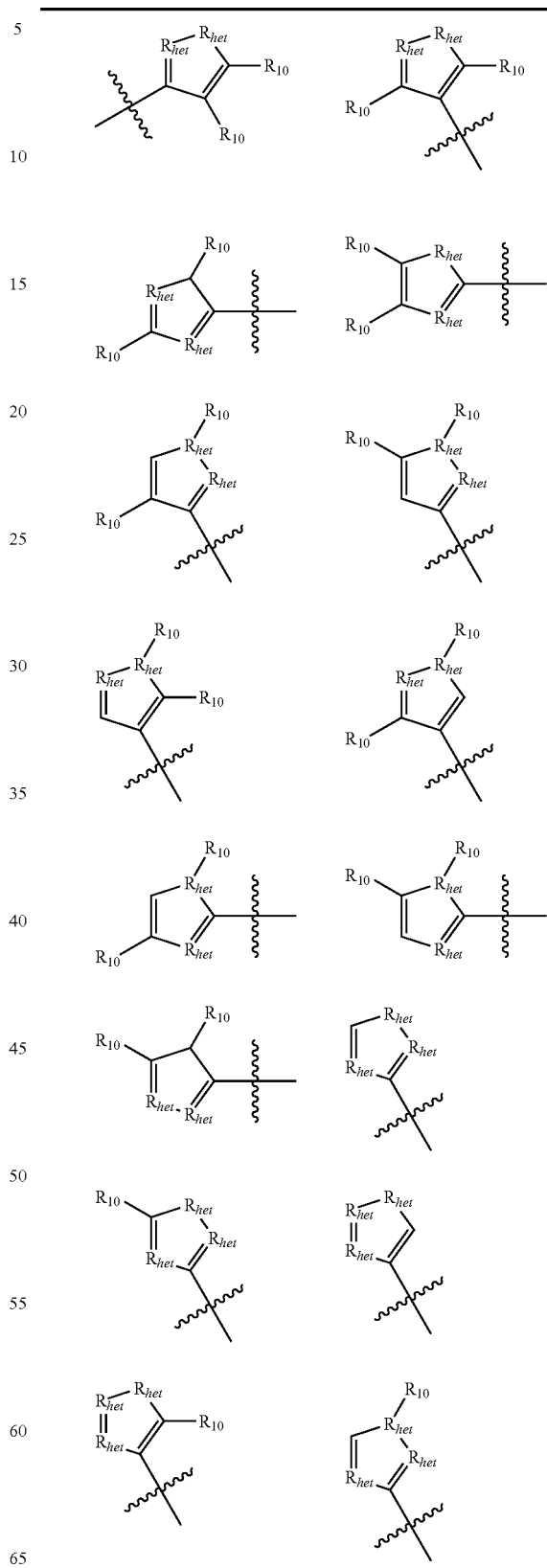

TABLE 3-continued
Formula C₅ 1-95.
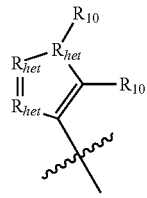
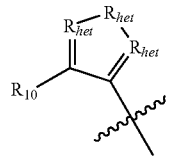
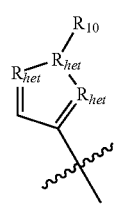
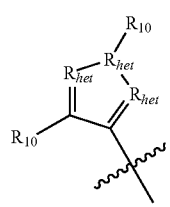
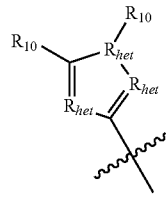
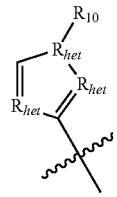
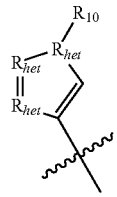
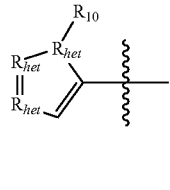
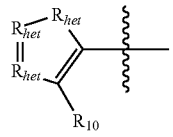
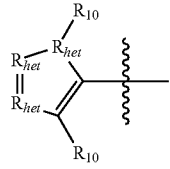
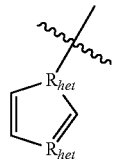
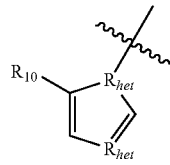
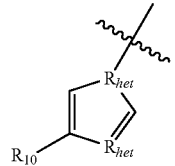
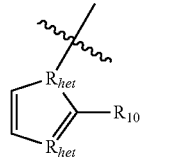
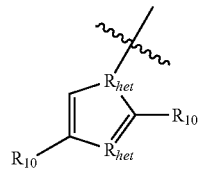
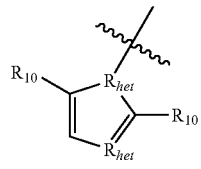
TABLE 3-continued
Formula C₅ 1-95.
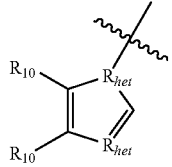
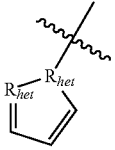
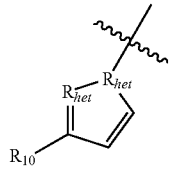
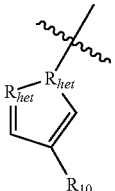
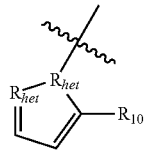
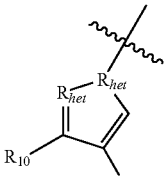
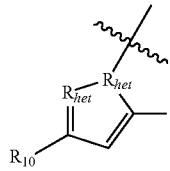
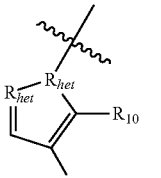
Compounds where heterocyclic is a 10 member cyclic ring are described below in Table 4. Formulas $C_{10}$ Hetero 1-283. N can be $R_{het}$ in the figures below.
TABLE 4
Formulas $C_{10}$ Hetero 1-283.
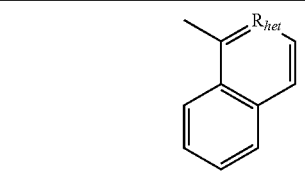
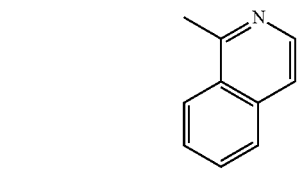
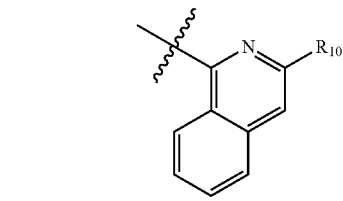

TABLE 4-continued
Formulas C$_{10}$ Hetero 1-283.
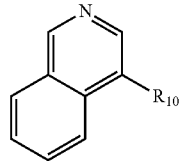
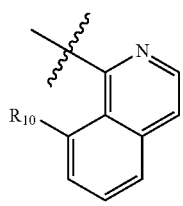
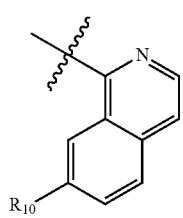
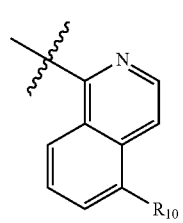
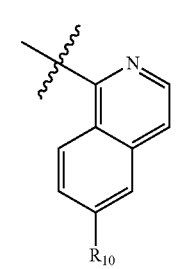
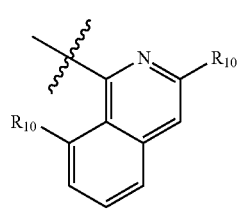
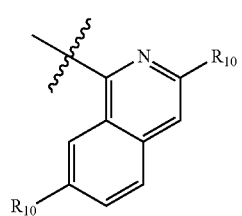
TABLE 4-continued
Formulas C$_{10}$ Hetero 1-283.
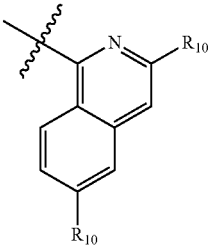
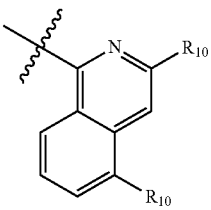
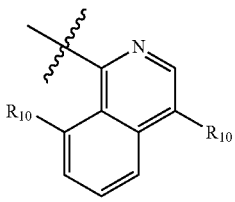
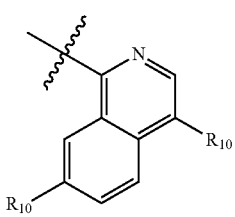
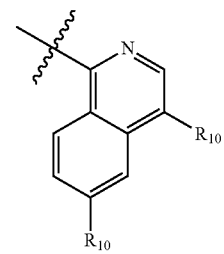
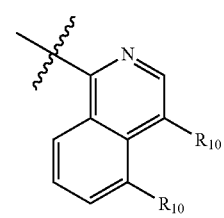
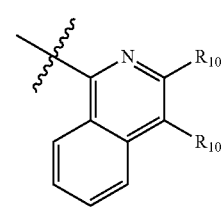

TABLE 4-continued
Formulas C₁₀ Hetero 1-283.
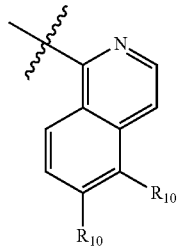
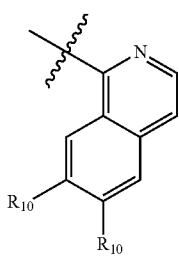
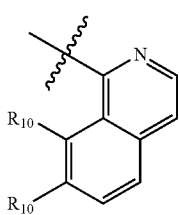
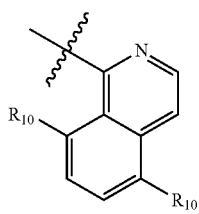
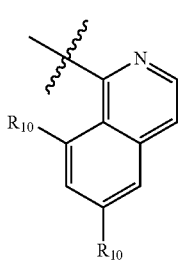
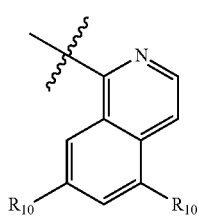
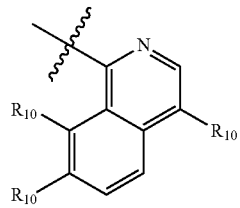
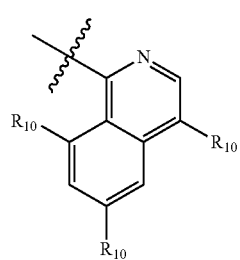
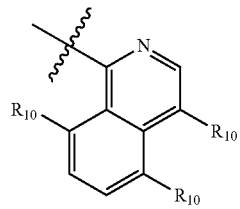
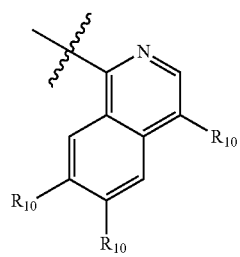
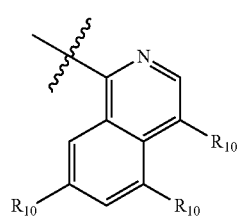
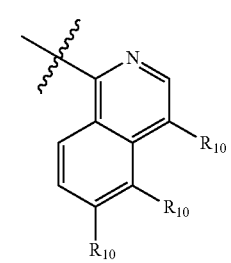

TABLE 4-continued
Formulas C$_{10}$ Hetero 1-283.
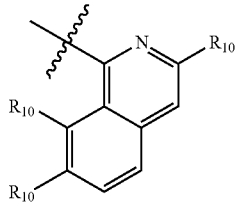
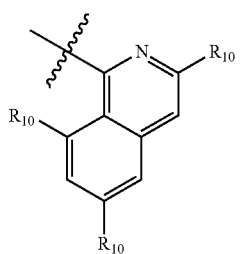
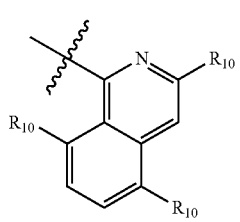
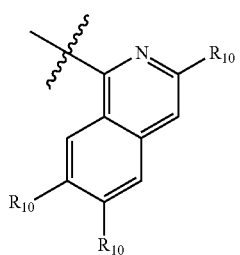
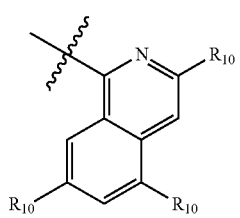
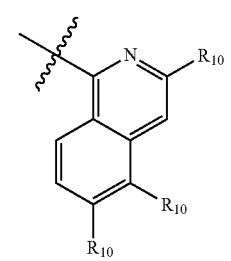
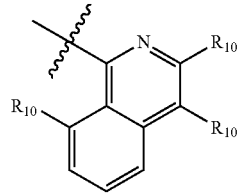
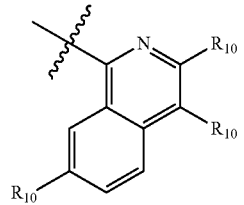
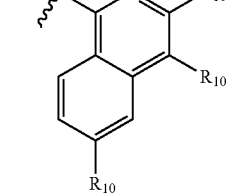
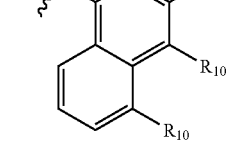
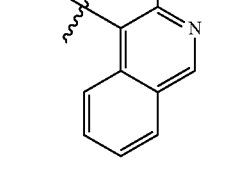
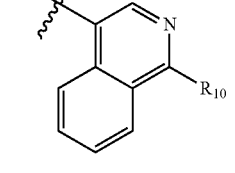
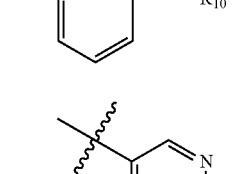
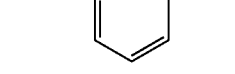

TABLE 4-continued
Formulas C₁₀ Hetero 1-283.
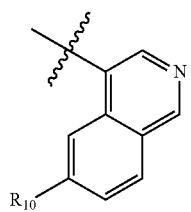
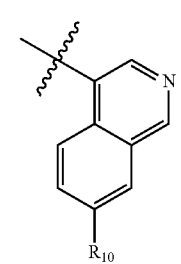
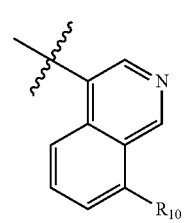
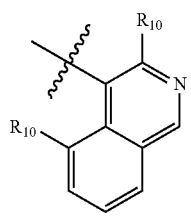
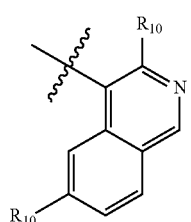
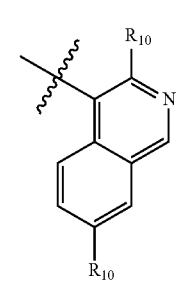
TABLE 4-continued
Formulas C₁₀ Hetero 1-283.
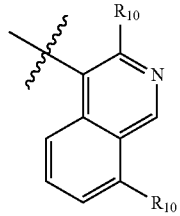
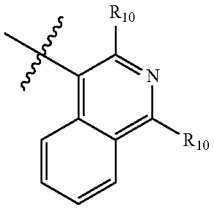
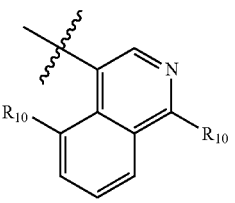
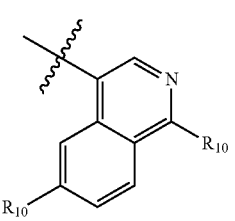
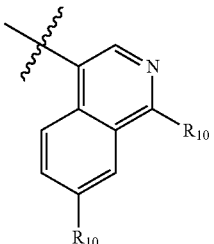
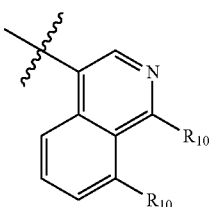
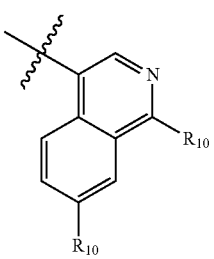

TABLE 4-continued
Formulas C$_{10}$ Hetero 1-283.
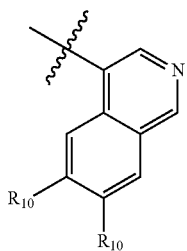
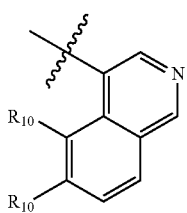
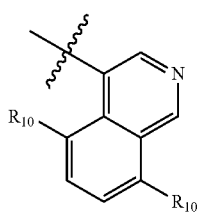
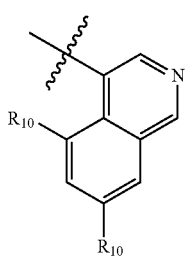
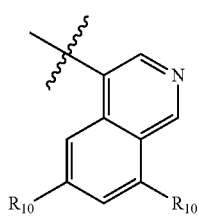
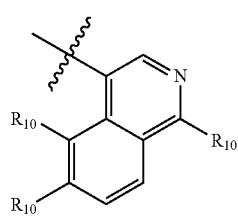
TABLE 4-continued
Formulas C$_{10}$ Hetero 1-283.
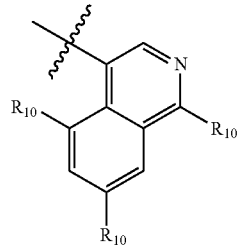
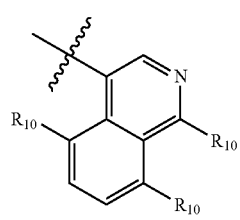
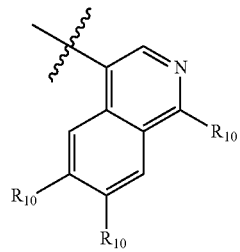
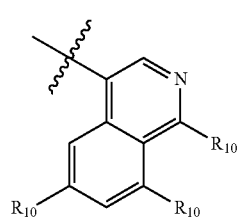
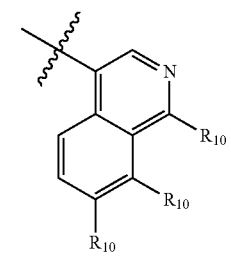
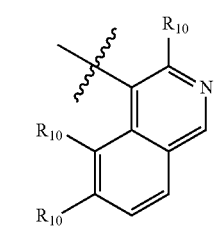

TABLE 4-continued
Formulas C$_{10}$ Hetero 1-283.
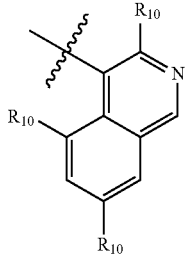
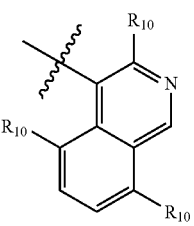
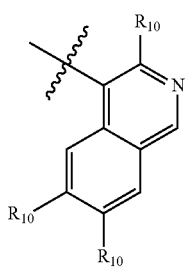
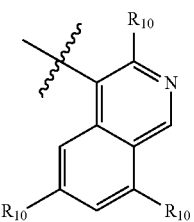
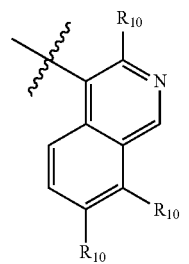
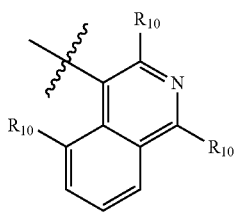
TABLE 4-continued
Formulas C$_{10}$ Hetero 1-283.
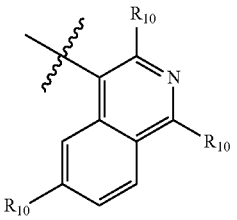
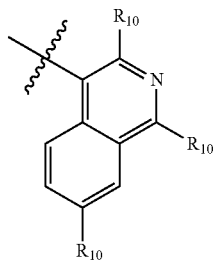
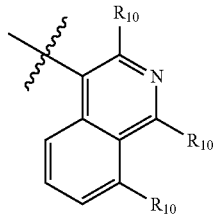
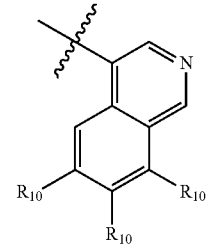
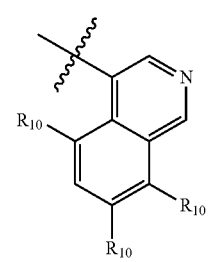
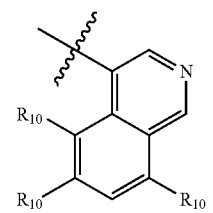

TABLE 4-continued
Formulas C₁₀ Hetero 1-283.
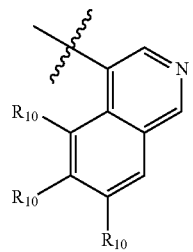
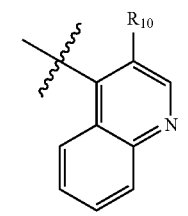
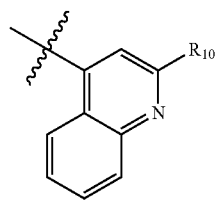
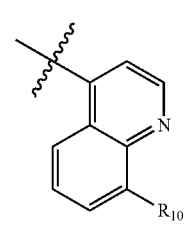
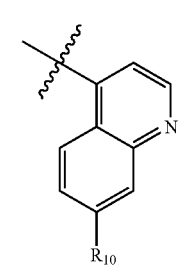
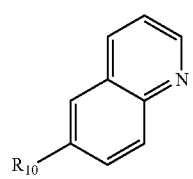
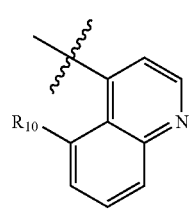
TABLE 4-continued
Formulas C₁₀ Hetero 1-283.
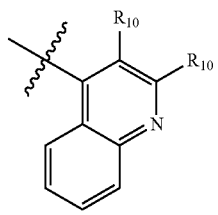
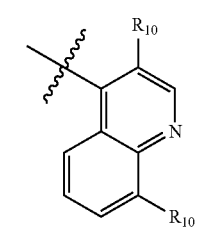
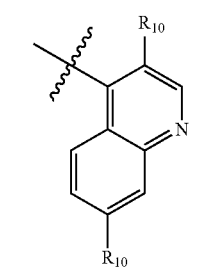
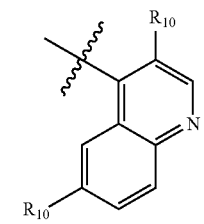
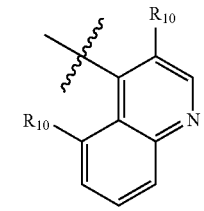
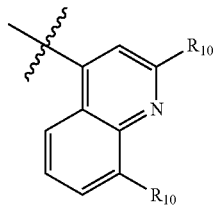

TABLE 4-continued
Formulas C$_{10}$ Hetero 1-283.
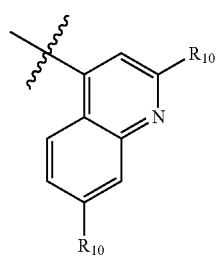
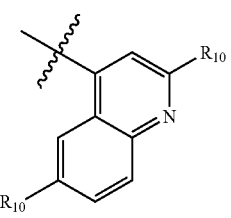
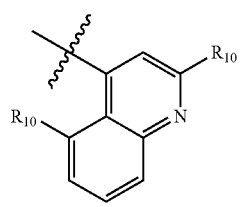
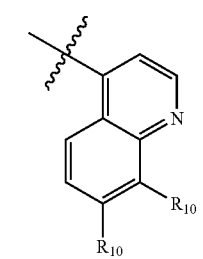
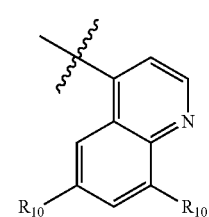
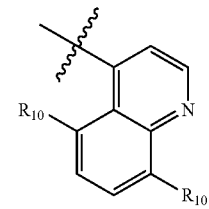
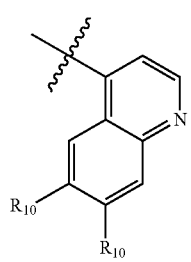
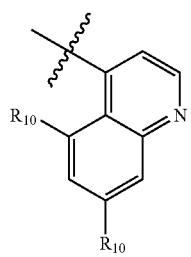
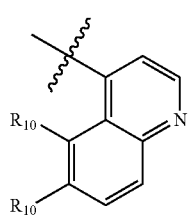
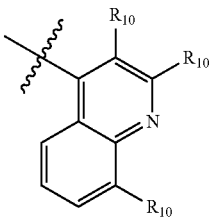
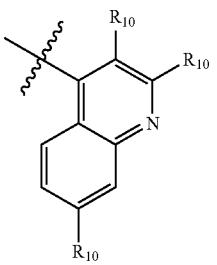
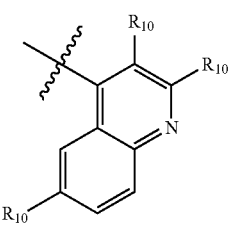

TABLE 4-continued
Formulas C₁₀ Hetero 1-283.
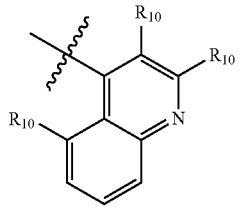
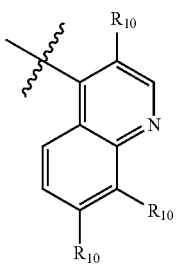
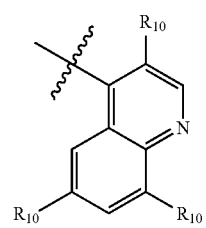
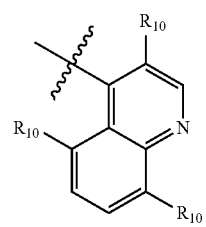
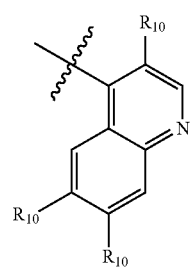
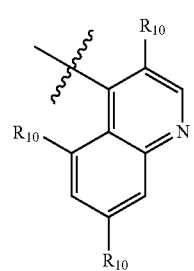
TABLE 4-continued
Formulas C₁₀ Hetero 1-283.
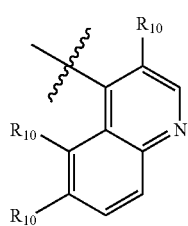
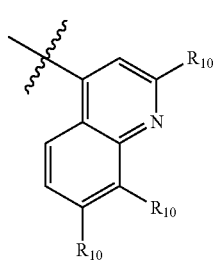
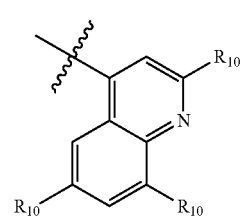
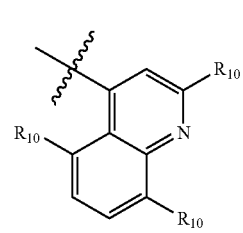
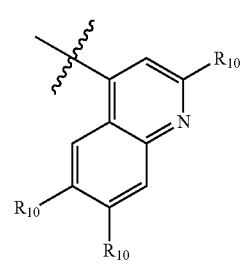
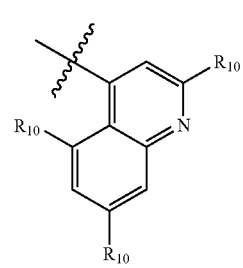

TABLE 4-continued
Formulas C$_{10}$ Hetero 1-283.
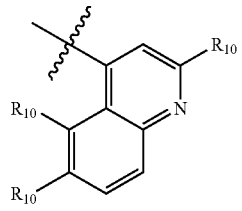
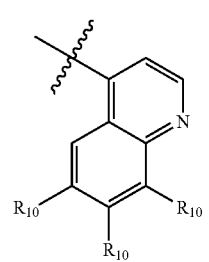
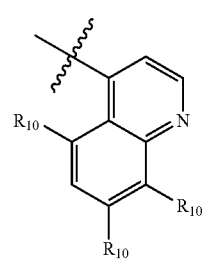
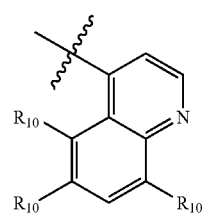
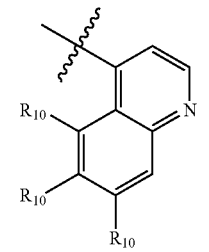
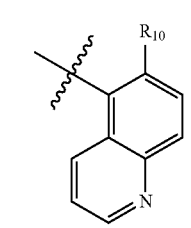
TABLE 4-continued
Formulas C$_{10}$ Hetero 1-283.
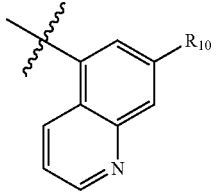
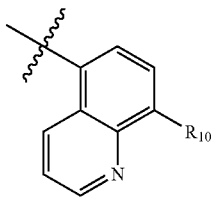
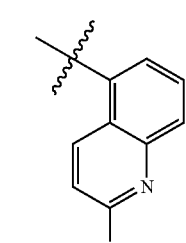
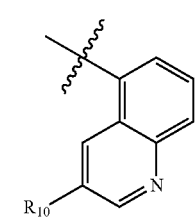
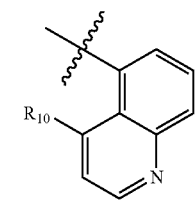
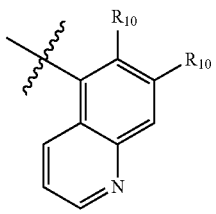

TABLE 4-continued
Formulas C$_{10}$ Hetero 1-283.
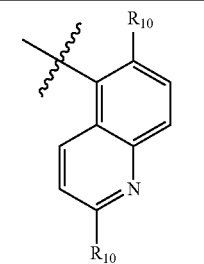
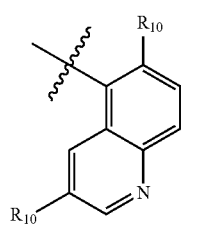
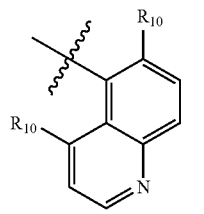
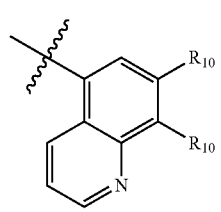
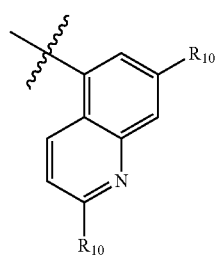
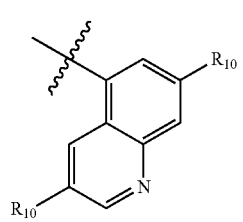
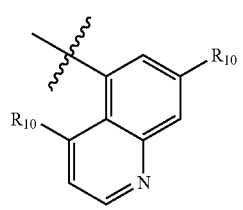
TABLE 4-continued
Formulas C$_{10}$ Hetero 1-283.
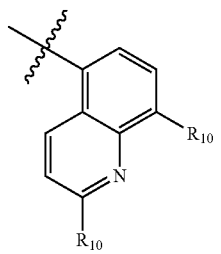
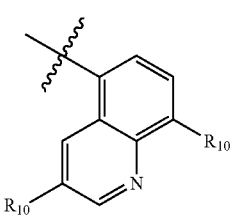
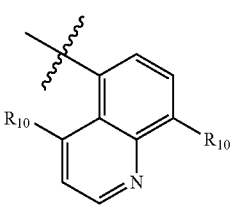
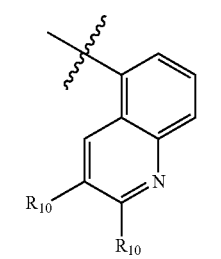
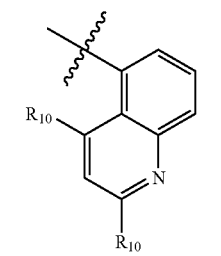
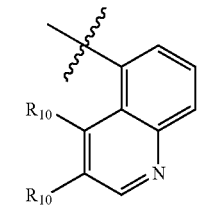

TABLE 4-continued
Formulas C10 Hetero 1-283.
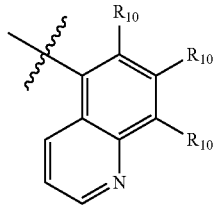
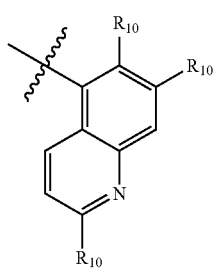
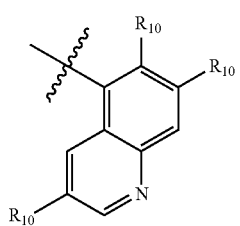
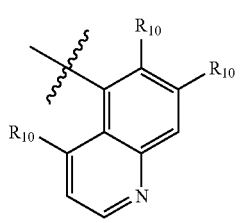
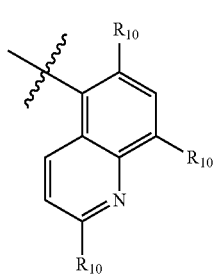
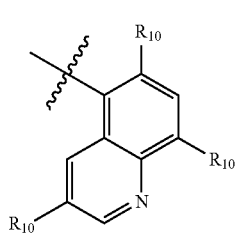
TABLE 4-continued
Formulas C10 Hetero 1-283.
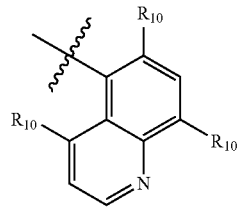
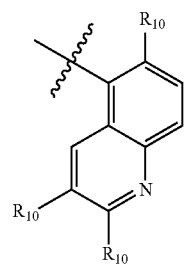
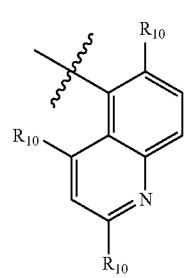
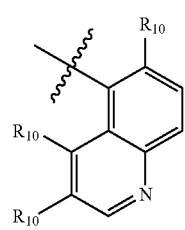
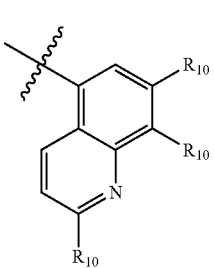
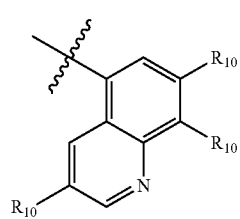

TABLE 4-continued
Formulas C$_{10}$ Hetero 1-283.
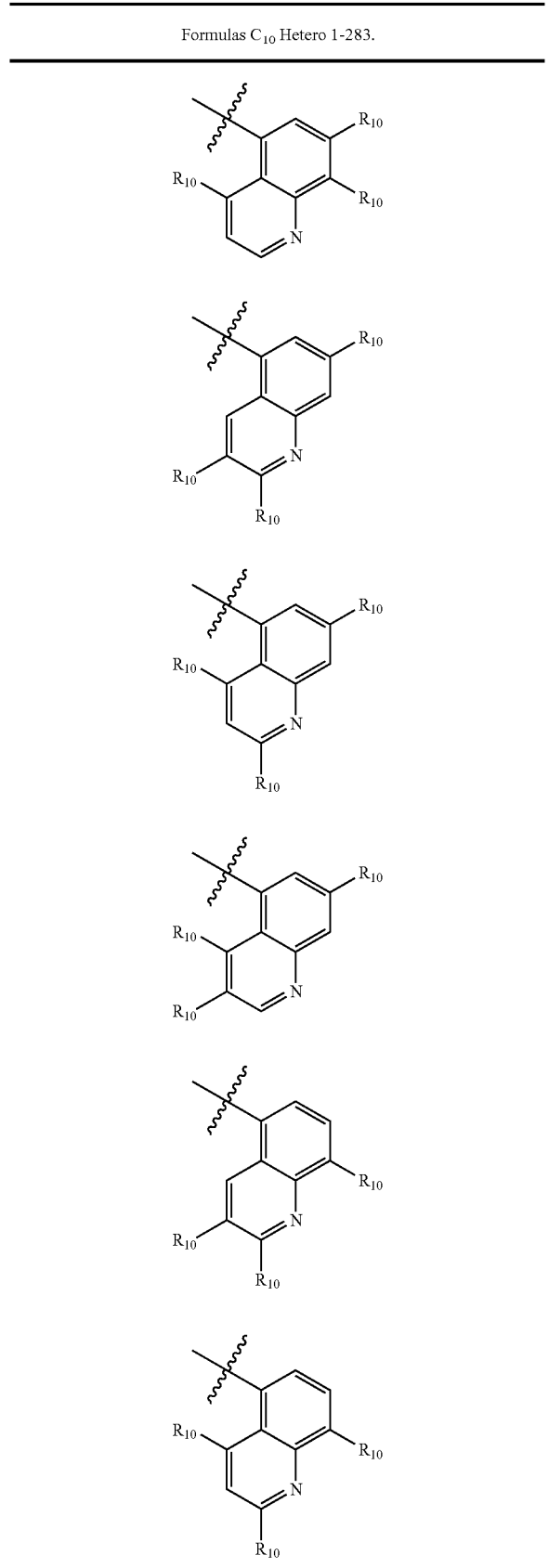
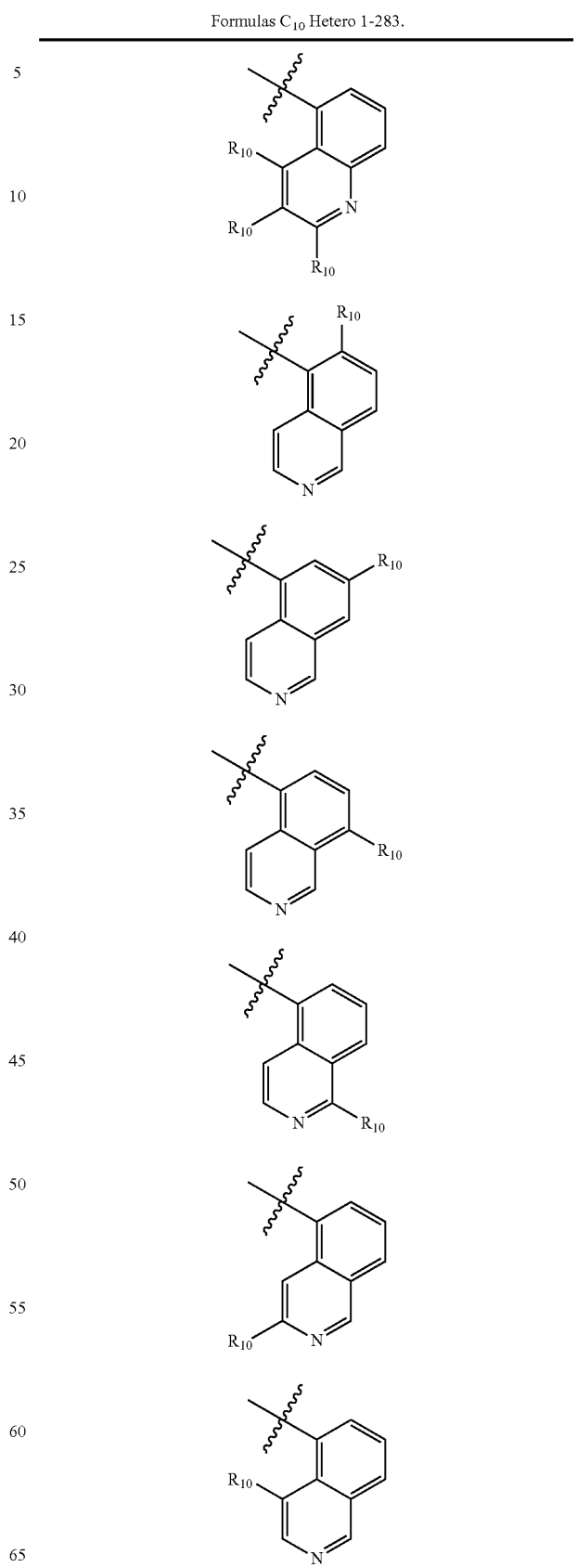

TABLE 4-continued
Formulas C10 Hetero 1-283.
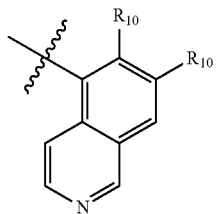
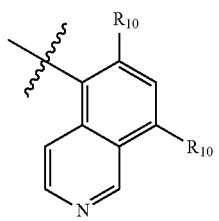
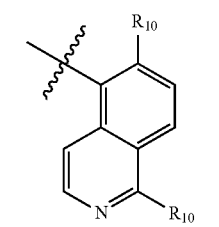
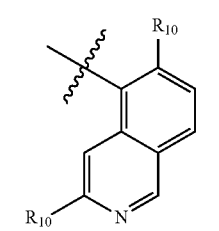
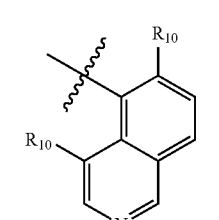
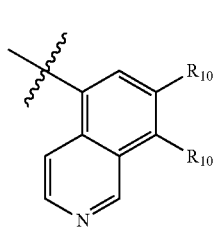
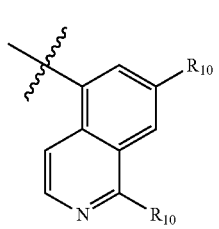
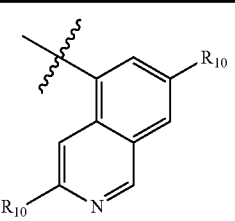
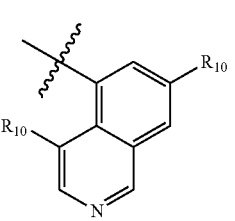
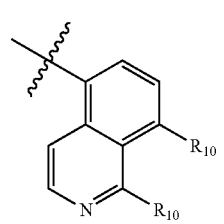
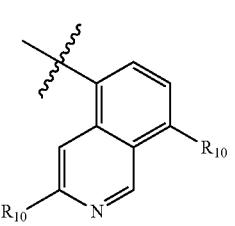
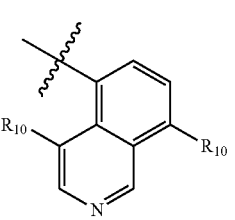
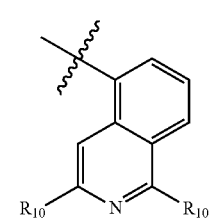
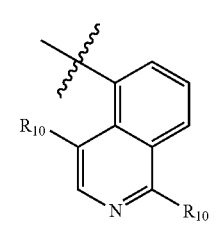

TABLE 4-continued
Formulas C$_{10}$ Hetero 1-283.
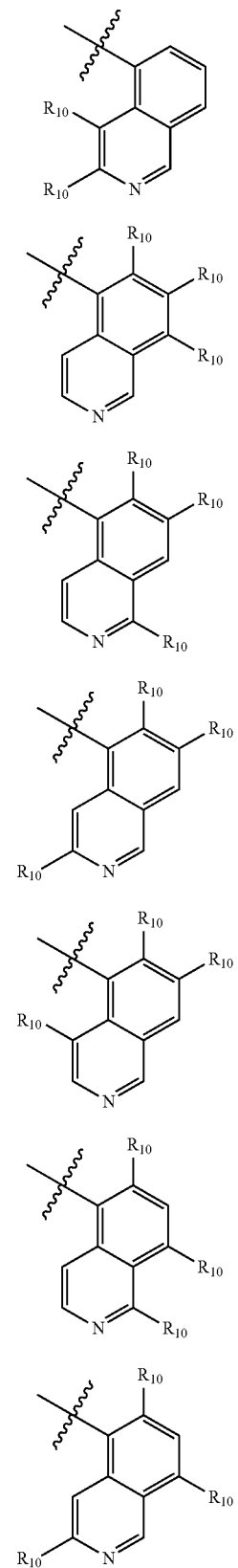
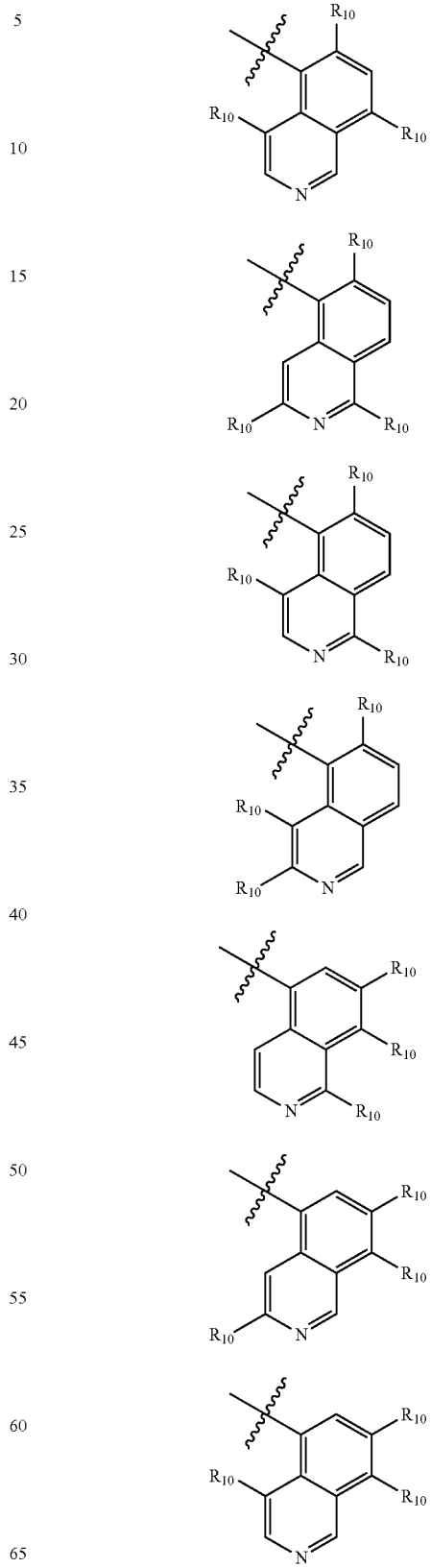

TABLE 4-continued
Formulas C$_{10}$ Hetero 1-283.
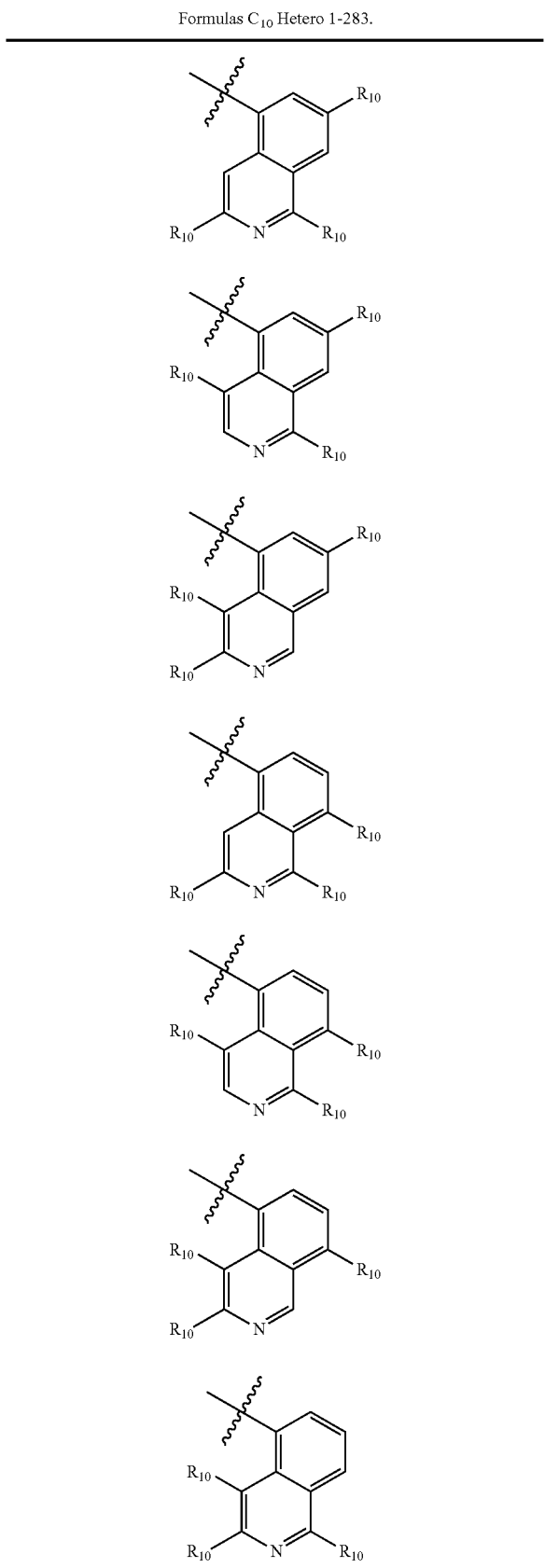
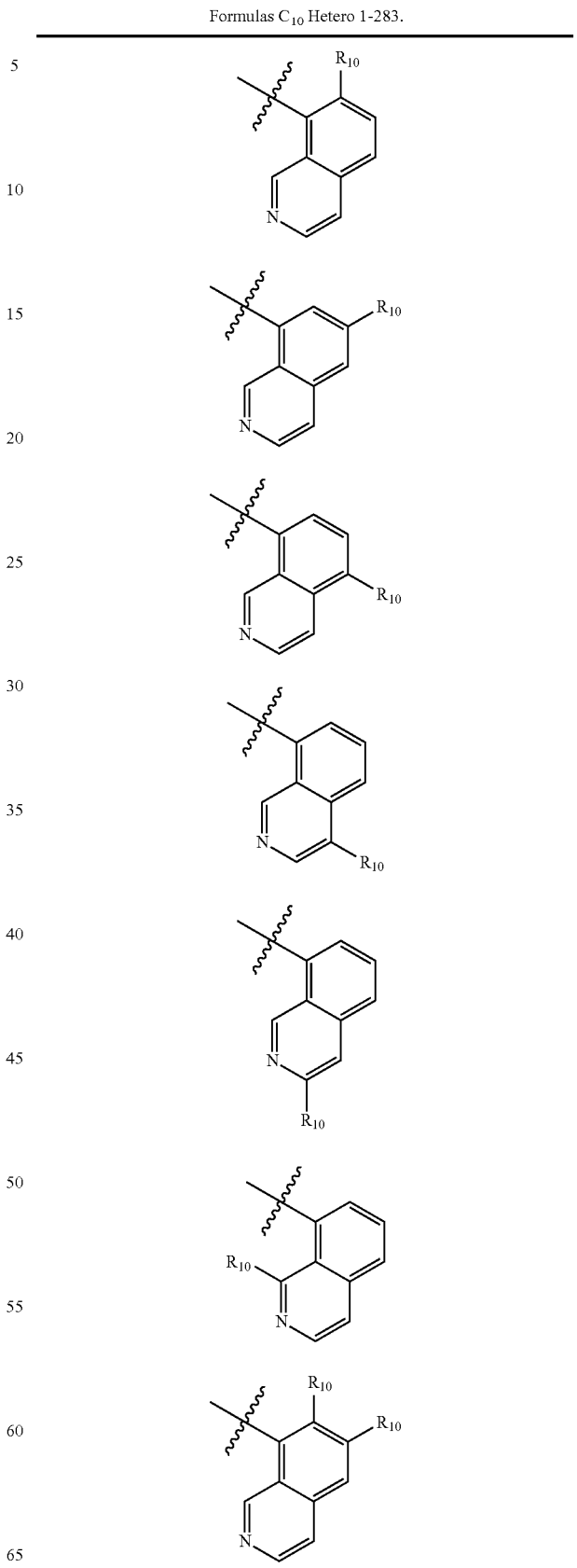

TABLE 4-continued
Formulas C$_{10}$ Hetero 1-283.
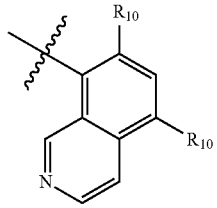
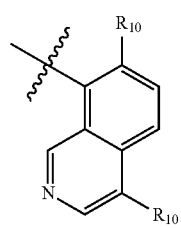
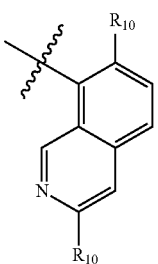
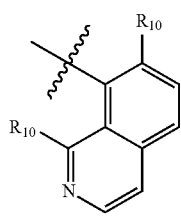
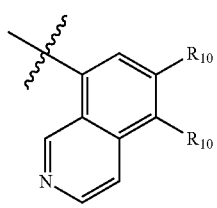
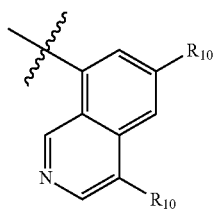
TABLE 4-continued
Formulas C$_{10}$ Hetero 1-283.
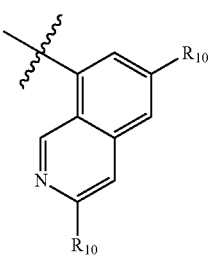
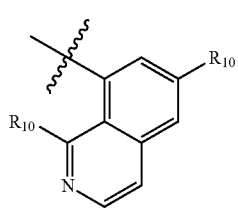
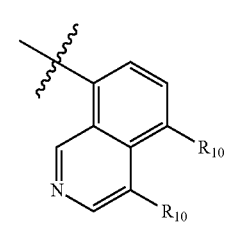
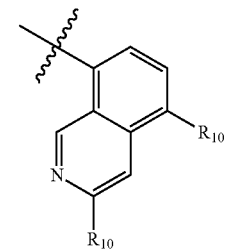
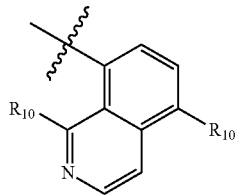
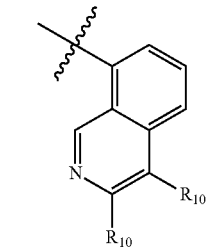

TABLE 4-continued
Formulas C₁₀ Hetero 1-283.
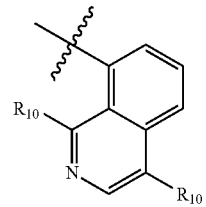
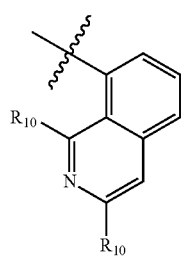
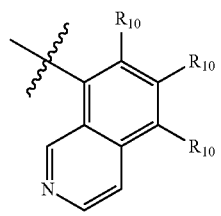
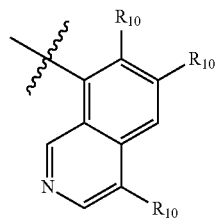
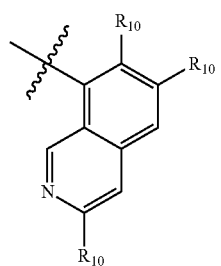
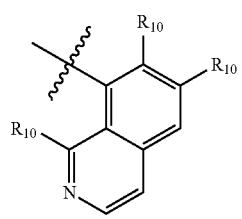
TABLE 4-continued
Formulas C₁₀ Hetero 1-283.
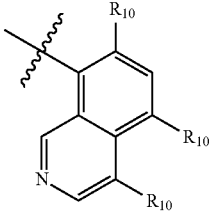
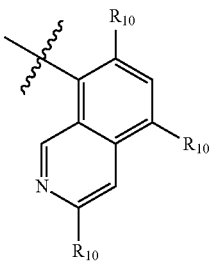
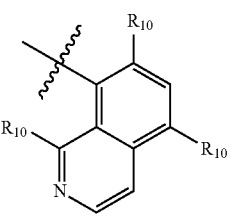
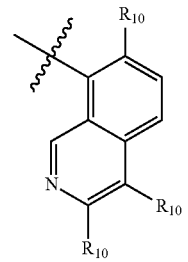
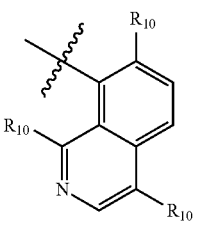
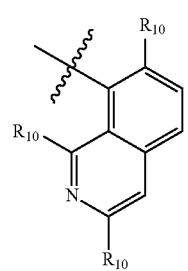

TABLE 4-continued
Formulas C$_{10}$ Hetero 1-283.
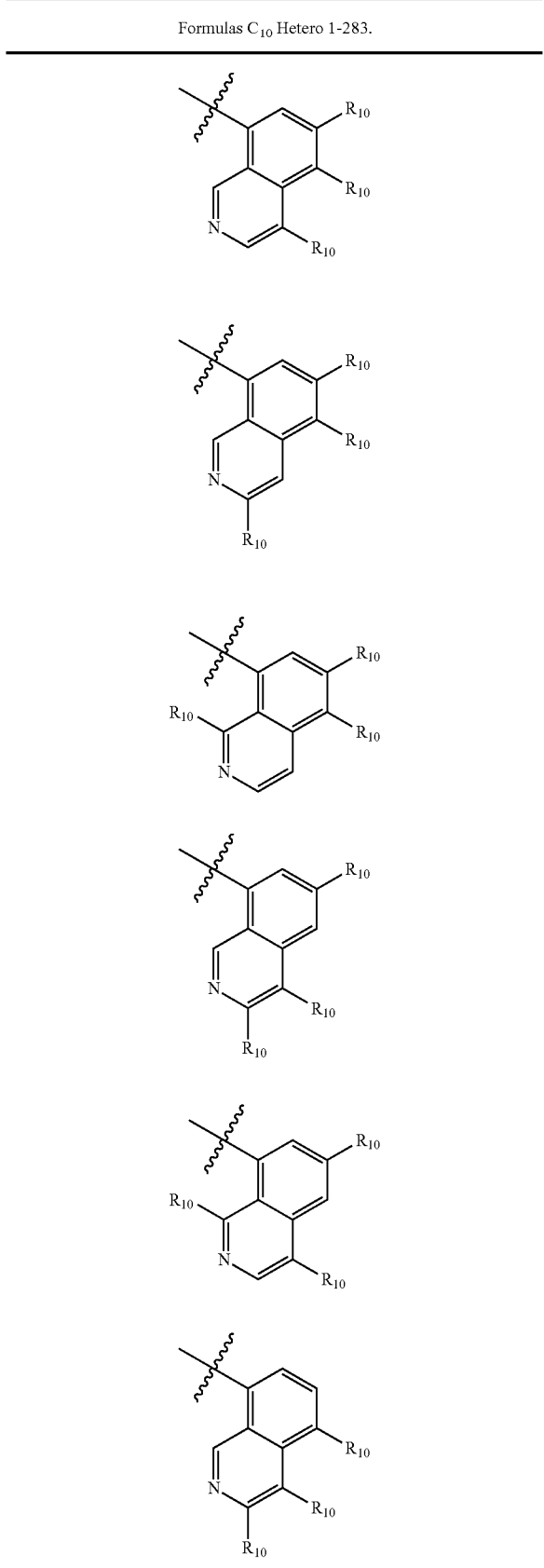
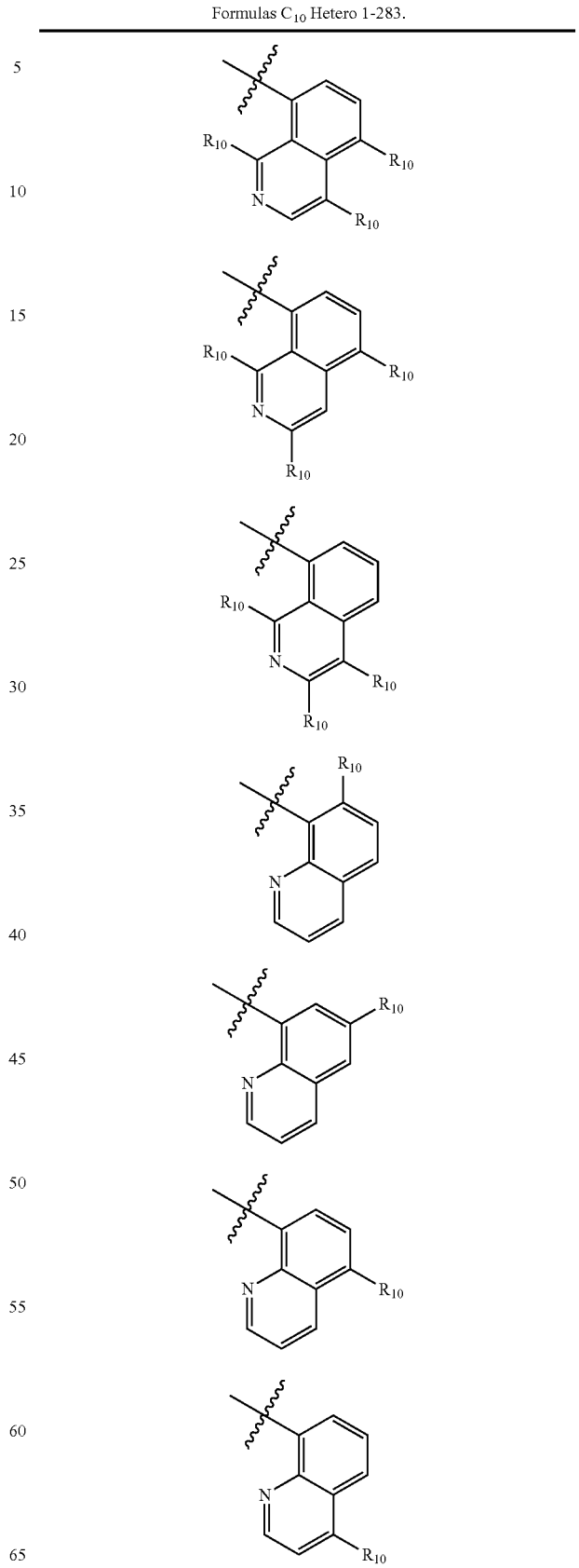

TABLE 4-continued
Formulas C₁₀ Hetero 1-283.
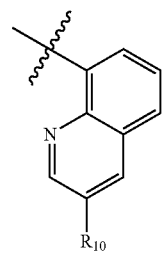
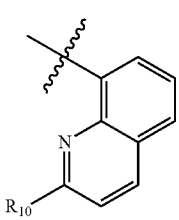
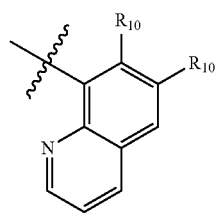
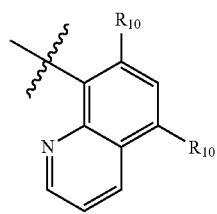
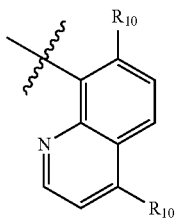
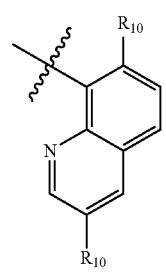
TABLE 4-continued
Formulas C₁₀ Hetero 1-283.
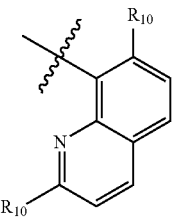
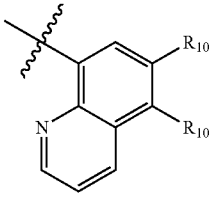
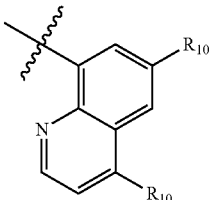
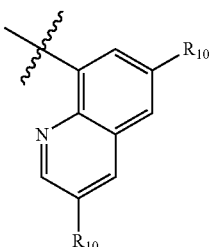
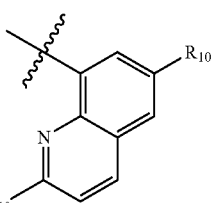
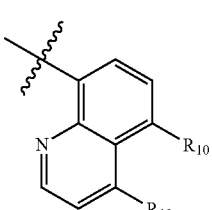
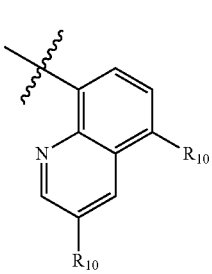

TABLE 4-continued
Formulas C₁₀ Hetero 1-283.
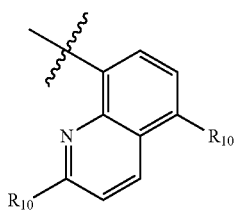
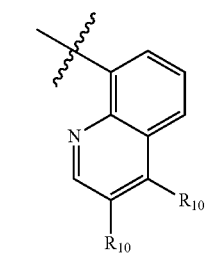
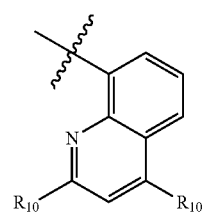
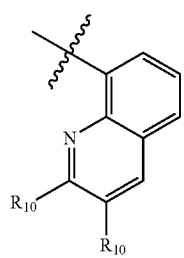
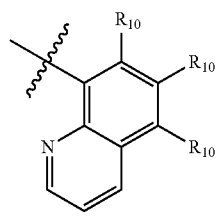
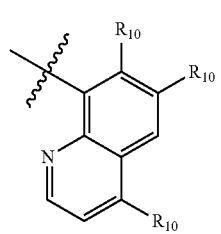
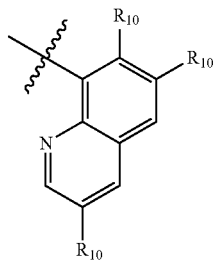
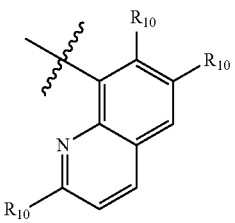
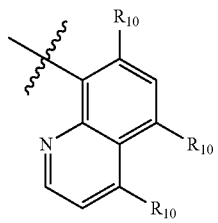
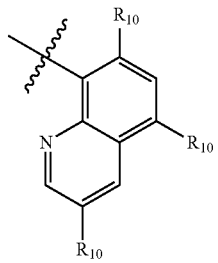
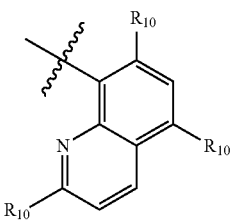
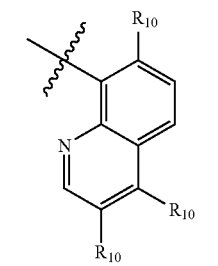

TABLE 4-continued

Formulas C₁₀ Hetero 1-283.

Aryl as napthyl with 1-3 groups attached are represented by the structures above. We describe with particularity and show the position of each and every substituent as taught herein where a phenyl, napthyl, C₆ or C₁₀ saturated or unsaturated ring or a pyridyl or a C₅ saturated ring may have 1, 2, or 3 hetero atoms with 1, 2, or 3 substituents are shown in the figures and Formula herein. In the Formula above when R is in the ring it is a hetero atom, $R_{het}$, otherwise R may be independently selected from —H, -halo, —CN, —OH, —OCH$_2$CH=CHCl, —C$_1$-C$_6$ alkyl, —O—C$_1$-C$_6$ alkyl, or —S—C$_1$-C$_6$ alkyl, also labeled $R_{10}$; and at each occurrence alkyl is optionally substituted with 1-5 halo, —CN, or —OH. While the structures above are shown as aromatic, it should be understood they also represent saturated ring systems. In the structures above N may also stand for $R_{het}$, or a heteroatom, preferably N and O, but also including S.

While the structures above are aromatic, it should be understood they also represent saturated ring systems. A saturated version of these compounds are also described and claimed.

It is important to recognize many heterocyclics are included in this invention. We describe compounds wherein up to 1, 2, or 3 of X, Z, and either $R_2$, or $R_3$ is independently a heterocyclic or alkylheterocyclic 5 or 6 member saturated or unsaturated optionally substituted ring, that is optionally substituted as above. While the hetero atom can be N, O or S in many instances heterocyclic has only one or two Ns, or an N and O, as in a morpholino, or just an O especially within a 5 member ring. Morpholino and furan examples are included. When a ring has 2 or more heteroatoms, we prefer they be non-adjacent and we provide as an example non-adjacent N and O.

Compounds may have the core moiety where one substituent, Z, X or $R_3$ or $R_2$ is heterocyclic and the other two aryl. Thus we describe compounds wherein one (1) of either X, Z, or either $R_2$, or $R_3$ is independently a heterocyclic or alkylheterocyclic 6 member saturated or unsaturated optionally substituted ring; wherein the hetero atom is N or O, wherein if X, Z, and either $R_2$, or $R_3$ is not heterocyclic then it is aliphatic or aryl, and the hetero atom is N or O. A compound wherein any one (1) of X, Z, and either $R_2$, or $R_3$ is optionally independently substituted with 1, 2 or 3 —H, -halo, —CN, —OH, —OCH$_2$CH=CHCl, —C$_1$-C$_6$ alkyl, —O—C$_1$-C$_6$ alkyl, or —S—C$_1$-C$_6$ alkyl; wherein at each occurrence, any —C$_1$-C$_6$ alkyl, is optionally independently substituted with 1-5-halo, —CN or —OH, and the hetero atom is N or O. A compound wherein any two (2) of X, Z, and either $R_2$, or $R_3$ is optionally independently substituted as above and the hetero atom is N or O. Descriptions are as follows: A compound wherein Z is -aryl, —C$_1$-C$_8$ alkylaryl, —C$_3$-C$_8$ cycloalkyl, or —C$_1$-C$_6$ alkylC$_6$cycloalkyl; X is heterocyclic or —C$_1$-C$_8$ alkylheterocyclic; when $R_2$ is —H or —C$_1$-C$_8$ alkyl, then $R_3$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$; when $R_3$ is —H or —C$_1$-C$_8$ alkyl, then $R_2$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$; Examples of compounds of this type are examples 8, 9, 12, 13, 15, 16, 22, 24, 26, 36, 40, 42, 45, 47, 49-51, 53-55, 56, and 59. Examples of pyrimidines are 47, 49, 56 and 59. The aryl may be phenyl. It may be for example that the Z substituent is heterocyclic and the others aliphatic or aryl as where Z is heterocyclic or —C$_1$-C$_8$ alkylheterocyclic, X is —H, —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, —NR$^i$R$^j$ or —C$_1$-C$_8$ alkylNR$^i$R$^j$; when $R_2$ is —H or —C$_1$-C$_8$ alkyl, then $R_3$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$; and when $R_3$ is —H or —C$_1$-C$_8$ alkyl, then $R_2$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$. It may be for example that the $R_2$ or $R_3$ substituent is heterocyclic and the others aliphatic or aryl as where Z is -aryl, —C$_1$-C$_8$ alkylaryl, —C$_3$-C$_8$ cycloalkyl, or —C$_3$-C$_8$ cycloalkyl; X is —H, —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, —NR$^i$R$^j$ or —C$_1$-C$_8$ alkylNR$^i$R$^j$; $R_2$ is —H or —C$_1$-C$_8$ alkyl, when $R_3$ is heterocyclic and —C$_1$-C$_8$ alkylheterocyclic; $R_3$ is —H or —C$_1$-C$_8$ alkyl, when $R_2$ is -heterocyclic and —C$_1$-C$_8$ alkylheterocyclic. In these examples of course aryl may be phenyl and —C$_1$-C$_8$ alkyl may be —C$_1$-C$_6$ alkyl or —C$_1$-C$_4$ alkyl.

Compounds may have the core moiety where 2 of the substituents Z X or $R_3$ or $R_2$ are heterocyclic and the other aryl. Descriptions are as follows: A compound wherein X is heterocyclic or —C$_1$-C$_8$ alkylheterocyclic; Z is heterocyclic, —C$_1$-C$_8$ alkylheterocyclic; when $R_2$ is —H or —C$_1$-C$_8$ alkyl, then $R_3$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$; and when $R_3$ is —H or —C$_1$-C$_8$ alkyl, then $R_2$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_9$ cycloalkyl and —C$_1$-C$_8$ alkylNR$^i$R$^j$. Compounds are described where Z is -aryl, —C$_1$-C$_8$ alkylaryl, —C$_3$-C$_8$ cycloalkyl, or —C$_3$-C$_8$ cycloalkyl; X is heterocyclic or —C$_1$-C$_8$ alkylheterocyclic; when $R_2$ is —H or —C$_1$-C$_8$ alkyl, then $R_3$ is heterocyclic and —C$_1$-C$_8$ alkylheterocyclic; and when $R_3$ is —H or —C$_1$-C$_8$ alkyl, then $R_2$ is -heterocyclic and —C$_1$-C$_8$ alkylheterocyclic. Compounds are described where Z is heterocyclic, —C$_1$-C$_8$ alkylheterocyclic; X is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, —NR$^i$R$^j$ or —C$_1$-C$_8$ alkylNR$^i$R$^j$; when $R_2$ is —H or —C$_1$-C$_8$ alkyl, then $R_3$ is heterocyclic and —C$_1$-C$_8$ alkylheterocyclic; and when $R_3$ is —H or —C$_1$-C$_8$ alkyl, then $R_2$ is -heterocyclic and —C$_1$-C$_8$ alkylheterocyclic. Compounds are described where 1, 2, or 3 of X, Z, and either $R_2$, or $R_3$ is independently a —C$_1$-C$_6$ cycloalkyl, —C$_1$-C$_6$ alkylC$_6$cycloalkyl, C$_6$ aryl, —C$_1$-C$_6$alkylC$_6$ aryl or C$_6$ heterocyclic or —C$_1$-C$_6$ alkylC$_6$- heterocyclic or saturated or unsaturated optionally substituted ring, wherein X, Z, and either $R_2$, or $R_3$ is optionally independently substituted with 1, 2 or 3, of —H, -halo, —CN, —OH, —OCH$_2$CH=CHCl, —C$_1$-C$_6$ alkyl, —O—C$_1$-C$_6$ alkyl, or —S—C$_1$-C$_6$ alkyl; wherein at each occurrence, any —C$_1$-C$_6$ alkyl, is optionally independently substituted with 1-5-halo, —CN or —OH. These compounds may of course have an aryl that is phenyl. Compounds may have the core moiety where two substituents are heterocyclic such as where one or two of X, Z, and either $R_2$, or $R_3$ are heterocyclic and none of the substituents are aliphatic or aryl, such as where Z is heterocyclic, —C$_1$-C$_8$ alkylheterocyclic, X, is —H, heterocyclic, —C$_1$-C$_8$ alkylheterocyclic, —NR$^i$R$^j$ or —C$_1$-C$_8$ alkylNR$^i$R$^j$;
when $R_2$ is —H or —C$_1$-C$_8$ alkyl then $R_3$ is heterocyclic, and —C$_1$-C$_8$ alkylheterocyclic; and
when $R_3$ is —H or —C$_1$-C$_8$ alkyl then $R_2$ is -heterocyclic, and —C$_1$-C$_8$ alkylheterocyclic.

Other combinations may also exist, for example where any 3 of X, Z, and either $R_2$, or $R_3$ is heterocyclic or —C$_1$-C$_6$ alkylheterocyclic 6 member saturated or unsaturated optionally substituted ring, wherein if X, Z, and either $R_2$, or $R_3$ is not heterocyclic then it is aliphatic or aryl, and the hetero atom is N or O. A compound wherein any 2 of X, Z, and either $R_2$, or $R_3$ is optionally independently substituted as above, and the hetero atom is N or O. A compound wherein any 1 of X, Z, and either $R_2$, or $R_3$ is optionally independently substituted as above and the hetero atom is N or O. Compounds are described where 1, 2, and 3 of X, Z, and either $R_2$, or $R_3$ is independently a heterocyclic or —C$_1$-C$_6$ alkylheterocyclic 6 member saturated or unsaturated optionally substituted ring, wherein X, Z, and either $R_2$, or $R_3$ is optionally independently substituted as above. In each instance aryl may be phenyl.

A compound wherein the halo substitutions may be attached to any carbon or as specified in any of the following $C_1$ alkyl or alkoxy with 1, 2 or 3 halo, —$C_1$ alkyl or alkoxy with 1, 2, or 3 halo, where the halo is Cl, Br or F, —$C_{1-2}$ alkyl or alkoxy with 1-5 halo where the halo is Cl, Br or F, —$C_{1-2}$ alkyl or alkoxy with 1-5 halo where the halo is F or Cl, —$C_{1-2}$ alkyl or alkoxy with 1-5 halo where the halo is Br, —$C_{1-2}$ alkyl or alkoxy with 1-5 halo where the halo is Cl, —$C_{1-2}$ alkyl or alkoxy with 1-5 halo where the halo is F, —$C_{1-2}$ alkyl or alkoxy with 1-4 halo where the halo is any combination of Br, F or Cl, —$C_{1-2}$ alkyl or alkoxy with 1-4 halo where the halo is any combination of F or Cl, —$C_{1-2}$ alkyl or alkoxy with 4 halo where the halo is 3 Cl and F, —$C_{1-2}$ alkyl or alkoxy with 4 halo where the halo is Cl and 3F, —$C_{1-2}$ alkyl or alkoxy with 4 halo where the halo is 2 Cl and 2F, —$C_{1-3}$ alkyl or alkoxy with 1-6 halo where the halo is any combination of Cl, Br or F, —$C_{1-3}$ alkyl or alkoxy with 1-6 halo where the halo is any combination of F or Cl, —$C_{1-3}$ alkyl or alkoxy with 1-6 halo where the halo is 1-3 Cl and 1-3 F, —$C_{1-3}$ alkyl or alkoxy with 2-4 halo wherein the halo is 1-3 F with 1 Cl, —$C_{1-3}$ alkyl or alkoxy with 2-4 halo wherein the halo is 1 F with 1-3 Cl, —$C_{1-3}$ alkyl or alkoxy with 1-5 halo where the halo is F or Cl, —$C_{1-3}$ alkyl or alkoxy with 1-4 halo where the halo is any combination of F or Cl, —$C_{1-3}$ alkyl or alkoxy with 1-4 halo where the halo is 1-3 F with 1 Cl, —$C_{1-3}$ alkyl or alkoxy with 1-4 halo where the halo is 1 F with 1-3 Cl, —$C_{1-3}$ alkyl or alkoxy with 1-2 halo where the halo is Cl and or F, —$C_{1-4}$ alkyl or alkoxy with 1-6 halo where the halo is Cl, Br or F, —$C_{1-4}$ alkyl or alkoxy with 1-6 halo where the halo is F or Cl, —$C_{1-4}$ alkyl or alkoxy with 1-3 halo where the halo is Br, —$C_{1-4}$ alkyl or alkoxy with 1-6 halo where the halo is Cl, —$C_{1-4}$ alkyl or alkoxy with 1-6 halo where the halo is F, —$C_{1-4}$ alkyl or alkoxy with 1-6 halo where the halo is 1-3 Cl and 1-3 F, —$C_{1-4}$ alkyl or alkoxy with 2-4 halo wherein the halo is 1-3 F with 1 Cl, —$C_{1-4}$ alkyl or alkoxy with 2-4 halo wherein the halo is 1 F with 1-3 Cl, —$C_{1-4}$ alkyl or alkoxy with 1-5 halo where the halo is F or Cl, —$C_{1-4}$ alkyl or alkoxy with 1-4 halo where the halo is F or Cl, —$C_{1-4}$ alkyl or alkoxy with 1-4 halo where the halo is 1-3 F with 1 Cl, —$C_{1-4}$ alkyl or alkoxy with 1-4 halo where the halo is 1 F with 1-3 Cl, —$C_{1-4}$ alkyl or alkoxy with 1-2 halo where the halo is Cl and or F, —$C_{1-5}$ alkyl or alkoxy with 1-6 halo where the halo is Cl, Br or F, —$C_{1-5}$ alkyl or alkoxy with 1-6 halo where the halo is F or Cl, —$C_{1-5}$ alkyl or alkoxy with 1-3halo where the halo is Br, —$C_{1-5}$ alkyl or alkoxy with 1-6 halo where the halo is Cl, —$C_{1-5}$ alkyl or alkoxy with 1-6 halo where the halo is F, —$C_{1-5}$ with 1-6 halo where the halo is 1-3 Cl and 1-3 F, —$C_{1-5}$ alkyl or alkoxy with 2-4 halo wherein the halo is 1-3 F with 1 Cl, —$C_{1-5}$ alkyl or alkoxy with 2-4 halo wherein the halo is 1 F with 1-3 Cl, —$C_{1-4}$ alkyl or alkoxy with 1-5 halo where the halo is F or Cl, —$C_{1-5}$ alkyl or alkoxy with 1-4 halo where the halo is F or Cl, —$C_{1-5}$ alkyl or alkoxy with 1-4 halo where the halo is 1-3 F with 1 Cl, —$C_{1-5}$ with 1-4 halo where the halo is 1 F with 1-3 Cl, —$C_{1-5}$ alkyl or alkoxy with 1-2 halo where the halo is Cl and or F, —$C_{1-6}$ alkyl or alkoxy with 1-6 halo where the halo is Cl, Br or F, —$C_{1-6}$ alkyl or alkoxy with 1-6 halo where the halo is F or Cl, —$C_{1-6}$ alkyl or alkoxy with 1-3halo where the halo is Br, —$C_{1-6}$ alkyl or alkoxy with 1-6 halo where the halo is Cl, —$C_{1-6}$ alkyl or alkoxy with 1-6 halo where the halo is F, —$C_{1-6}$ alkyl or alkoxy with 1-6 halo where the halo is 1-3 Cl and 1-3 F, —$C_{1-6}$ alkyl or alkoxy with 2-4 halo wherein the halo is 1-3 F with 1 Cl, —$C_{1-6}$ alkyl or alkoxy with 2-4 halo wherein the halo is 1 F with 1-3 Cl, —$C_{1-4}$ alkyl or alkoxy with 1-5 halo where the halo is F or Cl, —$C_{1-6}$ alkyl or alkoxy with 1-4 halo where the halo is F or Cl, —$C_{1-6}$ alkyl or alkoxy with 1-4 halo where the halo is 1-3 F with 1 Cl, —$C_{1-6}$ alkyl or alkoxy with 1-4 halo where the halo is 1 F with 1-3 Cl, —$C_{1-6}$ alkyl or alkoxy with 1-2 halo where the halo is Cl and or F.

We describe in detail halo alkyl and alkoxyhalo. Compounds wherein the I, F, Cl, or Br substitutions are selected from and may be substitued for any of the specific halogens described here: —$CH_2F$, —$CHF_2$, —$CF_3$, —$CH_2CH_2F$, —$CHFCH_2F$, —$CH_2CHF_2$, —$CF_2CH_3$, —$CH_2CF_3$, —$CH_2CH_2CH_2F$, —$CHFCH_2CH_3$, —$CH_2CHFCH_3$, —$CH_2CH_2CHF_2$, —$CHFCH_2CH_2F$, —$CF_2CH_2CH_3$, —$CH_2CHFCH_2F$, —$CH_2CH_2CF_3$, —$CH_2CHFCHF_2$, —$CHFCH_2CHF_2$, —$CH_2CF_2CH_2F$, —$CHFCF_2CH_3$, —$CF_2CHFCH_3$, —$CH_2CHFCF_3$, —$CHFCH_2CF_3$, —$CF_2CHFCH_2F$, —$CH_2CF_2CHF_2$, —$CF_2CH_2CF_3$, —$CH_2Cl$, —$CHCl_2$, —$CCl_3$, —$CH_2CH_2Cl$, —$CHClCH_2Cl$, —$CH_2CHCl_2$, —$CCl_2CH_3$, —$CH_2CCl_3$, —$CH_2CH_2CH_2Cl$, —$CHClCH_2CH_3$, —$CH_2CHClCH_3$, —$CH_2CH_2CHCl_2$, —$CHClCH_2CH_2Cl$, —$CH_2CHClCH_2Cl$, —$CH_2CH_2CCl_3$, —$CH_2CHClCHCl_2$, —$CHClCH_2CHCl_2$, —CHClCHClCHCl_2, —CHClCHClCH_2Cl, —CCl_2CHClCH_3, —$CH_2CHClCCl_3$, —$CHClCH_2CCl_3$, —$CH_2CCl_2CHCl_2$, —$CCl_2CH_2CHCl_2$, —$CCl_2CCl_2CH_3$, —CHClF, —CClF_2, —$CCl_2F$, —$CHClCH_2F$, —$CCl_2CH_2F$, —$CF_2CH_2Cl$, —$CHClCHF_2$, —$CHFCHCl_2$, —$CCl_2CHF_2$— $CH_2CH_2CClF_2$, —$CH_2CH_2CFCl_2$, —$CH_2CHFCHClF$, —$CH_2CHClCHClF$, —$CH_2CF_2CH_2Cl$, —$CH_2CCl_2CH_2F$, —$CF_2CHClCH_3$, —$CF_2CH_2CH_2Cl$, —$CHFCHClCHF_2$, —$CHFCHClCHCl_2$, —$CF_2CHClCHF_2$, —$CF_2CCl_2CH_3$, —$CCl_2CF_2CH_3$, —$CF_2CHFCH_2Cl$, —$CCl_2CHFCH_2F$, —$CHClCHFCHF_2$, —$CHClCHClCHF_2$, —$CF_2CH_2CHCl_2$, —$CF_2CHClCH_2Cl$, —$CH_2CCl_2CHFCl$, —$CH_2CF_2CHFCl$, —$CH_2CF_2CCl_3$, —$CHFCFCCl_3$, —$CF_2CH_2CCl_3$— $CH_2CClFCF_3$, —$CH_2CCl_2CF_3$, —$CCl_2CH_2CF_3$, —$CHClCHClCF_3$, —O—$CH_2F$, —O—$CHF_2$, —O—$CF_3$, —O—$CH_2CH_2F$, —O—$CHFCH_2F$, —O—$CH_2CHF_2$, —O—$CF_2CH_3$, —O—$CH_2CF_3$, —O—$CH_2CH_2CH_2F$, —O—$CHFCH_2CH_3$, —O—$CH_2CHFCH_3$, —O—$CH_2CH_2CHF_2$, —O—$CHFCH_2CH_2F$, —O—$CF_2CH_2CH_3$, —O—$CH_2CHFCH_2F$, —O—$CH_2CH_2CF_3$, —O—$CH_2CHFCHF_2$, —O—$CHFCH_2CHF_2$, —O—$CH_2CF_2CH_2F$, —O—$CHFCF_2CH_3$, —O—$CF_2CHFCH_3$, —O—$CH_2CHFCF_3$, —O—$CHFCH_2CF_3$, —O—$CF_2CHFCH_2F$—O—$CH_2CF_2CHF_2$, —O—$CF_2CH_2CF_3$, —O—$CH_2Cl$, —O—$CHCl_2$, —O—$CCl_3$, —O—$CH_2CH_2Cl$, —O—$CHClCH_2Cl$, —O—$CH_2CHCl_2$-O—$CCl_2CH_3$, —O—$CH_2CCl_3$, —O—$CH_2CH_2CH_2Cl$, —O—$CHClCH_2CH_3$, —O—$CH_2CHClCH_3$, —O—$CH_2CH_2CHCl_2$, —O—$CHClCH_2CH_2Cl$, —O—$CH_2CHClCH_2Cl$, —O—$CH_2CH_2CCl_3$, —O—$CH_2CHClCHCl_2$, —O—$CHClCH_2CHCl_2$, —O—CHClCHClCHCl_2, —O—CHClCHClCH_2Cl, —O—CCl_2CHClCH_3, —O—$CH_2CHClCCl_3$, —O—$CHClCH_2CCl_3$, —O—$CH_2CCl_2CHCl_2$, —O—$CCl_2CH_2CHCl_2$, —O—$CCl_2CCl_2CH_3$, —O—CHClF, —O—CClF_2, —O—$CCl_2F$, —O—$CHClCH_2F$, —O—$CCl_2CH_2F$, —$CF_2CH_2Cl$, —$CHClCHF_2$, —O—$CHFCHCl_2$, —O—$CCl_2CHF_2$—O—$CH_2CH_2CClF_2$, —O—$CH_2CH_2CFCl_2$, —O—$CH_2CHFCHClF$, —O—$H_2CHClCHClF$, —O—$CH_2CF_2CH_2Cl$, —O—$CH_2CCl_2CH_2F$, —O—$CF_2CHClCH_3$, —O—$CF_2CH_2CH_2Cl$, —O—$CHFCHClCHF_2$, —O—$CHFCHClCHCl_2$, —O—$CF_2CHClCHF_2$, —O—$CF_2CCl_2CH_3$, —O—$CCl_2CF_2CH_3$, —O—$CF_2CHFCH_2Cl$, —O—$CCl_2CHFCH_2F$, —O—$CHClCHFCHF_2$, —O—$CHClCHClCHF_2$, —O—CF$_2$CH$_2$CHCl$_2$, —O—CF$_2$CHClCH$_2$Cl, —O—CH$_2$CCl$_2$CHFCl, —O—CH$_2$CF$_2$CHFCl, —O—CHcCF$_2$CCl$_3$, —O—CHFCF$_2$CCl$_3$, —O—CF$_2$CH$_2$CCl$_3$—O—CH$_2$CClFCF$_3$, —O—CH$_2$CCl$_2$CF$_3$, —O—CCl$_2$CH$_2$CF$_3$, —O—CHClCHClCF$_3$.

All of the compounds described as triazines can also be described made as pyrimidines, thus reference is made to the descriptions above wherein Y is CR$_1$ and Formula I is replaced with Formulas II, II-CR1, III, III-CR1 and IV, IV-CR1, as described below.

Formula II and Formula II-CR1

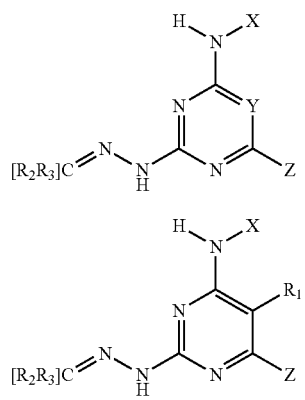

Formula III and Formula III-CR1

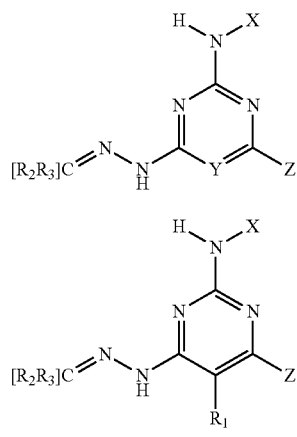

Formula IV and Formula IV-CR1

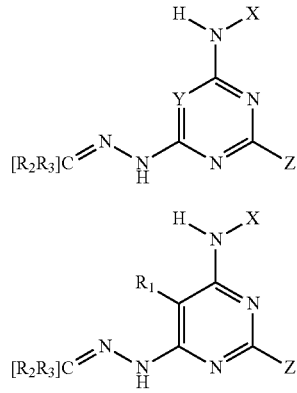

We note with particularity the following compounds and type of compounds that are described and we provide many examples.

Examples of Formula IV can be found in example 46. Example 58 shows a compound of Formula III. Numerous examples are provided where the X substituent is heterocyclic attached to a compound described by Formula II, such as examples 47, 49, 56 and 59. Procedures to make these compounds are described above. Once made with the procedures described, it will be known to one skilled in the art how to make any of the substituents from the triazines and place them on any compound and in any position on the pyrimidines as shown in Formulas II, III and IV. These moieties and specific descriptions are also provided in the Table below where each group, Z, X and R2 and R3 is described as being able to be used in any other position, using the procedures described herein.

We thus specifically describe and provide examples where: X is —C$_1$-C$_6$ alkyl, phenyl, arylalkyl and heterocyclicalkyl, and N-bisalkyl. The aryl and heterocyclic rings may be substituted with one to five substituents selected from the group consisting of hydrogen, halo, CN, OCH$_2$CH=CHCl, C$_1$-C$_6$ alkyl (optional halo, —OH, —CN), C$_1$-C$_6$ alkoxy (optional halo, —OH, —CN) and C$_1$-C$_6$ thioalkyl (optional halo, —OH, —CN). Y is CR$_1$ or N. Z is aryl, phenyl or heterocyclic. The aryl and heterocyclic rings may be substituted with one to five independent substituents selected from above. R$_1$ is H, halo, and C$_1$-C$_4$ (halo optional) alkyl. R$_2$ and R$_3$ independently represent H, C$_1$-C$_6$ alkyl, aryl and heterocyclic. The alkyl substituents may be substituted with one to five halos. The aryl and heterocyclic rings may be substituted with one to five independent substituents selected from the group above. We specifically identify the following: A compound according wherein Z is a substituted aryl ring. A compound wherein X is a substituted aryl or pyridyl ring. A compound wherein R$_2$ is H and R$_3$ is a substituted aryl ring. A compound wherein X is a substituted aryl or pyridyl ring. A compound wherein R$_2$ is H and R$_3$ is a substituted aryl ring. A compound wherein the Formula (I) heteroaromatic ring substituents have the positions shown in Formula II, III, and IV, shown above. A compound wherein Z is a substituted phenyl ring. A compound wherein X is a substituted phenyl or pyridyl ring. A compound wherein R$_2$ is H and R$_3$ is a substituted aryl ring. A compound wherein Y is N and X is a substituted phenyl or pyridyl ring. A compound wherein R$_2$ is H and R$_3$ is a substituted aryl ring. A compound wherein Y is N. A compound wherein Y is N and Z is a substituted phenyl ring. A compound wherein R$_2$ is H and R$_3$ is a substituted aryl ring. A compound wherein R$_2$ is a substituted aryl ring and H is R$_3$. A compound wherein X is a substituted phenyl or pyridyl ring and R$_2$ is H and R$_3$ is a substituted aryl ring. A compound wherein X is a substituted phenyl or pyridyl ring and R$_2$ is a substituted aryl ring and R$_3$ is H. A compound wherein X is a substituted phenyl or pyridyl ring. A compound wherein Z is a substituted phenyl ring, R$_2$ is H and R$_3$ is a substituted phenyl ring. A compound wherein Z is an ortho-halo substituted phenyl ring. A compound wherein R$_2$ or R$_3$ is a para-haloalkoxy substituted aryl ring. Any of these variables and combinations may be made with other variables or combinations to provide various scopes or sizes of groups of claimed compounds.

A composition for controlling insects which comprises any of the compounds described herein and a phytologically-acceptable carrier.

A process for the preparation of a compound of Formula (I) comprising:

(a) contacting cyanuric chloride (Formula V), a 2,4,6-trichloropyrimidine (Formula VI) or 2,4,6-trihalopyrimidine (Formula VI) wherein Hal is independently Cl or F.

V

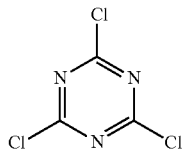

VI

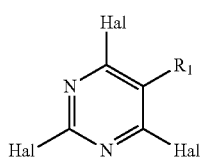

with an organometallic shown in Formula VII

Z-M              Formula VII wherein:
M=Li, Mg, B, Zn in a polar aprotic solvent to provide aryl and heterocyclic substituted triazines and pyrimidines of the Formulas VIII-X.

VIII

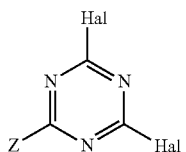

IX

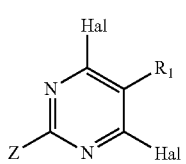

X

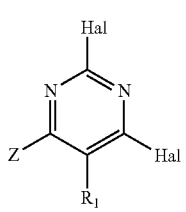

(b) contacting a compound of Formulas VIII, IX, X with a primary amino nucleophile (X—NH$_2$) in a polar aprotic solvent in the presence of a base to provide a compound of the Formula XI, XV, XIII, XII:

XI

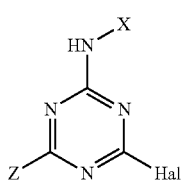

XV

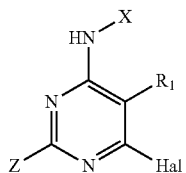

XIII

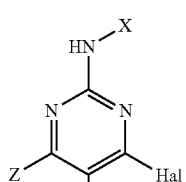

XII

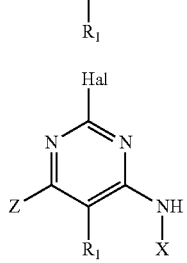

(c) contacting compounds of Formulas XI, XV, XIII, XII with hydrazine in a polar aprotic solvent to provide hydrazine compounds which were then added to keto compounds to make compounds of Formula I where Y is N or CR$_1$, as described above.

Formula I

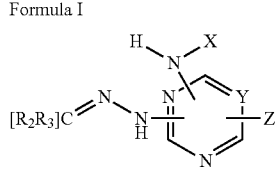

The compounds below are described, either by themselves or in any combination of more than one, and as grouped with any generic description provided herein, where the compounds are selected from:

N-(4-chlorophenyl)-4-(2,6-difluorophenyl)-6-(2-(4-(trifluoromethoxy)benzylidene)hydrazinyl)-1,3,5-triazin-2-amine; N-(4-chlorophenyl)-4-phenyl-6-(2-(4-(trifluoromethoxy)benzylidene)hydrazinyl)-1,3,5-triazin-2-amine; 4-(2-chloro-6-fluorophenyl)-N-(4-chlorophenyl)-6-(2-(4-(trifluoromethoxy)benzylidene)hydrazinyl)-1,3,5-triazin-2-amine; N-((6-chloropyridin-3-yl)methyl)-4-(2,6-difluorophenyl)-6-(2-(4-(trifluoromethoxy)benzylidene)hydrazinyl)-1,3,5-triazin-2-amine; N-(6-chloropyridin-3-yl)-4-(2,6-difluorophenyl)-6-(2-(4-(trifluoromethoxy)benzylidene)hydrazinyl)-1,3,5-triazin-2-amine; N-(4-chlorophenyl)-4-(2,6-difluorophenyl)-6-(2-(4-(1,1,2,2-tetrafluoroethoxy)benzylidene)hydrazinyl)-1,3,5-triazin-2-amine; 4-(2-chloro-6-fluorophenyl)-N-(4-chlorophenyl)-6-(2-(4-(1,1,2,2-tetrafluoroethoxy)benzylidene)hydrazinyl)-1,3,5-triazin-2-amine; 4-(2-chloro-6-fluorophenyl)-N-(6-chloropyridin-3-yl)-6-(2-(4-(1,1,2,2-tetrafluoroethoxy)benzylidene)hydrazinyl)-1,3,5-triazin-2-amine; 4-(2-chloro-6-fluorophenyl)-N-(6-chloropyridin-3-yl)-6-(2-(4-(trifluoromethoxy)benzylidene)hydrazinyl)-1,3,5-triazin- 2-amine; N-(6-chloropyridin-3-yl)-4-(2,6-difluorophenyl)-6-(2-(4-(1,1,2,2-tetrafluoroethoxy)benzylidene)hydrazinyl)-1,3,5-triazin-2-amine; N-(6-chloropyridin-3-yl)-4-(2,6-dichlorophenyl)-6-(2-(4-(trifluoromethoxy)benzylidene)hydrazinyl)-1,3,5-triazin-2-amine; 4-(2-chloro-6-fluorophenyl)-N-(4-chlorophenyl)-6-(2-(4-ethylbenzylidene)hydrazinyl)-1,3,5-triazin-2-amine; 4-((2-(4-(2-chloro-6-fluorophenyl)-6-((4-chlorophenyl)amino)-1,3,5-triazin-2-yl)hydrazono)methyl)benzonitrile; 4-(2-butylidenehydrazinyl)-6-(2-chloro-6-fluorophenyl)-N-(4-chlorophenyl)-1,3,5-triazin-2-amine; 4-(2-chloro-6-fluorophenyl)-N-(4-chlorophenyl)-6-(2-(2-phenylethylidene)hydrazinyl)-1,3,5-triazin-2-amine; 4-(2-chloro-6-fluorophenyl)-N-(4-chlorophenyl)-6-(2-(1-(4-(trifluoromethoxy)phenyl)ethylidene)hydrazinyl)-1,3,5-triazin-2-amine; 4-(2-chloro-6-fluorophenyl)-N-((6-chloropyridin-3-yl)methyl)-6-(2-(4-(trifluoromethoxy)benzylidene)hydrazinyl)-1,3,5-triazin-2-amine; 4-(2-chloro-6-fluorophenyl)-N-(p-tolyl)-6-(2-(4-(trifluoromethoxy)benzylidene)hydrazinyl)-1,3,5-triazin-2-amine; 4-(2-chloro-6-fluorophenyl)-N-(2-morpholinoethyl)-6-(2-(4-(trifluoromethoxy)benzylidene)hydrazinyl)-1,3,5-triazin-2-amine; 2-(2-chloro-6-fluorophenyl)-4-(2,2-dimethylhydrazinyl)-6-(2-(4-(trifluoromethoxy)benzylidene)hydrazinyl)-1,3,5-triazine; N-(3-chloro-4-fluorophenyl)-4-(2-chloro-6-fluorophenyl)-6-(2-(4-(trifluoromethoxy)benzylidene)hydrazinyl)-1,3,5-triazin-2-amine; 4-(2-chloro-6-fluorophenyl)-N-(4-fluoro-3-(trifluoromethyl)phenyl)-6-(2-(4-(trifluoromethoxy)benzylidene)hydrazinyl)-1,3,5-triazin-2-amine; 4-(2-(4-(2-chloro-1,1,2-trifluoroethoxy)benzylidene)hydrazinyl)-6-(2-chloro-6-fluorophenyl)-N-(6-chloropyridin-3-yl)-1,3,5-triazin-2-amine; 4-(2-(4-(2-chloro-1,1,2-trifluoroethoxy)benzylidene)hydrazinyl)-6-(2-chloro-6-fluorophenyl)-N-(4-chlorophenyl)-1,3,5-triazin-2-amine; 4-(2-chloro-6-fluorophenyl)-N-(3,4-dichlorophenyl)-6-(2-(4-(trifluoromethoxy)benzylidene)hydrazinyl)-1,3,5-triazin-2-amine; 4-(2-chloro-6-fluorophenyl)-N-(3,5-dichlorophenyl)-6-(2-(4-(trifluoromethoxy)benzylidene)hydrazinyl)-1,3,5-triazin-2-amine; 4-(2-chloro-6-fluorophenyl)-N-(2-chlorophenyl)-6-(2-(4-(trifluoromethoxy)benzylidene)hydrazinyl)-1,3,5-triazin-2-amine; N-(6-chloropyridin-3-yl)-4-(2-fluorophenyl)-6-(2-(4-(trifluoromethoxy)benzylidene)hydrazinyl)-1,3,5-triazin-2-amine; 4-(2-chloro-6-fluorophenyl)-N-methyl-6-(2-(4-(trifluoromethoxy)benzylidene)hydrazinyl)-1,3,5-triazin-2-amine; N-(4-chlorophenyl)-4-(2-fluorophenyl)-6-(2-(4-(trifluoromethoxy)benzylidene)hydrazinyl)-1,3,5-triazin-2-amine; N-(4-chlorophenyl)-2-phenyl-6-(2-(4-(trifluoromethoxy)benzylidene)hydrazinyl)pyrimidin-4-amine; 4-(2-(2-chloro-6-fluorobenzylidene)hydrazinyl)-N-(4-chlorophenyl)-6-(4-(trifluoromethoxy)phenyl)-1,3,5-triazin-2-amine; 4-(2-chloro-6-fluorophenyl)-N-(6-chloropyridin-3-yl)-6-(2-(4-(trifluoromethyl)benzylidene)hydrazinyl)-1,3,5-triazin-2-amine; 6-(2-chloro-6-fluorophenyl)-N-(4-chlorophenyl)-2-(2-(4-(trifluoromethoxy)benzylidene)hydrazinyl)pyrimidin-4-amine; 4-(2-chloro-6-fluorophenyl)-N-(6-chloropyridin-3-yl)-6-(2-(4-methylbenzylidene)hydrazinyl)-1,3,5-triazin-2-amine; 4-(2-chloro-6-fluorophenyl)-N-(6-chloropyridin-3-yl)-6-(2-(4-methoxybenzylidene)hydrazinyl)-1,3,5-triazin-2-amine; 4-(2-chloro-6-fluorophenyl)-N-(6-chloropyridin-3-yl)-6-(2-(3-fluoro-4-(trifluoromethyl)benzylidene)hydrazinyl)-1,3,5-triazin-2-amine; N-((6-chloropyridin-3-yl)methyl)-6-phenyl-2-(2-(4-(trifluoromethoxy)benzylidene)hydrazinyl)pyrimidin-4-amine; N-(4-chlorophenyl)-6-phenyl-2-(2-(4-(trifluoromethoxy)benzylidene)hydrazinyl)pyrimidin-4-amine; N-(4-chlorophenyl)-4-phenyl-6-(2-(4-(trifluoromethoxy)benzylidene)hydrazinyl)pyrimidin-2-amine; 6-(2-chloro-6-fluorophenyl)-N-(6-chloropyridin-3-yl)-2-(2-(4-(trifluoromethoxy)benzylidene)hydrazinyl)pyrimidin-4-amine; 4-(2-chloro-6-fluorophenyl)-N-(4-chlorobenzyl)-6-(2-(4-(trifluoromethoxy)benzylidene)hydrazinyl)-1,3,5-triazin-2-amine; N-(4-chlorobenzyl)-6-phenyl-2-(2-(4-(trifluoromethoxy)benzylidene)hydrazinyl)pyrimidin-4-amine; N-(4-chlorophenyl)-4-(2,6-dichlorophenyl)-6-(2-(4-(trifluoromethoxy)benzylidene)hydrazinyl)-1,3,5-triazin-2-amine; N-(4-chlorophenyl)-4-(3-fluorophenyl)-6-(2-(4-(trifluoromethoxy)benzylidene)hydrazinyl)-1,3,5-triazin-2-amine; N-(4-chlorophenyl)-4-(2-(4-(trifluoromethoxy)benzylidene)hydrazinyl)-6-(4-(trifluoromethoxy)phenyl)-1,3,5-triazin-2-amine; 4-(2,6-difluorophenyl)-N-(4-fluoro-3-(trifluoromethyl)phenyl)-6-(2-(4-(trifluoromethoxy)benzylidene)hydrazinyl)-1,3,5-triazin-2-amine; 4-(2,6-difluorophenyl)-6-(2-(4-(trifluoromethoxy)benzylidene)hydrazinyl)-N-(4-(trifluoromethoxy)phenyl)-1,3,5-triazin-2-amine; 4-(2-chloro-6-fluorophenyl)-N-(2-chloropyridin-4-yl)-6-(2-(4-(trifluoromethoxy)benzylidene)hydrazinyl)-1,3,5-triazin-2-amine; 4-(2-chloro-6-fluorophenyl)-N-(5-chloropyridin-2-yl)-6-(2-(4-(trifluoromethoxy)benzylidene)hydrazinyl)-1,3,5-triazin-2-amine.

This document will sometimes refer to the variables $R_1$, $R_2$, $R_3$, Z and X as "pendant groups." Pendant groups are chemical moieties attached to the core moiety. Sometime pendant groups are attached to the core moiety at preferred pendant positions, as are shown in Formula XVI, II, III, and IV. Tables of various pendant groups, both specific and generic are provided herein, see Tables 1, 2, 3, 4, 5, 6 and 7. Table 7 shows the actual pendant groups as they are positioned on the examples with data. Table 5 shows the pendant groups from the examples with data and it should be understood that each group can be used at different positions as different substituents on the core moiety. Table 6 provides notional examples of compounds that can be made using the procedures described herein and the skill of one of ordinary skill in the art. They are expected to be highly active. The Table 6 pendant groups are shown in their preferred positions but they could be used in combination with any of the other pendant groups from any of Tables 1-5, at any position and preferably at the pendant positions. The compounds of the invention can be made with any pendant group, positioned at any pendant group position. Applicants' have discovered that the activity of these compounds increases if the X and the $R_2$ or $R_3$ pendant groups have substituents at the para position. In addition, Applicants' have discovered that substitutions on the Z pendant group position are more active when the Z group has ortho substituents. Many examples of this can be found, e.g. Examples 1, 4, 8-13 and others. Surprisingly we have also found that high levels of activity can be generated in a compound when an active "para position substituent" like the one in Example r at position $R_2/R_3$ is moved to the "Z position" and the "ortho position substituent" at the Z position in Example r is moved to the $R_2/R_3$ position. An example of this phenomena of high value moiety transference of high activity can be found in Example 48. Both Examples 4 and 48 have "A" levels of activity. Example 4 has a $R_2/R_3$ pendant group substituted at the para position and a Z pendant group substituted at the ortho position. Example 4 is highly active and yet when Z is given the para-trifluoromethoxy phenyl substituent and R₂/R₃ is given the ortho di halo phenyl substituent, as in Example 48, then Example 48 also displays high levels of activity.

The following Table 5 is provided to further describe the compounds of the invention and to show and disclose how the substituents Z, X and R₂ and R₃ may be replaced various groups and by one another. The variables are taken from the substituents on the compounds in Table 8. Table 5 shows the substituents from the compounds shown in Table 8 in the same order as the compounds are presented in Table 8.

TABLE 5

| R₂/R₃ | X | Z |
|---|---|---|
| 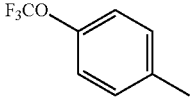 | 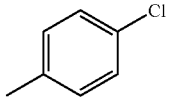 | 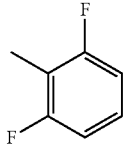 |
| 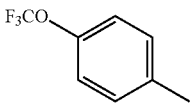 | 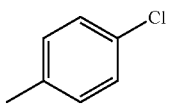 | 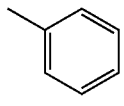 |
| 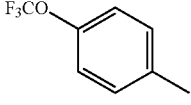 | 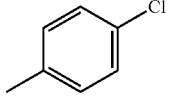 | 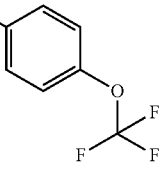 |
| 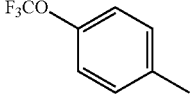 | 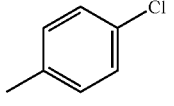 | 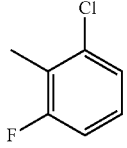 |
| 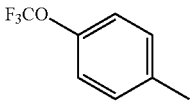 | 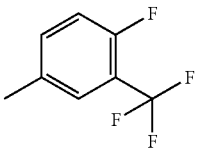 | 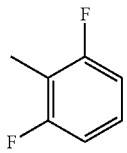 |
| 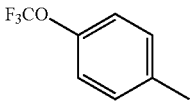 | 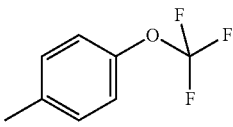 | 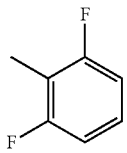 |
| 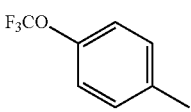 | 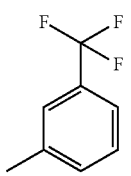 | 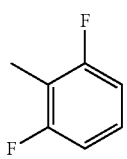 |
| 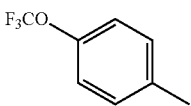 | 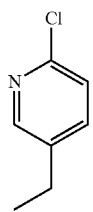 | 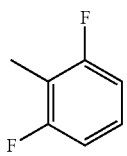 |

TABLE 5-continued

| R₂/R₃ | X | Z |
|---|---|---|

TABLE 5-continued

| R₂/R₃ | X | Z |
|---|---|---|
| 4-cyanobenzyl | 4-chlorobenzyl | 2-chloro-6-fluoro-phenyl |
| n-butyl | 4-chlorobenzyl | 2-chloro-6-fluoro-phenyl |
| benzyl | 4-chlorobenzyl | 2-chloro-6-fluoro-phenyl |
| 4-(trifluoromethoxy)benzyl and —CH₃ | 4-chlorobenzyl | 2-chloro-6-fluoro-phenyl |
| 4-(trifluoromethoxy)benzyl | (2-chloropyridin-5-yl)ethyl | 2-chloro-6-fluoro-phenyl |
| 4-(trifluoromethoxy)benzyl | 4-methylbenzyl | 2-chloro-6-fluoro-phenyl |
| 4-(trifluoromethoxy)benzyl | 3-morpholinopropyl | 2-chloro-6-fluoro-phenyl |
| 4-(trifluoromethoxy)benzyl | N,N-dimethylaminoethyl | 2-chloro-6-fluoro-phenyl |
| 4-(trifluoromethoxy)benzyl | (tetrahydrofuran-3-yl)methyl | 2-chloro-6-fluoro-phenyl |

TABLE 5-continued

TABLE 5-continued

TABLE 5-continued
| R$_2$/R$_3$ | X | Z |
|---|---|---|
| 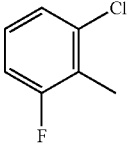 | 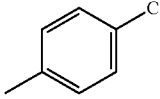 | 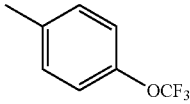 |
| 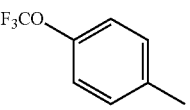 | 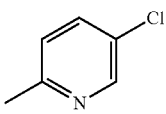 | 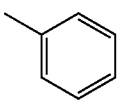 |
| 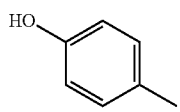 | 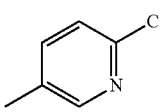 | 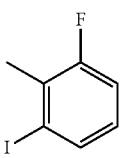 |
| 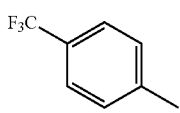 | 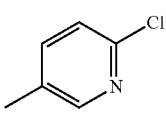 | 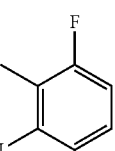 |
| 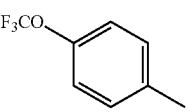 | 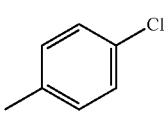 | 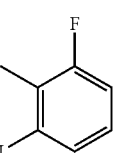 |
| 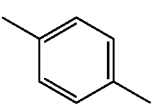 | 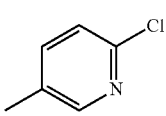 | 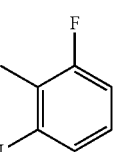 |
| 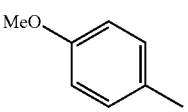 | 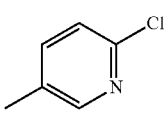 | 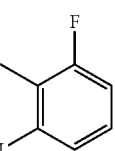 |
| 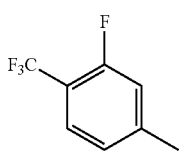 | 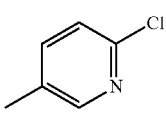 | 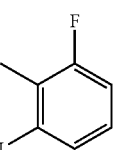 |
| 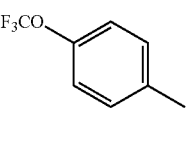 | 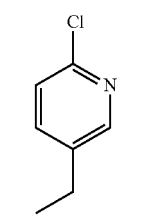 | 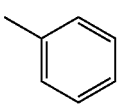 |
| 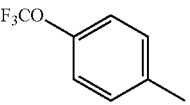 | 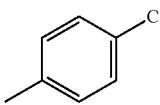 | |

TABLE 5-continued

| R₂/R₃ | X | Z |
|---|---|---|
| 4-(F₃CO)-phenyl | 4-Cl-phenyl | phenyl |
| 4-(F₃CO)-phenyl | 2-Cl-5-pyridyl | 2-F-6-Cl-phenyl |
| 4-(F₃CO)-phenyl | 4-Cl-benzyl | 2-F-6-Cl-phenyl |
| 4-(F₃CO)-phenyl | 4-Cl-benzyl | phenyl |

TABLE 6

| | R₂/R₃ | X | Z |
|---|---|---|---|
| 1 | Any | Any | 3-Cl-pyridin-2-yl |
| 2 | Any | Any | 4-Cl-pyridin-2-yl |
| 3 | Any | Any | 3-F-pyridin-2-yl |
| 4 | Any | Any | 4-F-pyridin-2-yl |
| 5 | Any | Any | 3,5-diF-pyridin-2-yl |
| 6 | Any | Any | 4-CH₃-pyridin-2-yl |
| 7 | Any | Any | 3-CH₃-pyridin-2-yl |
| 8 | Any | Any | 3,4-diCH₃-pyridin-2-yl |

TABLE 6-continued
| | R₂/R₃ | X | Z |
|---|---|---|---|
| 9 | Any | Any | 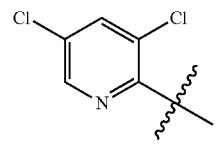 [SMILES: *c1ncc(Cl)cc1Cl] |
| 10 | Any | Any | 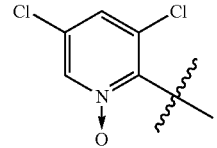 [SMILES: *c1c(Cl)cc(Cl)c[n+]1[O-]] |
| 11 | Any | Any | 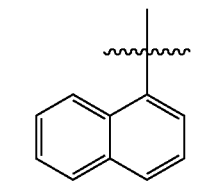 [SMILES: *c1cccc2ccccc12] |
| 12 | Any | Any | 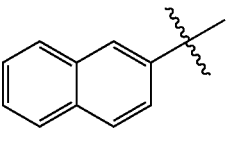 [SMILES: *c1ccc2ccccc2c1] |
| 13 | Any | Any | 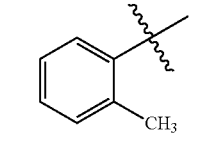 |
| 14 | Any | Any | 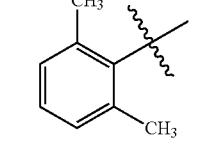 |
| 15 | Any | Any | 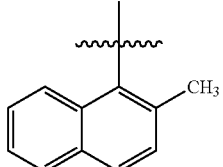 |
| 16 | Any | Any | 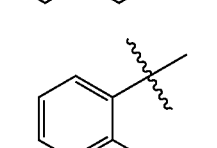 |
| 17 | Any | Any | 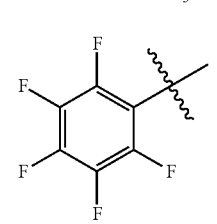 |
| 18 | Any | Any | 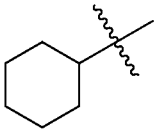 [SMILES: *C1CCCCC1] |
| 19 | Any | Any | 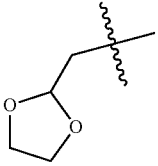 [SMILES: *CC1OCCO1] |
| 20 | Any | Any | 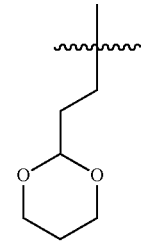 [SMILES: *CCC1OCCCO1] |
| 21 | Any | Any | 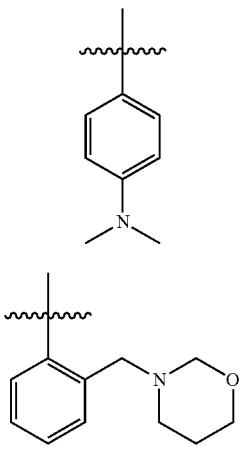 |
| 22 | Any | Any | 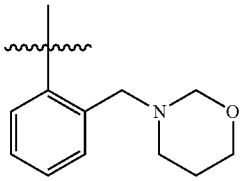 [SMILES: *c1ccccc1CN1CCCOC1] |
| 23 | Any | Any | 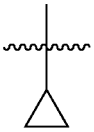 |
| 24 | Any | Any | 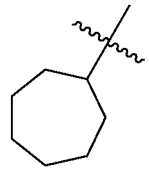 [SMILES: *C1CCCCCC1] |
| 25 | Any | Any | 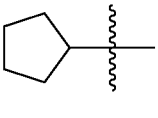 [SMILES: *C1CCCC1] |
| 26 | Any | Any | 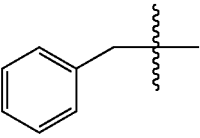 [SMILES: *Cc1ccccc1] |

TABLE 6-continued
| | R₂/R₃ | X | Z |
|---|---|---|---|
| 27 | Any | Any | 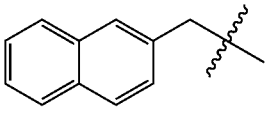 [SMILES: *Cc1ccc2ccccc2c1] |
| 28 | Any | Any | 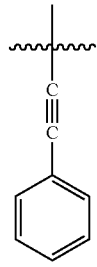 |
| 29 | Any | Any | 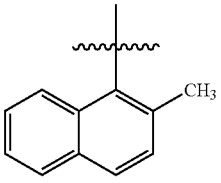 [SMILES: *c1c(C)ccc2ccccc12] |
| 30 | Any | Any | 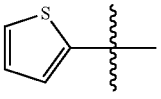 [SMILES: *c1cccs1] |
| 31 | Any | Any | 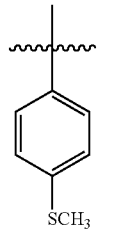 |
| 32 | Any | Any | 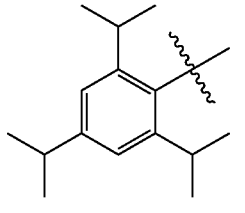 [SMILES: *c1c(C(C)C)cc(C(C)C)cc1C(C)C] |
| 33 | Any | Any | 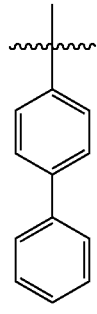 |
| 34 | Any | Any | 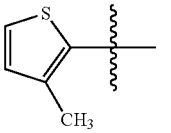 |
| 35 | Any | Any | 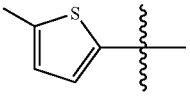 |
| 36 | Any | Any | 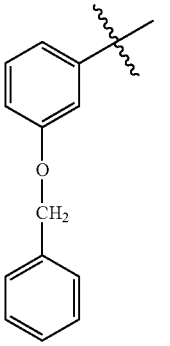 [SMILES: *c1cccc(OCc2ccccc2)c1] |
| 37 | Any | Any | 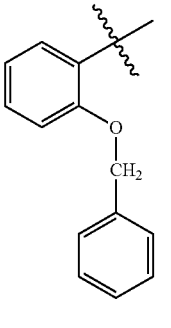 [SMILES: *c1ccccc1OCc1ccccc1] |
| 38 | Any | Any |  |
| 39 | Any | Any |  |

TABLE 6-continued

| | R₂/R₃ | X | Z |
|---|---|---|---|
| 40 | Any | Any | (structure: -O-CH₂-phenyl-O-phenyl) |
| 41 | Any | Any | (thiazol-2-yl) |
| 42 | Any | Any | (imidazol-2-yl) |
| 43 | Any | Any | (1-methyl-imidazol-2-yl) |

TABLE 7

| | R₂/R₃ | X | Z |
|---|---|---|---|
| 1 | Any | (6-chloropyridin-3-yl)methyl-N | Any |
| 2 | Any | (tetrahydrofuran-3-yl)methyl-N | Any |
| 3 | Any | (2-chlorothiazol-5-yl)methyl-N | Any |
| 4 | Any | (6-chloropyridin-3-yl)-N | Any |
| 5 | Any | (tetrahydrofuran-3-yl)-N | Any |
| 6 | Any | (2-chlorothiazol-5-yl)-N | Any |

EXAMPLES

The examples provided herein are intended to exemplify and not limit the invention. Mass spectral data were obtained using liquid chromatography mass spectroscopy (LC-MS). The masses are detected using electrospray ionization (ESI) and reported as Mol Ion (M+H, M−H).

Example 1

N-(4-chlorophenyl)-4-(2,6-difluorophenyl)-6-(2-(4-(trifluoromethoxy)benzylidene)hydrazinyl)-1,3,5-triazin-2-amine (1) was prepared using Method 1A: steps 1A.1, 2A.1 and 3A.1 to obtain the triazine as an amorphous solid. ESI/MS 520.8, 521.2, 523.0 (M+H), 519.2 (M−H).

Example 2

N-(4-chlorophenyl)-4-phenyl-6-(2-(4-(trifluoromethoxy)benzylidene)hydrazinyl)-1,3,5-triazin-2-amine (2) was prepared using Method 1A: Steps 1A.3, 2A.1 and 3A.1 to obtain the triazine as an amorphous solid. ESI/MS 484.9, 487 (M+H), 483.0, 485.0 (M−H).

Example 3

N-(4-chlorophenyl)-4-(2-(4-(trifluoromethoxy)benzylidene)hydrazinyl)-6-(4-(trifluoromethoxy)phenyl)-1,3,5-triazin-2-amine (3) Was prepared using Method 1A: Steps 1A.3, 2A.1 and 3A.1 to obtain the triazine as an amorphous solid. ESI/MS 568.5, 570.8 (M+H), 567.0, 569.0 (M−H).

Example 4

4-(2-chloro-6-fluorophenyl)-N-(4-chlorophenyl)-6-(2-(4-(trifluoromethoxy)benzylidene)hydrazinyl)-1,3,5-triazin-2-amine (4) Was prepared using Method 1A: Steps 1A.2, 2A.2, and 3A.2 to obtain the triazine as an amorphous solid. ESI/MS 537.1, 539.0, 541.0 (M+H), 535.1, 537.0 (M−H).

Example 5

4-(2,6-difluorophenyl)-N-(4-fluoro-3-(trifluoromethyl)phenyl)-6-(2-(4-(trifluoromethoxy)benzylidene)hydrazinyl)-1,3,5-triazin-2-amine (5) Was prepared using Method 1A: Steps 1A.1, 2A.1, and 3A.1 to obtain the triazine as an amorphous solid. ESI/MS 572.6 (M+H), 571.1 (M−H).

Example 6

4-(2,6-difluorophenyl)-6-(2-(4-(trifluoromethoxy)benzylidene)hydrazinyl)-N-(4-(trifluoromethoxy)phenyl)-1,3,5-triazin-2-amine (6) Was prepared using Method 1A: Steps 1A.1, 2A.1 and 3A.1 to obtain the triazine as an amorphous solid. ESI/MS 570.5 (M+H), 569.0 (M−H).

Example 7

4-(2,6-difluorophenyl)-6-(2-(4-(trifluoromethoxy)benzylidene)hydrazinyl)-N-(3-(trifluoromethyl)phenyl)-1,3,5-triazin-2-amine (7) Was prepared using Method 1A: Steps 1A.1, 2A.1 and 3A.1 to obtain the triazine as an amorphous solid. ESI/MS 554.5 (M+H), 553 (M−H).

Example 8

N-((6-chloropyridin-3-yl)methyl)-4-(2,6-difluorophenyl)-6-(2-(4-(trifluoromethoxy)benzylidene)hydrazinyl)-1,3,5-triazin-2-amine (8) Was prepared using Method 1A: Steps 1A.1, 2A.1 and 3A.1 to obtain the triazine as an amorphous solid. ESI/MS 535.6, 537.8 (M+H), 534.0, 536.0 (M−H).

Example 9

N-(6-chloropyridin-3-yl)-4-(2,6-difluorophenyl)-6-(2-(4-(trifluoromethoxy)benzylidene)hydrazinyl)-1,3,5-triazin-2-amine (9) Was prepared using Method 1A: Steps 1A.1, 2A.1 and 3A.1 to obtain the triazine as an amorphous solid. ESI/MS 521.5, 523.7 (M+H), 520.0, 521.9 (M−H).

Example 10

N-(4-chlorophenyl)-4-(2,6-difluorophenyl)-6-(2-(4-(1,1,2,2-tetrafluoroethoxy)benzylidene)hydrazinyl)-1,3,5-triazin-2-amine (10) Was prepared using Method 1A: Steps 1A.1, 2A.1 and 3A.1 to obtain the triazine as an amorphous solid. ESI/MS 553.1, 554.9 (M+H), 551.1, 553.1 (M−H).

Example 11

4-(2-chloro-6-fluorophenyl)-N-(4-chlorophenyl)-6-(2-(4-(1,1,2,2-tetrafluoroethoxy)benzylidene)hydrazinyl)-1,3,5-triazin-2-amine (11) Was prepared using Method 1A: Steps 1A.2, 2A.2 and 3A.1 to obtain the triazine as an amorphous solid. ESI/MS 569.1, 571.1, 573.1 (M+H), 567.1, 569.1 (M−H).

Example 12

4-(2-chloro-6-fluorophenyl)-N-(6-chloropyridin-3-yl)-6-(2-(4-(1,1,2,2-tetrafluoroethoxy)benzylidene)hydrazinyl)-1,3,5-triazin-2-amine (12) Was prepared using Method 1A: Steps 1A.2, 2A.1 and 3A.1 to obtain the triazine as an amorphous solid. ESI/MS 570.1, 572 (M+H), 568.1, 570 (M−H).

Example 13

4-(2-chloro-6-fluorophenyl)-N-(6-chloropyridin-3-yl)-6-(2-(4-(trifluoromethoxy)benzylidene)hydrazinyl)-1,3,5-triazin-2-amine (13) Was prepared using Method 1A: Steps 1A.2, 2A.1 and 3A.1 to obtain the triazine as an amorphous solid. ESI/MS 538, 539.8 (M+H), 536.1, 538 (M−H).

Example 14

N-(4-chlorophenyl)-4-(2,6-dichlorophenyl)-6-(2-(4-(trifluoromethoxy)benzylidene)hydrazinyl)-1,3,5-triazin-2-amine (14) Was prepared using Method 1A: Steps 1A.2, 2A.1 and 3A.1 to obtain the triazine as an amorphous solid. ESI/MS 553, 555, 556.9 (M+H), 551, 553.1, 555.1 (M−H).

Example 15

N-(6-chloropyridin-3-yl)-4-(2,6-difluorophenyl)-6-(2-(4-(1,1,2,2-tetrafluoroethoxy)benzylidene)hydrazinyl)-1,3,5-triazin-2-amine (15) Was prepared using Method 1A: Steps 1A.2, 2A.1 and 3A.1 to obtain the triazine as an amorphous solid. ESI/MS 554, 556.1, 558.1 (M+H), 552, 554.2, 556.2 (M−H).

Example 16

N-(6-chloropyridin-3-yl)-4-(2,6-dichlorophenyl)-6-(2-(4-(trifluoromethoxy)benzylidene)hydrazinyl)-1,3,5-triazin-2-amine (16) Was prepared using Method 1A: Steps 1A.2, 2A.1 and 3A.1 to obtain the triazine as an amorphous solid. ESI/MS 554, 556.1, 558.1 (M+H), 552, 554.2, 556.2 (M−H).

Example 17

4-(2-chloro-6-fluorophenyl)-N-(4-chlorophenyl)-6-(2-(4-ethylbenzylidene)hydrazinyl)-1,3,5-triazin-2-amine (17) Was prepared using Method 1A: Steps 1A.2, 2A.1 and 3A.1 to obtain the triazine as an amorphous solid. ESI/MS 481.3, 483.3 (M+H), 479.3, 481.3 (M−H).

Example 18

4-((2-(4-(2-chloro-6-fluorophenyl)-6-(4-chlorophenyl)amino)-1,3,5-triazin-2-yl)hydrazono)methyl)benzonitrile (18) Was prepared using Method 1A: Steps 1A.2, 2A.1 and 3A.1 to obtain the triazine as an amorphous solid. ESI/MS 478.2, 480.1 (M+H), 476.2, 478.2 (M−H).

Example 19

4-(2-butylidenehydrazinyl)-6-(2-chloro-6-fluorophenyl)-N-(4-chlorophenyl)-1,3,5-triazin-2-amine (19) Was prepared using Method 1A: Steps 1A.2, 2A.1 and 3A.1 to obtain the triazine as an amorphous solid. ESI/MS 419.2, 421.2 (M+H), 417.3, 419.2 (M−H).

Example 20

4-(2-chloro-6-fluorophenyl)-N-(4-chlorophenyl)-6-(2-(2-phenylethylidene)hydrazinyl)-1,3,5-triazin-2-amine (20) Was prepared using Method 1A: Steps 1A.2, 2A.1 and 3A.1 to obtain the triazine as an amorphous solid. ESI/MS 467.4, 469.4 (M+H).

Example 21

4-(2-chloro-6-fluorophenyl)-N-(4-chlorophenyl)-6-(2-(1-(4-(trifluoromethoxy)phenyl)ethylidene)hydrazinyl)-1,3,5-triazin-2-amine (21) Was prepared using Method 1A: Steps 1A.2, 2A.1 and 3A.1 to obtain the triazine as an amorphous solid. ESI/MS 551.3, 553.2 (M+H), 549.4, 551.4 (M−H).

Example 22

4-(2-chloro-6-fluorophenyl)-N-((6-chloropyridin-3-yl)methyl)-6-(2-(4-(trifluoromethoxy)benzylidene)hydrazinyl)-1,3,5-triazin-2-amine (22) Was prepared using Method

Example 23

4-(2-chloro-6-fluorophenyl)-N-(p-tolyl)-6-(2-(4-(trifluoromethoxy)benzylidene)hydrazinyl)-1,3,5-triazin-2-amine (23) Was prepared using Method 1C: Steps 1A.2, 2C and 3C to obtain the triazine as an amorphous solid. ESI/MS 517.3, 519.3 (M+H), 515.3, 517.6 (M-11).

Example 24

4-(2-chloro-6-fluorophenyl)-N-(2-morpholinoethyl)-6-(2-(4-(trifluoromethoxy)benzylidene)hydrazinyl)-1,3,5-triazin-2-amine (24) Was prepared using Method 1C: Steps 1A.2, 2C and 3C to obtain the triazine as an amorphous solid. ESI/MS 540.4, 542.4 (M+H), 538.5, 540.4 (M-H).

Example 25

2-(2-chloro-6-fluorophenyl)-4-(2,2-dimethylhydrazinyl)-6-(2-(4-(trifluoromethoxy)benzylidene)hydrazinyl)-1,3,5-triazine (25) Was prepared using Method 1C: Steps 1A.2, 2C and 3C to obtain the triazine as an amorphous solid. ESI/MS 470.3, 472.3 (M+H), 468.4, 470.4 (M-H).

Example 26

4-(2-chloro-6-fluorophenyl)-N-((tetrahydrofuran-3-yl)methyl)-6-(2-(4-(trifluoromethoxy)benzylidene)hydrazinyl)-1,3,5-triazin-2-amine (26) Was prepared using Method 1 C: Steps 1A.2, 2C and 3C to obtain the triazine as an amorphous solid. ESI/MS 511.3, 513.4 (M+H), 509.4, 511.4 (M-H).

Example 27

N-(4-chlorophenyl)-4-(2,4,6-trichlorophenyl)-6-(2-(4-(trifluoromethoxy)benzylidene)hydrazinyl)-1,3,5-triazin-2-amine (27) Was prepared using Method 1A: Steps 1A.2, 2A.1 and 3A.1 to obtain the triazine as an amorphous solid. ESI/MS 586.9, 588.9, 590.8, 592.9 (M+H), 585.0, 587.0, 588.9, 591.0 (M-H).

Example 28

N1-(4-(2-chloro-6-fluorophenyl)-6-(2-(4-(trifluoromethoxy)benzylidene)hydrazinyl)-1,3,5-triazin-2-yl)ethane-1,2-diamine (28) Was prepared using Method 1C: Steps 1A.2, 2C and 3C to obtain the triazine as an amorphous solid. ESI/MS 470.2, 472.2 (M+H), 468.3, 470.3 (M-H).

Example 29

N-(4-chlorophenyl)-4-(3-methoxyphenyl)-6-(2-(4-(trifluoromethoxy)benzylidene)hydrazinyl)-1,3,5-triazin-2-amine (29) Was prepared using Method 1A: Steps 1A.3, 2A.1 and 3A.1 to obtain the triazine as an amorphous solid. ESI/MS 515.5, 517.5 (M+H), 513.6, 515.5 (M-H).

Example 30

N-(4-chlorophenyl)-4-(4-methoxyphenyl)-6-(2-(4-(trifluoromethoxy)benzylidene)hydrazinyl)-1,3,5-triazin-2-amine (30) Was prepared using Method 1A: Steps 1A.3, 2A.1, and 3A.1 to obtain the triazine as an amorphous solid. ESI/MS 515.4, 517.2 (M+H), 513.3, 515.3 (M-H).

Example 31

N-(4-chlorophenyl)-4-(3-fluorophenyl)-6-(2-(4-(trifluoromethoxy)benzylidene)hydrazinyl)-1,3,5-triazin-2-amine (31) Was prepared using Method 1A: Steps 1A.3, 2A.1, and 3A.1 to obtain the triazine as an amorphous solid. ESI/MS 503.4, 505.4 (M+H), 501.5 (M-H).

Example 32

N-(4-chlorophenyl)-4-(3,4-dichlorophenyl)-6-(2-(4-(trifluoromethoxy)benzylidene)hydrazinyl)-1,3,5-triazin-2-amine (32) Was prepared using Method 1A: Steps 1A.3, 2A.1 and 3A.1 to obtain the triazine as an amorphous solid. ESI/MS 553.1, 555.1, 557.1 (M+H), 551.2, 553.2, 555.2 (M-H).

Example 33

N-(4-chlorophenyl)-4-(p-tolyl)-6-(2-(4-(trifluoromethoxy)benzylidene)hydrazinyl)-1,3,5-triazin-2-amine (33) Was prepared using Method 1A: Steps 1A.3, 2A.1 and 3A.1 to obtain the triazine as an amorphous solid. ESI/MS 499.4, 501.2 (M+H), 497.2, 499.2 (M-H).

Example 34

N-(3-chloro-4-fluorophenyl)-4-(2-chloro-6-fluorophenyl)-6-(2-(4-(trifluoromethoxy)benzylidene)hydrazinyl)-1,3,5-triazin-2-amine (34) Was prepared using Method 1A: Steps 1A.2, 2A.1 and 3A.1 to obtain the triazine as an amorphous solid. ESI/MS 555.1, 557.1 (M+H), 553.2, 555.1 (M-H).

Example 35

4-(2-chloro-6-fluorophenyl)-N-(4-fluoro-3-(trifluoromethyl)phenyl)-6-(2-(4-(trifluoromethoxy)benzylidene)hydrazinyl)-1,3,5-triazin-2-amine (35) Was prepared using Method 1A: Steps 1A.2, 2A.1 and 3A.1 to obtain the triazine as an amorphous solid. ESI/MS 589.2, 591.1 (M+H), 587.2, 589.2 (M-H).

Example 36

4-(2-(4-(2-chloro-1,1,2-trifluoroethoxy)benzylidene)hydrazinyl)-6-(2-chloro-6-fluorophenyl)-N-(6-chloropyridin-3-yl)-1,3,5-triazin-2-amine (36) Was prepared using Method 1A: Steps 1A.2, 2A.1 and 3A.1 to obtain the triazine as an amorphous solid. ESI/MS 586.0, 587.9, 589.9 (M+H), 584.0, 586.0, 588.0 (M-H).

Example 37

4-(2-(4-(2-chloro-1,1,2-trifluoroethoxy)benzylidene)hydrazinyl)-6-(2-chloro-6-fluorophenyl)-N-(4-chlorophenyl)-1,3,5-triazin-2-amine (37) Was prepared using Method 1A: Steps 1A.2, 2A.1 and 3A.1 to obtain the triazine as an amorphous solid. ESI/MS 585.0, 587.0, 589.0 (M+H), 583.1, 585.1, 587.1 (M-H).

Example 38

4-(2-chloro-6-fluorophenyl)-N-(3,4-dichlorophenyl)-6-(2-(4-(trifluoromethoxy)benzylidene)hydrazinyl)-1,3,5-triazin-2-amine (38) Was prepared using Method 1A: Steps 1A.2, 2A.1 and 3A.1 to obtain the triazine as an amorphous solid. ESI/MS 570.9, 572.9, 574.8 (M+H), 569.0, 571.0, 573.0 (M−H).

Example 39

4-(2-chloro-6-fluorophenyl)-N-(3,5-dichlorophenyl)-6-(2-(4-(trifluoromethoxy)benzylidene)hydrazinyl)-1,3,5-triazin-2-amine (39) Was prepared using Method 1A: Steps 1A.2, 2A.1 and 3A.1 to obtain the triazine as an amorphous solid. ESI/MS 571.0, 573.0, 574.9 (M+H), 569.1, 571.1, 573.0 (M−H).

Example 40

4-(2-chloro-6-fluorophenyl)-N-(2-chloropyridin-4-yl)-6-(2-(4-(trifluoromethoxy)benzylidene)hydrazinyl)-1,3,5-triazin-2-amine (40) Was prepared using Method 1A: Steps 1A.2, 2A.1 and 3A.1 to obtain the triazine as an amorphous solid. ESI/MS 538.1, 540.0, 542.0 (M+H), 536.1, 538.1 (M−H).

Example 41

4-(2-chloro-6-fluorophenyl)-N-(2-chlorophenyl)-6-(2-(4-(trifluoromethoxy)benzylidene)hydrazinyl)-1,3,5-triazin-2-amine (41) Was prepared using Method 1A: Steps 1A.2, 2A.1 and 3A.1 to obtain the triazine as an amorphous solid. ESI/MS 537.1, 539.1 (M+H), 535.1, 537.1 (M−H).

Example 42

N-(6-chloropyridin-3-yl)-4-(2-fluorophenyl)-6-(2-(4-(trifluoromethoxy)benzylidene)hydrazinyl)-1,3,5-triazin-2-amine (42) Was prepared using Method 1A: Steps 1A.4, 2A.1 and 3A.1 to obtain the triazine as an amorphous solid. ESI/MS 503.9, 505.9 (M+H), 5502.0, 504.0 (M−H).

Example 43

4-(2-chloro-6-fluorophenyl)-N-methyl-6-(2-(4-(trifluoromethoxy)benzylidene)hydrazinyl)-1,3,5-triazin-2-amine (43) Was prepared using Method 1A: Steps 1A.3, 2A.1 and 3A.1 to obtain the triazine as an amorphous solid. ESI/MS 440.6, 443.0 (M+H), 439.0, 441.0 (M−H).

Example 44

N-(4-chlorophenyl)-4-(2-fluorophenyl)-6-(2-(4-(trifluoromethoxy)benzylidene)hydrazinyl)-1,3,5-triazin-2-amine (44) Was prepared using Method 1A: Steps 1A.4, 2A.1 and 3A.1 to obtain the triazine as an amorphous solid. ESI/MS 503.0, 504.9 (M+H), 501.1, 503.1 (M−H).

Example 45

4-(2-chloro-6-fluorophenyl)-N-(5-chloropyridin-2-yl)-6-(2-(4-(trifluoromethoxy)benzylidene)hydrazinyl)-1,3,5-triazin-2-amine (45) Was prepared using Method 1A: Steps 1A.2, 2A.3 and 3A.1 to obtain the triazine as an amorphous solid. ESI/MS 537.862, 539.879 (M+H).

Example 46

N-(4-chlorophenyl)-2-phenyl-6-(2-(4-(trifluoromethoxy)benzylidene)hydrazinyl)pyrimidin-4-amine (46) Was prepared using Method 4: Steps 2C and 3C to obtain the pyrimidine as an amorphous solid. ESI/MS 483.6, 485.9 (M+H), 482.0, 484.0 (M−H).

Example 47

N-(6-chloropyridin-3-yl)-6-phenyl-2-(2-(4-(trifluoromethoxy)benzylidene)hydrazinyl)pyrimidin-4-amine (47) Was prepared using Method 2: Steps 1A.3, 2A.1 and 3A to obtain the pyrimidine as an amorphous solid. ESI/MS 485.2, 487.2 (M+H), 483.0, 485.0 (M−H).

Example 48

4-(2-(2-chloro-6-fluorobenzylidene)hydrazinyl)-N-(4-chlorophenyl)-6-(4-(trifluoromethoxy)phenyl)-1,3,5-triazin-2-amine (48) Was prepared using Method 1A: Steps 1A.3, 2A.1 and 3A.1 to obtain the triazine as an amorphous solid. ESI/MS 537.0, 539.0 (M+H), 535.0, 537.0 (M−H).

Example 49

N-(5-chloropyridin-2-yl)-6-phenyl-2-(2-(4-(trifluoromethoxy)benzylidene)hydrazinyl)pyrimidin-4-amine (49) Was prepared using Method 2: Steps 1A.3, 2A.1 and 3A to obtain the pyrimidine as an amorphous solid. ESI/MS 485.1, 486.9 (M+H), 483.1, 485.1 (M−H).

Example 50

4-((2-(4-(2-chloro-6-fluorophenyl)-6-(6-chloropyridin-3-yl)amino)-1,3,5-triazin-2-yl)hydrazono)methyl)phenol (50) Was prepared using Method 1A: Steps 1A.2, 2A.1 and 3A.1 to obtain the triazine as an amorphous solid. ESI/MS 470.2, 472.0 (M+H), 468.1, 470.1 (M−H).

Example 51

4-(2-chloro-6-fluorophenyl)-N-(6-chloropyridin-3-yl)-6-(2-(4-(trifluoromethyl)benzylidene)hydrazinyl)-1,3,5-triazin-2-amine (51) Was prepared using Method 1A: Steps 1A.2, 2A.1 and 3A.1 to obtain the triazine as an amorphous solid. ESI/MS 522.1, 524.1 (M+H), 520.1, 522.1 (M−H).

Example 52

6-(2-chloro-6-fluorophenyl)-N-(4-chlorophenyl)-2-(2-(4-(trifluoromethoxy)benzylidene)hydrazinyl)pyrimidin-4-amine (52) Was prepared using Method 2: Steps 1A.2, 2A.1 and 3A to obtain the pyrimidine as an amorphous solid. ESI/MS 536.1, 538.1 (M+H), 534.1, 536.1 (M−H).

Example 53

4-(2-chloro-6-fluorophenyl)-N-(6-chloropyridin-3-yl)-6-(2-(4-methylbenzylidene)hydrazinyl)-1,3,5-triazin-2-amine (53) Was prepared using Method 1A: Steps 1A.2, 2A.1 and 3A.1 to obtain the triazine as an amorphous solid. ESI/MS 468.1, 470.1 (M+H), 466.1, 468.1 (M−H).

Example 54

4-(2-chloro-6-fluorophenyl)-N-(6-chloropyridin-3-yl)-6-(2-(4-methoxybenzylidene)hydrazinyl)-1,3,5-triazin-2-amine (54) Was prepared using Method 1A: Steps 1A.2, 2A.1 and 3A.1 to obtain the triazine as an amorphous solid. ESI/MS 484.0, 486.0 (M+H), 482.1, 484.1 (M–H).

Example 55

4-(2-chloro-6-fluorophenyl)-N-(6-chloropyridin-3-yl)-6-(2-(3-fluoro-4-(trifluoromethyl)benzylidene)hydrazinyl)-1,3,5-triazin-2-amine (55) Was prepared using Method 1A: Steps 1A.2, 2A.1 and 3A.1 to obtain the triazine as an amorphous solid. ESI/MS 540.0, 542.0 (M+H), 538.0, 540.0 (M–H).

Example 56

N-((6-chloropyridin-3-yl)methyl)-6-phenyl-2-(2-(4-(trifluoromethoxy)benzylidene)hydrazinyl)pyrimidin-4-amine (56) Was prepared using Method 2: Steps 1A.3, 2A.1 and 3A to obtain the pyrimidine as an amorphous solid. ESI/MS 499.0, 501.0 (M+H), 497.1, 499.1 (M–H).

Example 57

N-(4-chlorophenyl)-6-phenyl-2-(2-(4-(trifluoromethoxy)benzylidene)hydrazinyl)pyrimidin-4-amine (57) Was prepared using Method 2: Steps 1A.3, 2A.2 and 3A to obtain the pyrimidine as an amorphous solid. ESI/MS 483.966, 486.030 (M+H).

Example 58

N-(4-chlorophenyl)-4-phenyl-6-(2-(4-(trifluoromethoxy)benzylidene)hydrazinyl)pyrimidin-2-amine (58) Was prepared using Method 3: Steps 1A.3, 2B and 3B to obtain the pyrimidine as an amorphous solid. ESI/MS 483.9728, 485.9988 (M+H).

Example 59

6-(2-chloro-6-fluorophenyl)-N-(6-chloropyridin-3-yl)-2-(2-(4-(trifluoromethoxy)benzylidene)hydrazinyl)pyrimidin-4-amine (59) Was prepared using Method 2: Steps 1A.2, 2A.1 and 3A to obtain the pyrimidine as an amorphous solid. ESI/MS 537.0, 538.9 (M+H), 535.1, 537.0 (M–H).

Example 60

4-(2-chloro-6-fluorophenyl)-N-(4-chlorobenzyl)-6-(2-(4-(trifluoromethoxy)benzylidene)hydrazinyl)-1,3,5-triazin-2-amine (60) Was prepared using Method 1A: Steps 1A.2, 2A.1 and 3A.1 to obtain the triazine as an amorphous solid. ESI/MS 551.3, 553.3 (M+H), 549.2, 551.2 (M–H).

Example 61

N-(4-chlorobenzyl)-6-phenyl-2-(2-(4-(trifluoromethoxy)benzylidene)hydrazinyl)pyrimidin-4-amine (61) Was prepared using Method 2: Steps 1A.3, 2A.1 and 3A to obtain the pyrimidine as an amorphous solid. ESI/MS 498.3, 500.1 (M+H), 496.3, 498.3 (M–H).

Insecticidal Testing

The compounds identified in Table 8 were prepared according to the previous methods and were tested against beet armyworm and corn earworm as follows:

Insecticidal Test for Beet Armyworm (*Spodoptera exigua*).

To prepare the test solution, the test compound was Formulated at 3499 ppm in solution as 5 mg compound/1.429 mL of 9 parts acetone: 1 part deionized $H_2O$ and vortexed to homogenize. 50 µL of the 3499 ppm (equivalent to 100 µg/cm$^2$ dose on diet surface area) test solution was pipetted upon the surface of 1 mL of solidified cool Southland Products Incorporated Beet Armyworm Diet (201 Stuart Island Road Lake Village, Ark. 71653) using an Eppendorf Repeater Plus with a 1 mL pipette tip. All pipetting of treatments was done in a Labconco Hood. Thirty minutes were allowed for the acetone to evaporate leaving a dose of 100 µg/cm$^2$ on the surface of the artificial diet. Two 24 hour old first instar Beet Armyworm (*Spodoptera Exigua*) larvae were placed in each well of the 128 well Bio-BA 128 Bioassay trays (CD International, Pitman, N.J., 08071, USA) using a #0 fine camel hair paint brush. Bioassay trays were sectioned into treatment groups of 8 with 16 replicates per treatment group (32 insects per treatment). Trays containing the treated diet and larvae were covered with a Bio-CV-16 cover (CD International, Pitman, N.J., 08071, USA) and then placed on a rack under florescent lights at 27° C., 20% relative humidity (RH) in the room, and 16 hr light: 8 hr dark for 96 hours. Observations were made 24, 48 and 96 hours after treatment and infestation. The number of insects dead were counted out of the 32 insects total per treatment and the results are given in a table as a percent mortality at a dose of 100 µg/cm$^2$. When finished, the tray was moved to the –5° C. freezer and left for 24 hr to insure mortality of the remaining *S. exigua*. After 24 hours, dispose of entire tray into waste bin.

Keys to the table: Mortality refers to activity against beet army worm (*Spodoptera exigua*) as defined above at the concentration of 100 µg/cm$^2$ (A=76-100% mortality, B=51-75% mortality, C=26-50% mortality and D=0-25% mortality).

TABLE 8

| Ex | Structure | Appearance | Mortality | Conc | name |
|---|---|---|---|---|---|
| 1 | 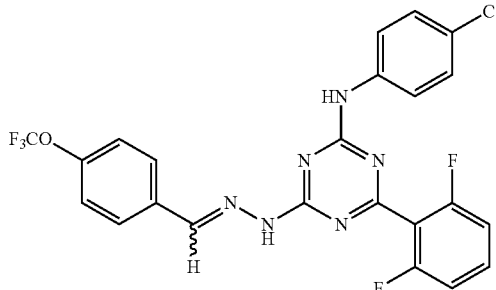 | Glass foam | A | 100 | N-(4-chlorophenyl)-4-(2,6-difluorophenyl)-6-(2-(4-(trifluoromethoxy)benzylidene)hydrazinyl)-1,3,5-triazin-2-amine |

TABLE 8-continued

| Ex | Structure | Appearance | Mortality | Conc | name |
|---|---|---|---|---|---|
| 2 | 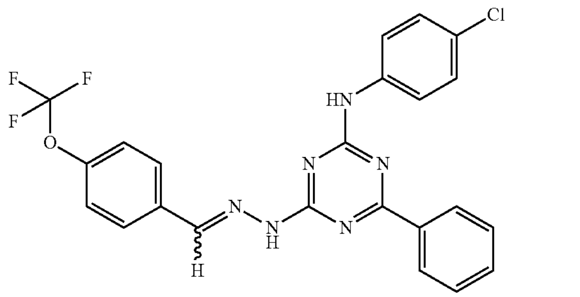 [SMILES: FC(F)(F)Oc1ccc(C=NNc2nc(Nc3ccc(Cl)cc3)nc(-c3ccccc3)n2)cc1] | Film | A | 100 | N-(4-chlorophenyl)-4-phenyl-6-(2-(4-(trifluoromethoxy)benzylidene)hydrazinyl)-1,3,5-triazin-2-amine |
| 3 | 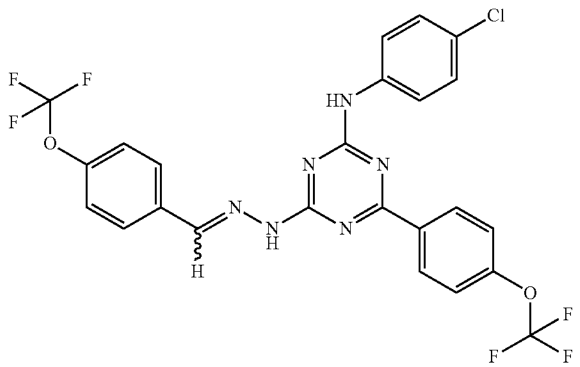 [SMILES: FC(F)(F)Oc1ccc(C=NNc2nc(Nc3ccc(Cl)cc3)nc(-c3ccc(OC(F)(F)F)cc3)n2)cc1] | White solid | C | 100 | N-(4-chlorophenyl)-4-(2-(4-(trifluoromethoxy)benzylidene)hydrazinyl)-6-(4-(trifluoromethoxy)phenyl)-1,3,5-triazin-2-amine |
| 4 | 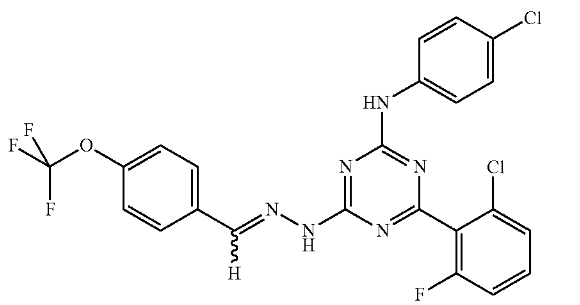 [SMILES: Fc1cccc(Cl)c1-c1nc(NN=Cc2ccc(OC(F)(F)F)cc2)nc(Nc2ccc(Cl)cc2)n1] | White solid | A | 100 | 4-(2-chloro-6-fluorophenyl)-N-(4-chlorophenyl)-6-(2-(4-(trifluoromethoxy)benzylidene)hydrazinyl)-1,3,5-triazin-2-amine |
| 5 | 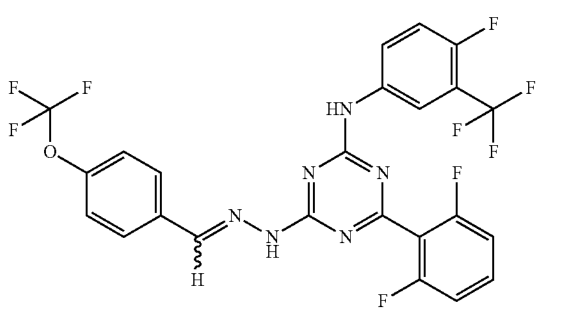 [SMILES: Fc1ccc(Nc2nc(NN=Cc3ccc(OC(F)(F)F)cc3)nc(-c3c(F)cccc3F)n2)cc1C(F)(F)F] | Solid film glass | C | 100 | 4-(2,6-difluorophenyl)-N-(4-fluoro-3-(trifluoromethyl)phenyl)-6-(2-(4-(trifluoromethoxy)benzylidene)hydrazinyl)-1,3,5-triazin-2-amine |
| 6 | 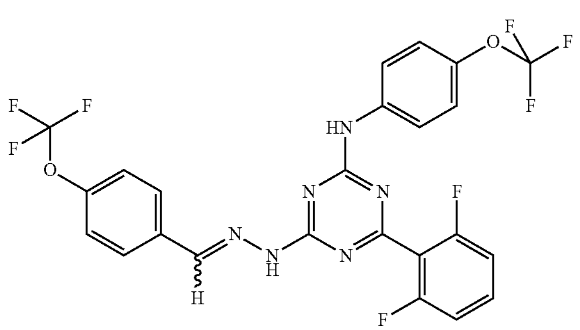 [SMILES: Fc1cccc(F)c1-c1nc(NN=Cc2ccc(OC(F)(F)F)cc2)nc(Nc2ccc(OC(F)(F)F)cc2)n1] | White solid | C | 100 | 4-(2,6-difluorophenyl)-6-(2-(4-(trifluoromethoxy)benzylidene)hydrazinyl)-N-(4-(trifluoromethoxy)phenyl)-1,3,5-triazin-2-amine |

TABLE 8-continued

| Ex | Structure | Appearance | Mortality | Conc | name |
|---|---|---|---|---|---|
| 7 | 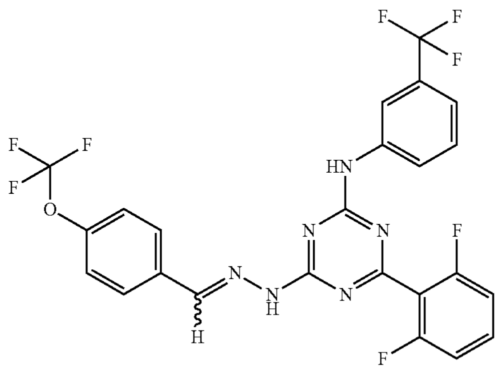 [SMILES: Fc1cccc(F)c1-c1nc(NN=Cc2ccc(OC(F)(F)F)cc2)nc(Nc2cccc(C(F)(F)F)c2)n1] | Foam film | D | 100 | 4-(2,6-difluorophenyl)-6-(2-(4-(trifluoromethoxy)benzylidene)hydrazinyl)-N-(3-(trifluoromethyl)phenyl)-1,3,5-triazin-2-amine |
| 8 | 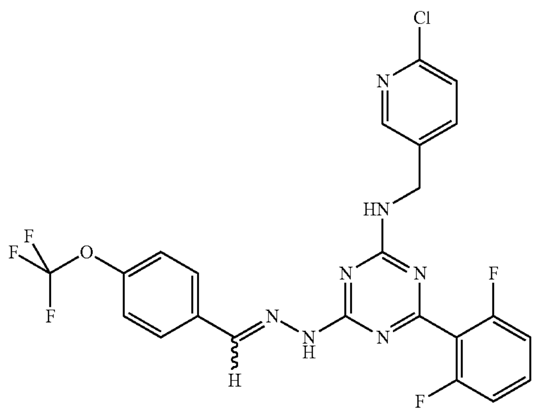 [SMILES: Fc1cccc(F)c1-c1nc(NCc2ccc(Cl)nc2)nc(NN=Cc2ccc(OC(F)(F)F)cc2)n1] | Film | A | 100 | N-((6-chloropyridin-3-yl)methyl)-4-(2,6-difluorophenyl)-6-(2-(4-(trifluoromethoxy)benzylidene)hydrazinyl)-1,3,5-triazin-2-amine |
| 9 | 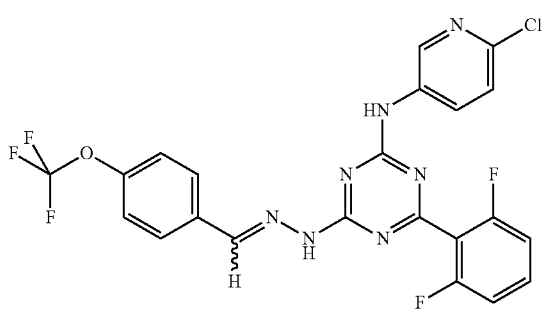 [SMILES: Fc1cccc(F)c1-c1nc(NN=Cc2ccc(OC(F)(F)F)cc2)nc(Nc2ccc(Cl)nc2)n1] | Solid | A | 100 | N-(6-chloropyridin-3-yl)-4-(2,6-difluorophenyl)-6-(2-(4-(trifluoromethoxy)benzylidene)hydrazinyl)-1,3,5-triazin-2-amine |
| 10 | 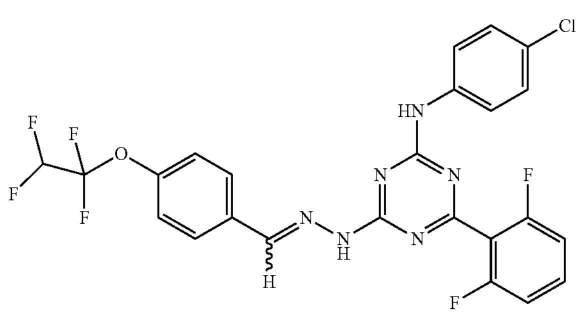 | Glass | A | 100 | N-(4-chlorophenyl)-4-(2,6-difluorophenyl)-6-(2-(4-(1,1,2,2-tetrafluoroethoxy)benzylidene)hydrazinyl)-1,3,5-triazin-2-amine |

TABLE 8-continued

| Ex | Structure | Appearance | Mortality | Conc | name |
|---|---|---|---|---|---|
| 11 | 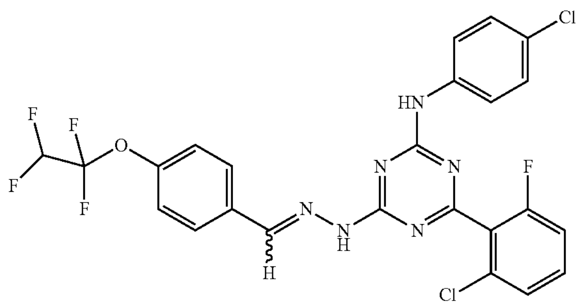 | Film | A | 100 | 4-(2-chloro-6-fluorophenyl)-N-(4-chlorophenyl)-6-(2-(4-(1,1,2,2-tetrafluoroethoxy)benzylidene)hydrazinyl)-1,3,5-triazin-2-amine |
| 12 | 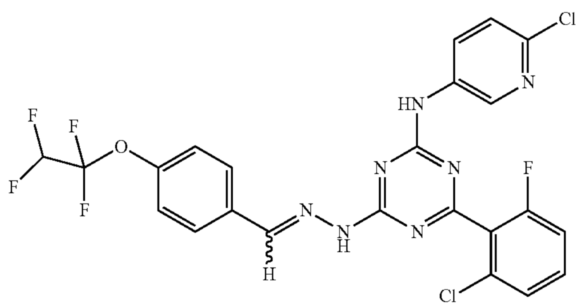 [SMILES: Fc1cccc(Cl)c1-c1nc(NN=Cc2ccc(OC(F)(F)C(F)F)cc2)nc(Nc2ccc(Cl)nc2)n1] | Film | A | 100 | 4-(2-chloro-6-fluorophenyl)-N-(6-chloropyridin-3-yl)-6-(2-(4-(1,1,2,2-tetrafluoroethoxy)benzylidene)hydrazinyl)-1,3,5-triazin-2-amine |
| 13 | 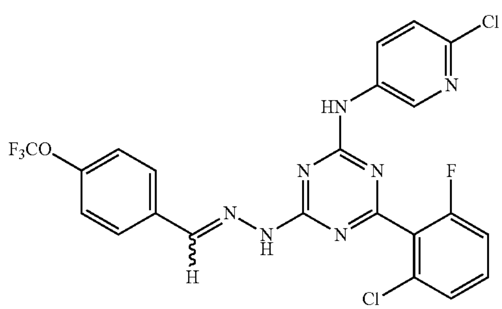 [SMILES: Fc1cccc(Cl)c1-c1nc(NN=Cc2ccc(OC(F)(F)F)cc2)nc(Nc2ccc(Cl)nc2)n1] | Solid glass | A | 100 | 4-(2-chloro-6-fluorophenyl)-N-(6-chloropyridin-3-yl)-6-(2-(4-(trifluoromethoxy)benzylidene)hydrazinyl)-1,3,5-triazin-2-amine |
| 14 | 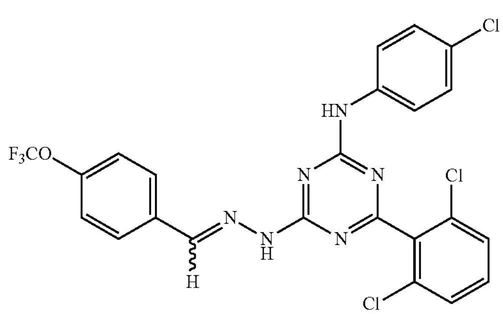 [SMILES: FC(F)(F)Oc1ccc(C=NNc2nc(Nc3ccc(Cl)cc3)nc(-c3c(Cl)cccc3Cl)n2)cc1] | Solid | B | 100 | N-(4-chlorophenyl)-4-(2,6-dichlorophenyl)-6-(2-(4-(trifluoromethoxy)benzylidene)hydrazinyl)-1,3,5-triazin-2-amine |
| 15 | 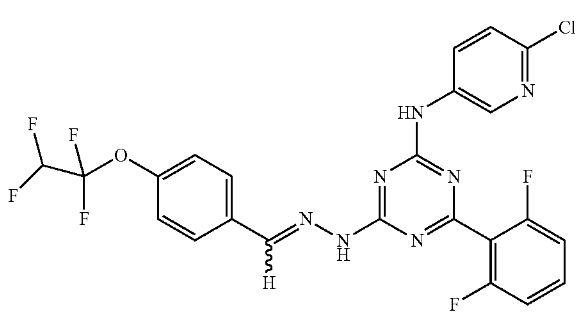 [SMILES: Fc1cccc(F)c1-c1nc(NN=Cc2ccc(OC(F)(F)C(F)F)cc2)nc(Nc2ccc(Cl)nc2)n1] | Foam solid | A | 100 | N-(6-chloropyridin-3-yl)-4-(2,6-difluorophenyl)-6-(2-(4-(1,1,2,2-tetrafluoroethoxy)benzylidene)hydrazinyl)-1,3,5-triazin-2-amine |

TABLE 8-continued

| Ex | Structure | Appearance | Mortality | Conc | name |
|---|---|---|---|---|---|
| 16 | 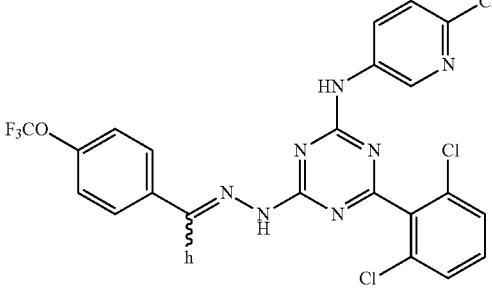 | Yellow solid | A | 100 | N-(6-chloropyridin-3-yl)-4-(2,6-dichlorophenyl)-6-(2-(4-(trifluoromethoxy)benzylidene)hydrazinyl)-1,3,5-triazin-2-amine |
| 17 | 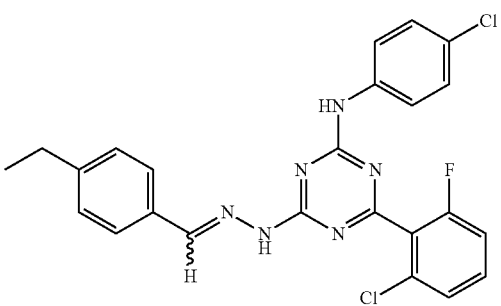 [SMILES: CCc1ccc(C=NNc2nc(Nc3ccc(Cl)cc3)nc(-c3c(F)cccc3Cl)n2)cc1] | glass | A | 100 | 4-(2-chloro-6-fluorophenyl)-N-(4-chlorophenyl)-6-(2-(4-ethylbenzylidene)hydrazinyl)-1,3,5-triazin-2-amine |
| 18 | 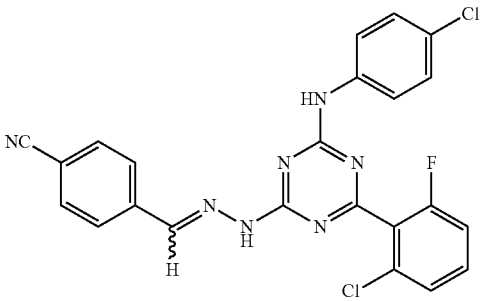 [SMILES: N#Cc1ccc(C=NNc2nc(Nc3ccc(Cl)cc3)nc(-c3c(F)cccc3Cl)n2)cc1] | White solid | A | 100 | 4-((2-(4-(2-chloro-6-fluorophenyl)-6-((4-chlorophenyl)amino)-1,3,5-triazin-2-yl)hydrazono)methyl)benzonitrile |
| 19 | 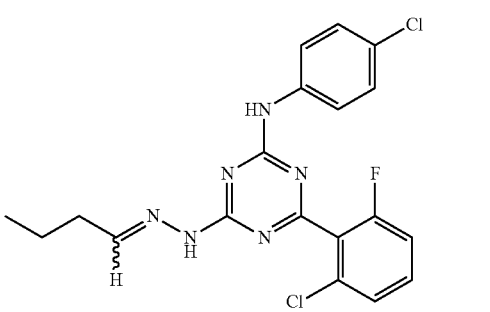 [SMILES: CCCC=NNc1nc(Nc2ccc(Cl)cc2)nc(-c2c(F)cccc2Cl)n1] | glass | A | 100 | 4-(2-butylidenehydrazinyl)-6-(2-chloro-6-fluorophenyl)-N-(4-chlorophenyl)-1,3,5-triazin-2-amine |
| 20 | 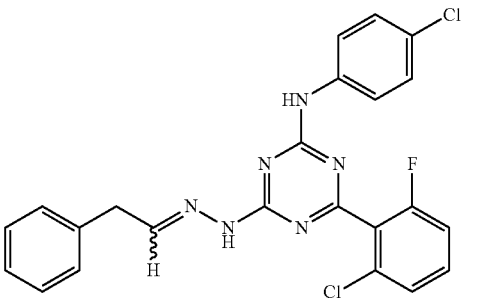 [SMILES: Fc1cccc(Cl)c1-c1nc(NN=CCc2ccccc2)nc(Nc2ccc(Cl)cc2)n1] | Yellow solid | A | 100 | 4-(2-chloro-6-fluorophenyl)-N-(4-chlorophenyl)-6-(2-(2-phenylethylidene)hydrazinyl)-1,3,5-triazin-2-amine |

TABLE 8-continued

| Ex | Structure | Appearance | Mortality | Conc | name |
|---|---|---|---|---|---|
| 21 | 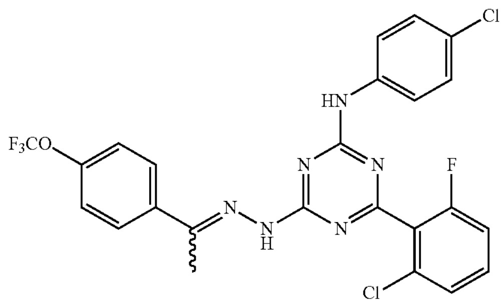 | glass | A | 100 | 4-(2-chloro-6-fluorophenyl)-N-(4-chlorophenyl)-6-(2-(1-(4-(trifluoromethoxy)phenyl)ethylidene)hydrazinyl)-1,3,5-triazin-2-amine |
| 22 | 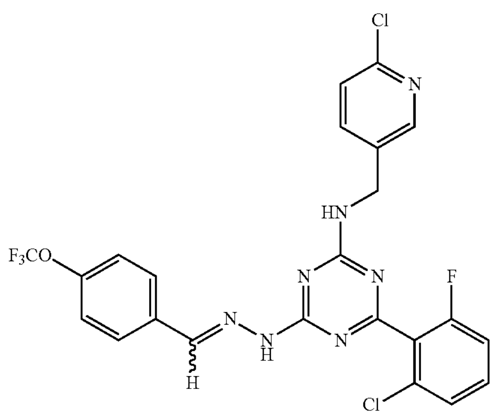 [SMILES: Fc1cccc(Cl)c1-c1nc(NCc2ccc(Cl)nc2)nc(NN=Cc2ccc(OC(F)(F)F)cc2)n1] | White solid | A | 100 | 4-(2-chloro-6-fluorophenyl)-N-((6-chloropyridin-3-yl)methyl)-6-(2-(4-(trifluoromethoxy)benzylidene)hydrazinyl)-1,3,5-triazin-2-amine |
| 23 | 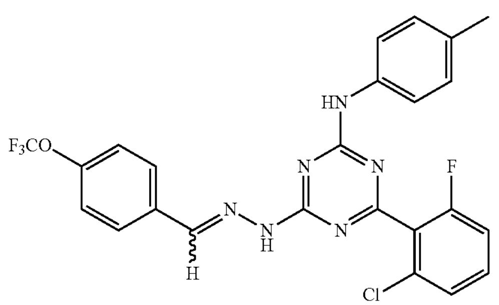 [SMILES: Cc1ccc(Nc2nc(NN=Cc3ccc(OC(F)(F)F)cc3)nc(-c3c(F)cccc3Cl)n2)cc1] | film | A | 100 | 4-(2-chloro-6-fluorophenyl)-N-(p-tolyl)-6-(2-(4-(trifluoromethoxy)benzylidene)hydrazinyl)-1,3,5-triazin-2-amine |
| 24 | 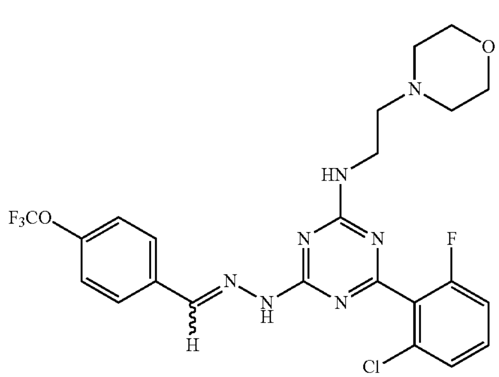 [SMILES: Fc1cccc(Cl)c1-c1nc(NCCN2CCOCC2)nc(NN=Cc2ccc(OC(F)(F)F)cc2)n1] | film | A | 100 | 4-(2-chloro-6-fluorophenyl)-N-(2-morpholinoethyl)-6-(2-(4-(trifluoromethoxy)benzylidene)hydrazinyl)-1,3,5-triazin-2-amine |

| Ex | Structure | Appearance | Mortality | Conc | name |
|---|---|---|---|---|---|
| 25 | 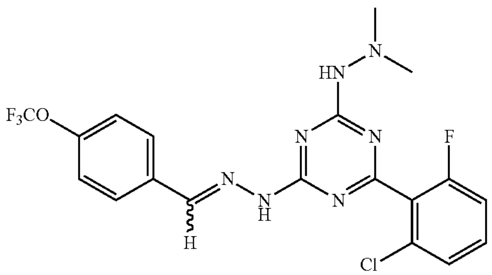 [SMILES: CN(C)Nc1nc(NN=Cc2ccc(OC(F)(F)F)cc2)nc(-c2c(F)cccc2Cl)n1] | film | A | 100 | 2-(2-chloro-6-fluorophenyl)-4-(2,2-dimethylhydrazinyl)-6-(2-(4-(trifluoromethoxy)benzylidene)hydrazinyl)-1,3,5-triazine |
| 26 | 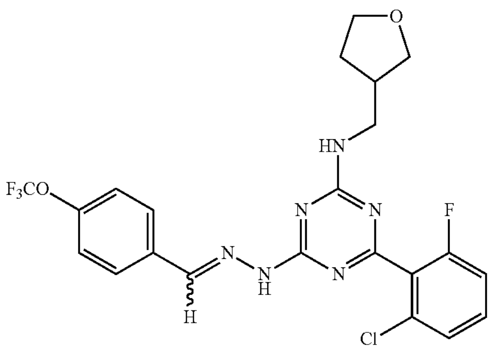 [SMILES: Fc1cccc(Cl)c1-c1nc(NCC2CCOC2)nc(NN=Cc2ccc(OC(F)(F)F)cc2)n1] | film | D | 100 | 4-(2-chloro-6-fluorophenyl)-N-((tetrahydrofuran-3-yl)methyl)-6-(2-(4-(trifluoromethoxy)benzylidene)hydrazinyl)-1,3,5-triazin-2-amine |
| 27 | 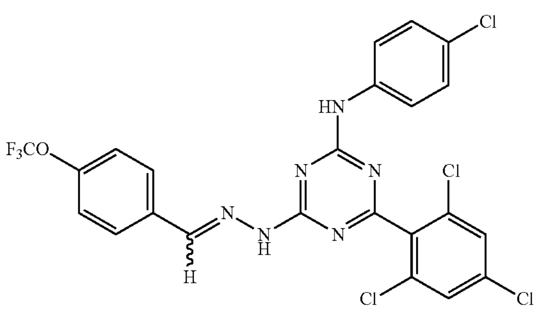 [SMILES: FC(F)(F)Oc1ccc(C=NNc2nc(Nc3ccc(Cl)cc3)nc(-c3c(Cl)cc(Cl)cc3Cl)n2)cc1] | White solid | D | 100 | N-(4-chlorophenyl)-4-(2,4,6-trichlorophenyl)-6-(2-(4-(trifluoromethoxy)benzylidene)hydrazinyl)-1,3,5-triazin-2-amine |
| 28 | 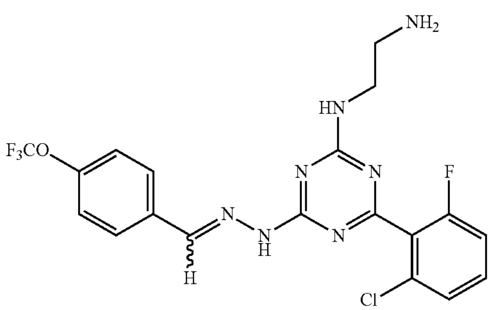 [SMILES: NCCNc1nc(NN=Cc2ccc(OC(F)(F)F)cc2)nc(-c2c(F)cccc2Cl)n1] | White solid | D | 100 | N1-(4-(2-chloro-6-fluorophenyl)-6-(2-(4-(trifluoromethoxy)benzylidene)hydrazinyl)-1,3,5-triazin-2-yl)ethane-1,2-diamine |
| 29 | 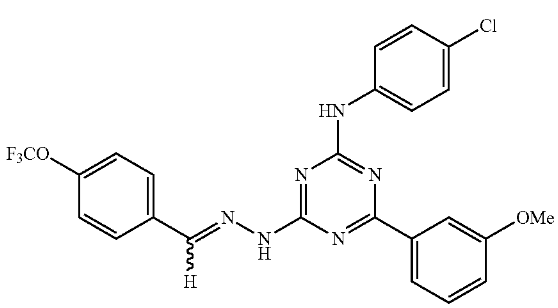 [SMILES: COc1cccc(-c2nc(NN=Cc3ccc(OC(F)(F)F)cc3)nc(Nc3ccc(Cl)cc3)n2)c1] | solid | D | 100 | N-(4-chlorophenyl)-4-(3-methoxyphenyl)-6-(2-(4-(trifluoromethoxy)benzylidene)hydrazinyl)-1,3,5-triazin-2-amine |

TABLE 8-continued

| Ex | Structure | Appearance | Mortality | Conc | name |
|---|---|---|---|---|---|
| 30 | 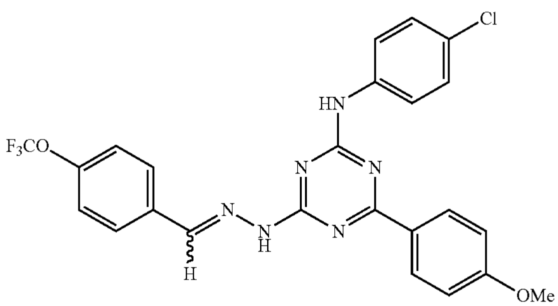 [SMILES: COc1ccc(-c2nc(NN=Cc3ccc(OC(F)(F)F)cc3)nc(Nc3ccc(Cl)cc3)n2)cc1] | Tan solid | D | 100 | N-(4-chlorophenyl)-4-(4-methoxyphenyl)-6-(2-(4-(trifluoromethoxy)benzylidene)hydrazinyl)-1,3,5-triazin-2-amine |
| 31 | 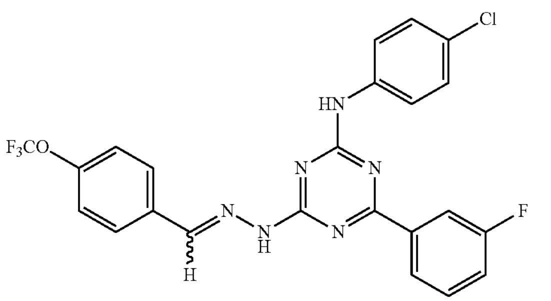 [SMILES: Fc1cccc(-c2nc(NN=Cc3ccc(OC(F)(F)F)cc3)nc(Nc3ccc(Cl)cc3)n2)c1] | foam | B | 100 | N-(4-chlorophenyl)-4-(3-fluorophenyl)-6-(2-(4-(trifluoromethoxy)benzylidene)hydrazinyl)-1,3,5-triazin-2-amine |
| 32 | 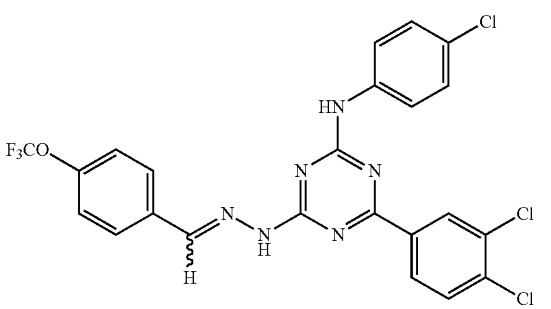 [SMILES: FC(F)(F)Oc1ccc(C=NNc2nc(Nc3ccc(Cl)cc3)nc(-c3ccc(Cl)c(Cl)c3)n2)cc1] | Yellow solid | D | 100 | N-(4-chlorophenyl)-4-(3,4-dichlorophenyl)-6-(2-(4-(trifluoromethoxy)benzylidene)hydrazinyl)-1,3,5-triazin-2-amine |
| 33 | 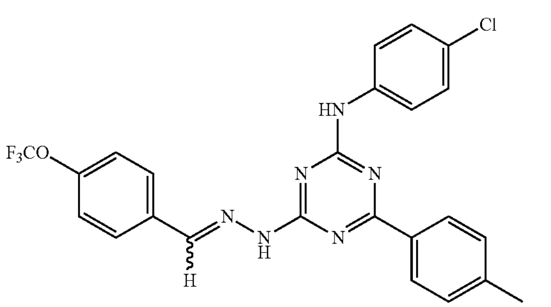 [SMILES: Cc1ccc(-c2nc(NN=Cc3ccc(OC(F)(F)F)cc3)nc(Nc3ccc(Cl)cc3)n2)cc1] | White solid | D | 100 | N-(4-chlorophenyl)-4-(p-tolyl)-6-(2-(4-(trifluoromethoxy)benzylidene)hydrazinyl)-1,3,5-triazin-2-amine |
| 34 | 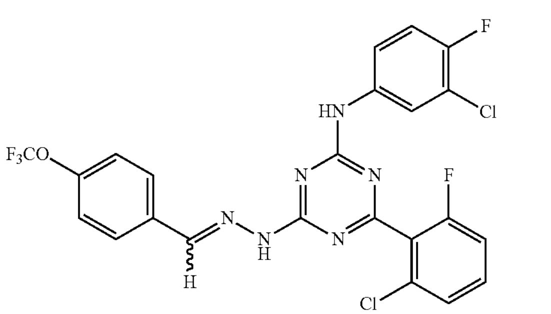 [SMILES: Fc1ccc(Nc2nc(NN=Cc3ccc(OC(F)(F)F)cc3)nc(-c3c(F)cccc3Cl)n2)cc1Cl] | glass | A | 100 | N-(3-chloro-4-fluorophenyl)-4-(2-chloro-6-fluorophenyl)-6-(2-(4-(trifluoromethoxy)benzylidene)hydrazinyl)-1,3,5-triazin-2-amine |

TABLE 8-continued

| Ex | Structure | Appearance | Mortality | Conc | name |
|---|---|---|---|---|---|
| 35 | 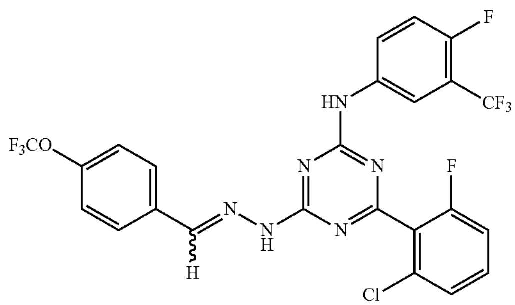 [SMILES: Fc1ccc(Nc2nc(NN=Cc3ccc(OC(F)(F)F)cc3)nc(-c3c(F)cccc3Cl)n2)cc1C(F)(F)F] | White solid | A | 100 | 4-(2-chloro-6-fluorophenyl)-N-(4-fluoro-3-(trifluoromethyl)phenyl)-6-(2-(4-(trifluoromethoxy)benzylidene)hydrazinyl)-1,3,5-triazin-2-amine |
| 36 | 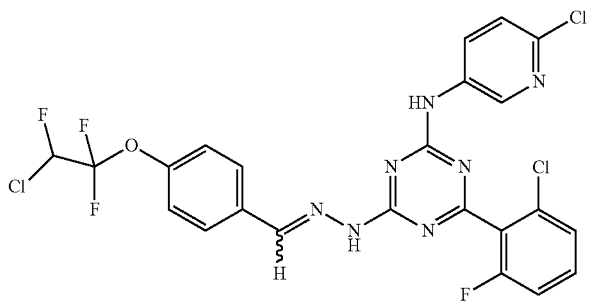 [SMILES: Fc1cccc(Cl)c1-c1nc(NN=Cc2ccc(OC(F)(F)C(F)Cl)cc2)nc(Nc2ccc(Cl)nc2)n1] | glass | A | 100 | 4-(2-(4-(2-chloro-1,1,2-trifluoroethoxy)benzylidene)hydrazinyl)-6-(2-chloro-6-fluorophenyl)-N-(6-chloropyridin-3-yl)-1,3,5-triazin-2-amine |
| 37 | 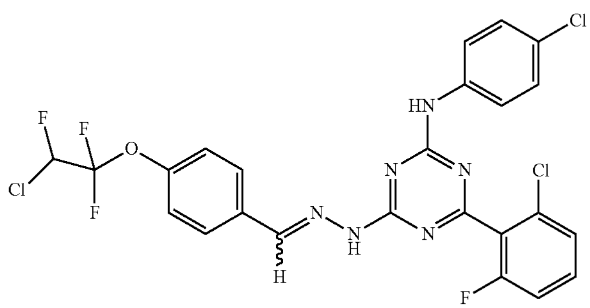 [SMILES: Fc1cccc(Cl)c1-c1nc(NN=Cc2ccc(OC(F)(F)C(F)Cl)cc2)nc(Nc2ccc(Cl)cc2)n1] | White solid | A | 100 | 4-(2-(4-(2-chloro-1,1,2-trifluoroethoxy)benzylidene)hydrazinyl)-6-(2-chloro-6-fluorophenyl)-N-(4-chlorophenyl)-1,3,5-triazin-2-amine |
| 38 | 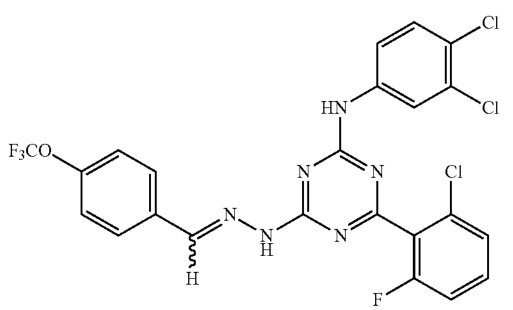 | glass | A | 100 | 4-(2-chloro-6-fluorophenyl)-N-(3,4-dichlorophenyl)-6-(2-(4-(trifluoromethoxy)benzylidene)hydrazinyl)-1,3,5-triazin-2-amine |
| 39 | 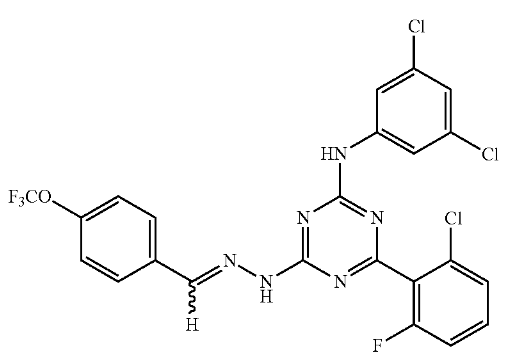 [SMILES: Fc1cccc(Cl)c1-c1nc(NN=Cc2ccc(OC(F)(F)F)cc2)nc(Nc2cc(Cl)cc(Cl)c2)n1] | glass | A | 100 | 4-(2-chloro-6-fluorophenyl)-N-(3,5-dichlorophenyl)-6-(2-(4-(trifluoromethoxy)benzylidene)hydrazinyl)-1,3,5-triazin-2-amine |

TABLE 8-continued

| Ex | Structure | Appearance | Mortality | Conc | name |
|---|---|---|---|---|---|
| 40 | 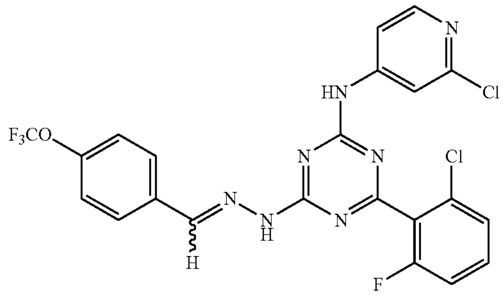 [SMILES: Fc1cccc(Cl)c1-c1nc(NN=Cc2ccc(OC(F)(F)F)cc2)nc(Nc2ccnc(Cl)c2)n1] | White solid | C | 100 | 4-(2-chloro-6-fluorophenyl)-N-(2-chloropyridin-4-yl)-6-(2-(4-(trifluoromethoxy)benzylidene)hydrazinyl)-1,3,5-triazin-2-amine |
| 41 | 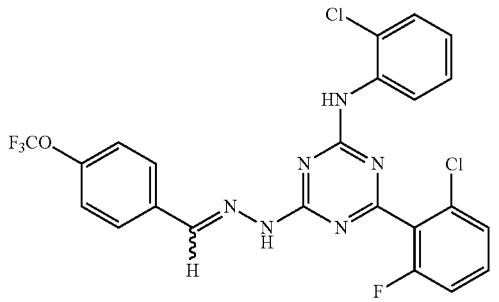 [SMILES: Fc1cccc(Cl)c1-c1nc(NN=Cc2ccc(OC(F)(F)F)cc2)nc(Nc2ccccc2Cl)n1] | film | A | 100 | 4-(2-chloro-6-fluorophenyl)-N-(2-chlorophenyl)-6-(2-(4-(trifluoromethoxy)benzylidene)hydrazinyl)-1,3,5-triazin-2-amine |
| 42 | 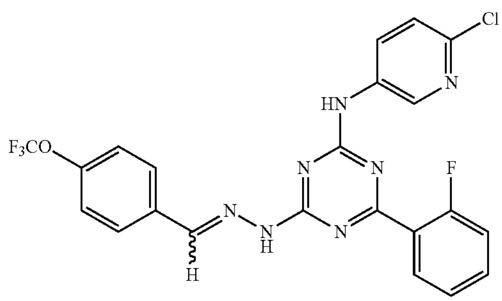 [SMILES: Fc1ccccc1-c1nc(NN=Cc2ccc(OC(F)(F)F)cc2)nc(Nc2ccc(Cl)nc2)n1] | film | A | 100 | N-(6-chloropyridin-3-yl)-4-(2-fluorophenyl)-6-(2-(4-(trifluoromethoxy)benzylidene)hydrazinyl)-1,3,5-triazin-2-amine |
| 43 | 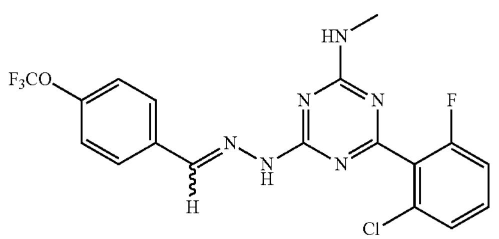 [SMILES: CNc1nc(NN=Cc2ccc(OC(F)(F)F)cc2)nc(-c2c(F)cccc2Cl)n1] | White solid | A | 100 | 4-(2-chloro-6-fluorophenyl)-N-methyl-6-(2-(4-(trifluoromethoxy)benzylidene)hydrazinyl)-1,3,5-triazin-2-amine |
| 44 | 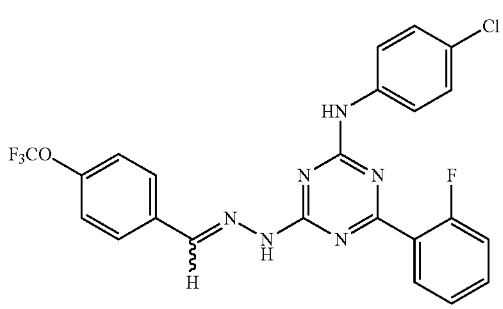 [SMILES: Fc1ccccc1-c1nc(NN=Cc2ccc(OC(F)(F)F)cc2)nc(Nc2ccc(Cl)cc2)n1] | film | A | 100 | N-(4-chlorophenyl)-4-(2-fluorophenyl)-6-(2-(4-(trifluoromethoxy)benzylidene)hydrazinyl)-1,3,5-triazin-2-amine |

TABLE 8-continued

| Ex | Structure | Appearance | Mortality | Conc | name |
|---|---|---|---|---|---|
| 45 | 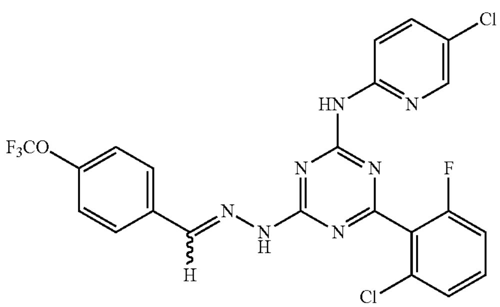 [SMILES: Fc1cccc(Cl)c1-c1nc(NN=Cc2ccc(OC(F)(F)F)cc2)nc(Nc2ccc(Cl)cn2)n1] | Yellow solid | C | 100 | 4-(2-chloro-6-fluorophenyl)-N-(5-chloropyridin-2-yl)-6-(2-(4-(trifluoromethoxy)benzylidene)hydrazinyl)-1,3,5-triazin-2-amine |
| 46 | 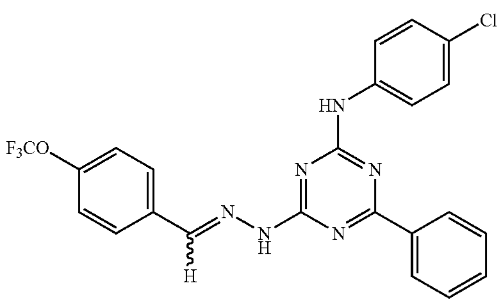 | film | A | 100 | N-(4-chlorophenyl)-2-phenyl-6-(2-(4-(trifluoromethoxy)benzylidene)hydrazinyl)pyrimidin-4-amine |
| 47 | 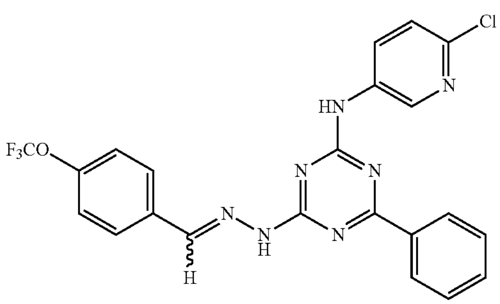 | Off-white solid | D | 100 | N-(6-chloropyridin-3-yl)-6-phenyl-2-(2-(4-(trifluoromethoxy)benzylidene)hydrazinyl)pyrimidin-4-amine |
| 48 | 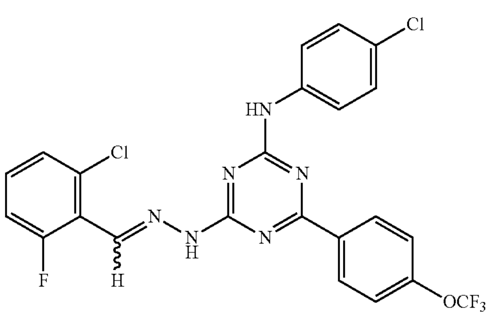 [SMILES: Fc1cccc(Cl)c1C=NNc1nc(Nc2ccc(Cl)cc2)nc(-c2ccc(OC(F)(F)F)cc2)n1] | White solid | A | 100 | 4-(2-(2-chloro-6-fluorobenzylidene)hydrazinyl)-N-(4-chlorophenyl)-6-(4-(trifluoromethoxy)phenyl)-1,3,5-triazin-2-amine |
| 49 | 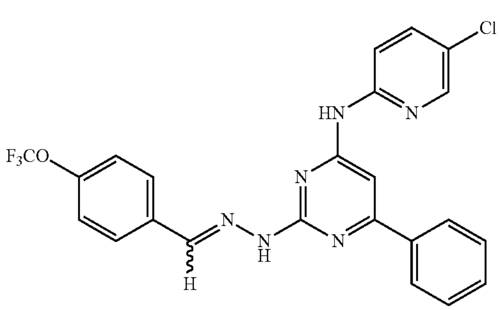 [SMILES: FC(F)(F)Oc1ccc(C=NNc2nc(Nc3ccc(Cl)cn3)cc(-c3ccccc3)n2)cc1] | solid | D | 100 | N-(5-chloropyridin-2-yl)-6-phenyl-2-(2-(4-(trifluoromethoxy)benzylidene)hydrazinyl)pyrimidin-4-amine |

| Ex | Structure | Appearance | Mortality | Conc | name |
|---|---|---|---|---|---|
| 50 | 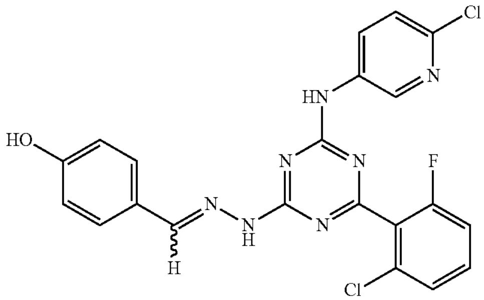 [SMILES: Oc1ccc(C=NNc2nc(Nc3ccc(Cl)nc3)nc(-c3c(F)cccc3Cl)n2)cc1] | White solid | D | 100 | 4-((2-(4-(2-chloro-6-fluorophenyl)-6-((6-chloropyridin-3-yl)amino)-1,3,5-triazin-2-yl)hydrazono)methyl)phenol |
| 51 | 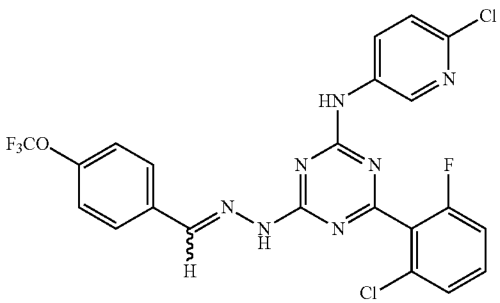 [SMILES: Fc1cccc(Cl)c1-c1nc(NN=Cc2ccc(OC(F)(F)F)cc2)nc(Nc2ccc(Cl)nc2)n1] | film | A | 100 | 4-(2-chloro-6-fluorophenyl)-N-(6-chloropyridin-3-yl)-6-(2-(4-(trifluoromethyl)benzylidene)hydrazinyl)-1,3,5-triazin-2-amine |
| 52 | 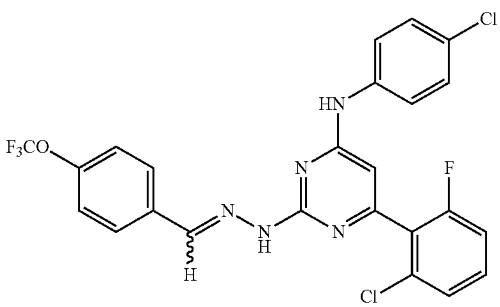 [SMILES: Fc1cccc(Cl)c1-c1cc(Nc2ccc(Cl)cc2)nc(NN=Cc2ccc(OC(F)(F)F)cc2)n1] | glass | A | 100 | 6-(2-chloro-6-fluorophenyl)-N-(4-chlorophenyl)-2-(2-(4-(trifluoromethoxy)benzylidene)hydrazinyl)pyrimidin-4-amine |
| 53 | 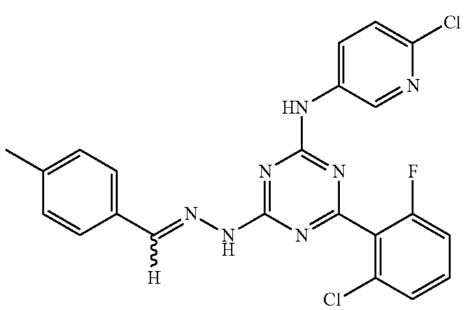 [SMILES: Cc1ccc(C=NNc2nc(Nc3ccc(Cl)nc3)nc(-c3c(F)cccc3Cl)n2)cc1] | film | A | 100 | 4-(2-chloro-6-fluorophenyl)-N-(6-chloropyridin-3-yl)-6-(2-(4-methylbenzylidene)hydrazinyl)-1,3,5-triazin-2-amine |
| 54 | 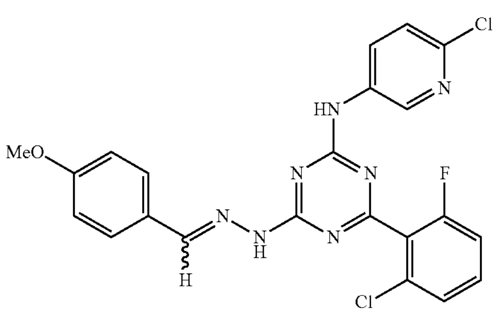 [SMILES: COc1ccc(C=NNc2nc(Nc3ccc(Cl)nc3)nc(-c3c(F)cccc3Cl)n2)cc1] | film | A | 100 | 4-(2-chloro-6-fluorophenyl)-N-(6-chloropyridin-3-yl)-6-(2-(4-methoxybenzylidene)hydrazinyl)-1,3,5-triazin-2-amine |

TABLE 8-continued

| Ex | Structure | Appearance | Mortality | Conc | name |
|----|-----------|------------|-----------|------|------|
| 55 | 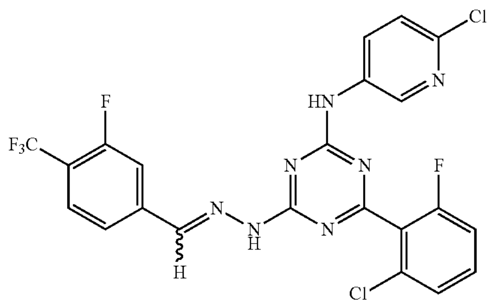 [SMILES: Fc1cc(C=NNc2nc(Nc3ccc(Cl)nc3)nc(-c3c(F)cccc3Cl)n2)ccc1C(F)(F)F] | film | A | 100 | 4-(2-chloro-6-fluorophenyl)-N-(6-chloropyridin-3-yl)-6-(2-(3-fluoro-4-(trifluoromethyl)benzylidene)hydrazinyl)-1,3,5-triazin-2-amine |
| 56 | 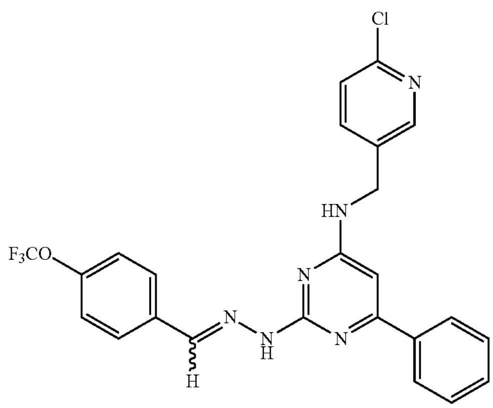 | film | A | 100 | N-((6-chloropyridin-3-yl)methyl)-6-phenyl-2-(2-(4-(trifluoromethoxy)benzylidene)hydrazinyl)pyrimidin-4-amine |
| 57 | 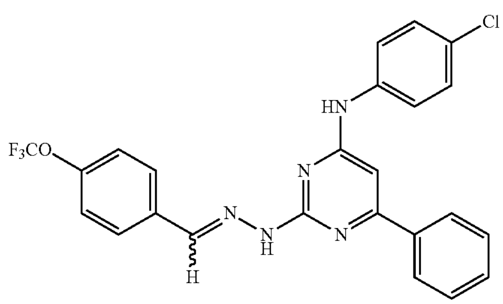 [SMILES: FC(F)(F)Oc1ccc(C=NNc2nc(Nc3ccc(Cl)cc3)cc(-c3ccccc3)n2)cc1] | solid | A | 100 | N-(4-chlorophenyl)-6-phenyl-2-(2-(4-(trifluoromethoxy)benzylidene)hydrazinyl)pyrimidin-4-amine |
| 58 | 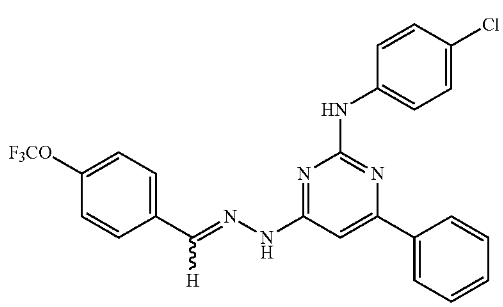 [SMILES: FC(F)(F)Oc1ccc(C=NNc2cc(-c3ccccc3)nc(Nc3ccc(Cl)cc3)n2)cc1] | Solid | A | 100 | N-(4-chlorophenyl)-4-phenyl-6-(2-(4-(trifluoromethoxy)benzylidene)hydrazinyl)pyrimidin-2-amine |
| 59 | 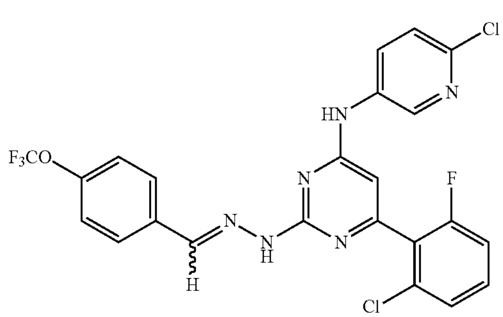 | Solid | A | 100 | 6-(2-chloro-6-fluorophenyl)-N-(6-chloropyridin-3-yl)-2-(2-(4-(trifluoromethoxy)benzylidene)hydrazinyl)pyrimidin-4-amine |

TABLE 8-continued

| Ex | Structure | Appearance | Mortality | Conc | name |
|---|---|---|---|---|---|
| 60 | 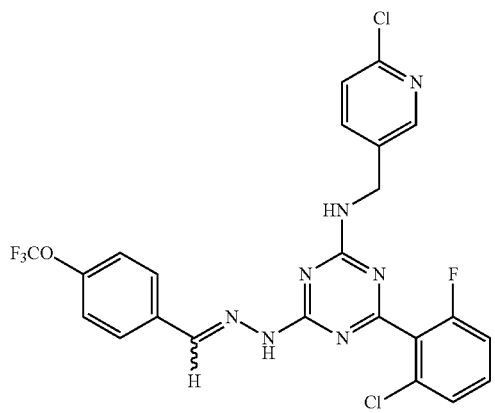 [SMILES: Fc1cccc(Cl)c1-c1nc(NCc2ccc(Cl)nc2)nc(NN=Cc2ccc(OC(F)(F)F)cc2)n1] | glass | A | 100 | 4-(2-chloro-6-fluorophenyl)-N-(4-chlorobenzyl)-6-(2-(4-(trifluoromethoxy)benzylidene)hydrazinyl)-1,3,5-triazin-2-amine |
| 61 | 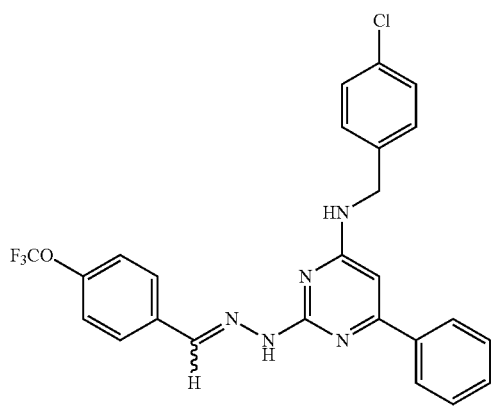 [SMILES: FC(F)(F)Oc1ccc(C=NNc2nc(NCc3ccc(Cl)cc3)cc(-c3ccccc3)n2)cc1] | film | A | 100 | N-(4-chlorobenzyl)-6-phenyl-2-(2-(4-(trifluoromethoxy)benzylidene)hydrazinyl)pyrimidin-4-amine |

Insecticidal Utility

The compounds of the invention are useful for the control of invertebrates including insects. Therefore, the present invention also is directed to a method for inhibiting an insect which comprises applying an insect-inhibiting amount of a compound of Formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 3500 ppm by weight active compound is used.

For example, insects or other pests which can be inhibited include

Most preferred Lepidoptera—*Heliothis* spp., *Helicoverpa* spp., *Spodoptera* spp., *Mythimna unipuncta, Agrotis ipsilon, Earias* spp., *Euxoa auxiliaris, Trichoplusia ni, Anticarsia gemmatalis, Rachiplusia nu, Plutella xylostella, Chilo* spp., *Scirpophaga incertulas, Sesamia inferens, Cnaphalocrocis*

*medinalis, Ostrinia nubilalis, Cydia pomonella, Carposina niponensis, Adoxophyes orana, Archips argyrospilus, Pandemis heparana, Epinotia aporema, Eupoecilia ambiguella, Lobesia botrana, Polychrosis viteana, Pectinophora gossypiella, Pieris rapae, Phyllonorycter* spp., *Leucoptera malifoliella, Phyllocnisitis citrell.*

Coleoptera—*Diabrotica* spp., *Leptinotarsa decemlineata, Oulema oryzae, Anthonomus grandis, Lissorhoptrus oryzophilus, Agriotes* spp., *Melanotus communis, Popillia japonica, Cyclocephala* spp., *Tribolium* spp.

Diptera—*Liriomyza* spp., *Musca domestica, Aedes* spp., *Culex* spp., *Anopheles* spp., *Fannia* spp., *Stomoxys* spp., *Mayetiola destructor.*

Blattidea (cockroaches)—*Blatta orientalis, Blattella germanica, Periplaneta americana, Supella longipalpa, Periplaneta australasiae, Periplaneta brunnea, Parcoblatta pennsylvanica, Periplaneta fuliginosa, Pycnoscelus surinamensis.*

Preferred: Hymenoptera—*Iridomyrmex humilis, Solenopsis* spp., *Monomorium pharaonis, Atta* spp., *Pogonomyrmex* spp., *Camponotus* spp., *Monomorium* spp., *Tapinoma sessile, Tetramorium* spp., *Xylocapa* spp., *Vespula* spp., *Polistes* spp.

Isoptera—*Reticulitermes flavipes, Coptotermes formosanus, Reticulitermes virginicus, Heterotermes aureus, Reticulitermes hesperus, Coptotermes frenchii, Shedorhinotermes* spp., *Reticulitermes santonensis, Reticulitermes grassei, Reticulitermes banyulensis, Reticulitermes speratus, Reticulitermes hageni, Reticulitermes tibialis, Zootermopsis* spp., *Incisitermes* spp., *Marginitermes* spp., *Macrotermes* spp., *Microcerotermes* spp., *Microtermes* spp.

Orthoptera (grasshoppers, crickets)—*Melanoplus* spp., *Locusta migratoria, Schistocerca gregaria, Gryllotalpidae* (mole crickets).

Also Identified: Homoptera—*Aphis* spp., *Myzus persicae, Rhopalosiphum* spp., *Dysaphis plantaginea, Toxoptera* spp., *Macrosiphum euphorbiae, Aulacorthum solani, Sitobion avenae, Metopolophium dirhodum, Schizaphis graminum, Brachycolus noxius, Nephotettix* spp., *Nilaparvata lugens, Sogatella furcifera, Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*

Hemiptera—*Lygus* spp., *Eurygaster maura, Nezara viridula, Piezodorus guildingi, Leptocorisa varicomis, Cimex lectularius, Cimex hemipterus*

Thysanoptera—*Frankliniella* spp., *Thrips* spp., *Scirtothrips dorsalis*

Mallophaga (chewing lice)

Anoplura (sucking lice)—*Pthirus pubis, Pediculus* spp.

Siphonaptera—*Ctenophalides* spp., *Pulex irritans*

Acari—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.

Nematoda—*Dirofilaria immitis, Meloidogyne* spp., *Heterodera* spp., *Hoplolaimus columbus, Belonolaimus* spp., *Pratylenchus* spp., *Rotylenchus reniformis, Criconemella ornata, Ditylenchus* spp., *Aphelenchoides besseyi, Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid Formulations which are dispersed in water for application, or are dust or granular Formulations which are applied without further treatment. The compositions are prepared according to procedures and Formulae which are conventional in the agricultural chemical art, but which are novel and important because of the presence therein of the compounds of this invention. Some description of the Formulation of the compositions will be given, however, to assure that agricultural chemists can readily prepare any desired composition.

The dispersions in which the compounds are applied are most often aqueous suspensions or emulsions prepared from concentrated Formulations of the compounds. Such water-soluble, water-suspendable or emulsifiable Formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be Formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microexcapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be Formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae*, *B. sphaericus*, *B. thuringiensis* subsp. *aizawai*, *B. thuringiensis* subsp. *kurstaki*, *B. thuringiensis* subsp. *tenebrionis*, *Beauveria bassiana*, *Cydia pomonella* granulosis virus, Douglas fir tussock moth NPV, gypsy moth NPV, *Helicoverpa zea* NPV, Indian meal moth granulosis virus, *Metarhizium anisopliae*, *Nosema locustae*, *Paecilomyces fumosoroseus*, *P. lilacinus*, *Photorhabdus luminescens*, *Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as .alpha.-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AICD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminum, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, *Reynoutria sachalinensis* extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:
1. A method of using a compound of Formula (I),

Formula I

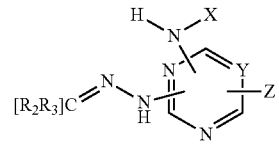

wherein:

Y is CR$_1$;

R$_1$ is —H, Halo or —C$_1$-C$_4$ alkyl;

Z is -aryl, —C$_1$-C$_8$ alkylaryl, —C$_3$-C$_8$ cycloalkyl, —C$_1$-C$_6$ alkylC$_6$cycloalkyl, heterocyclic, —C$_1$-C$_8$ alkylheterocyclic, X, is —H, —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, heterocyclic, —C$_1$-C$_8$ alkylheterocyclic, —NR$^i$R$^j$ or —C$_1$-C$_8$ alkylNR$^i$R$^j$;

R$_2$ and R$_3$ are independently —H or —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, heterocyclic, —C$_1$-C$_8$ alkylheterocyclic, and —C$_1$-C$_8$ alkylNR$^i$R$^j$, but R$_2$ and R$_3$ are not both H;

R$^i$ and R$^j$ are independently —H, or —C$_1$-C$_8$ alkyl;

wherein heterocyclic is a 5-10 member cyclic or bicyclic aromatic or saturated —C$_1$-C$_8$ cycloaliphatic ring moiety containing 1, 2, or 3 heteroatoms selected from N, O, or S;

wherein aryl, —C$_3$-C$_8$ cycloalkyl and heterocyclic are optionally independently substituted with one to five substituents independently selected from -halo, —CN, —OH, —OCH$_2$CH═CHCl, —C$_1$-C$_6$ alkyl, —O—C$_1$-C$_6$ alkyl, or —S—C$_1$-C$_6$ alkyl; and at each occurrence alkyl, is optionally substituted with 1-5 halo, —CN, or —OH in order to control and inhibit: insects, mites and nematodes, comprising applying an insect-inhibiting amount of a compound of Formula I to the locus, area to be protected or directly on the insects, mites and nematodes.

2. A method of claim 1 wherein halo is Cl or F;

$R^i$ and $R^j$ are H or $C_1$-$C_2$ alkyl; and $R_2$ and $R_3$ are independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkyl$NR^iR^j$; but when one of $R_2$ and $R_3$ are -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkyl$NR^iR^j$ then the other of either $R_2$ or $R_3$ is independently —H or —$C_1$-$C_8$ alkyl.

3. A method of claim 1 wherein

X, Z, $R_2$, and $R_3$ are independently a —$C_1$-$C_6$ cycloalkyl, —$C_1$-$C_6$ alkyl$C_6$cycloalkyl, —$C_6$ aryl, —$C_1$-$C_6$alkyl$C_6$ aryl or $C_6$ heterocyclic or —$C_1$-$C_6$ alkyl$C_6$-heterocyclic or saturated or unsaturated optionally substituted ring, wherein X, Z, $R_2$, and $R_3$ are optionally independently substituted with 1, 2 or 3, of —H, -halo, —CN, —OH, —OCH$_2$CH=CHCl, —$C_1$-$C_6$ alkyl, —O—$C_1$-$C_6$ alkyl, or —S—$C_1$-$C_6$ alkyl;

wherein at each occurrence, any —$C_1$-$C_6$ alkyl, is optionally independently substituted with 1-5-halo, —CN or —OH.

4. A method of claim 3 wherein

X, Z, and $R_2$, and $R_3$ are independently a heterocyclic or —$C_1$-$C_6$ alkylheterocyclic 6 member saturated or unsaturated optionally substituted ring, wherein X, Z, and $R_2$, or $R_3$ is optionally independently substituted with 1 or 2 —H, -halo, —CN, —OH, —OCH$_2$CH=CHCl, —$C_1$-$C_6$ alkyl, —O—$C_1$-$C_6$ alkyl, or —S—$C_1$-$C_6$ alkyl;

wherein at each occurrence, any —$C_1$-$C_6$ alkyl, is optionally independently substituted with 1-5-halo, —CN or —OH.

5. A method of claim 4 wherein

X, Z, $R_2$, and $R_3$ are independently a heterocyclic or —$C_1$-$C_6$ alkylheterocyclic 6 member saturated or unsaturated optionally substituted ring, wherein X, Z, and $R_2$, or $R_3$ is optionally independently substituted with 1 —H, -halo, —CN, —OH, —OCH$_2$CH=CHCl, —$C_1$-$C_6$ alkyl, —O—$C_1$-$C_6$ alkyl, or —S—$C_1$-$C_6$ alkyl;

wherein at each occurrence, any —$C_1$-$C_6$ alkyl, is optionally independently substituted with 1-5-halo, —CN or —OH.

6. A method of claim 3 wherein said heterocyclic or alkylheterocyclic is an aromatic unsaturated optionally substituted ring, a aliphatic saturated ring, or a combination of both unsaturated and saturated optionally substituted rings and the hetero atom is a non adjacent N or O or combination of N and O atoms.

7. A method of claim 3 wherein

Z is -aryl, —$C_1$-$C_8$ alkylaryl, —$C_3$-$C_8$ cycloalkyl, or —$C_1$-$C_6$ alkyl$C_6$cycloalkyl;

X is —H, —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, —$NR^iR^j$ or —$C_1$-$C_8$ alkyl$NR^iR^j$;

when $R_2$ is —H or —$C_1$-$C_8$ alkyl then $R_3$ is —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, and —$C_1$-$C_8$ alkyl$NR^iR^j$; and when $R_3$ is —H or —$C_1$-$C_8$ alkyl then $R_2$ is —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, and —$C_1$-$C_8$ alkyl$NR^iR^j$;

$R^i$ and $R^j$ are independently —H, or —$C_1$-$C_8$ alkyl.

8. A method of claim 7 wherein aryl is phenyl, alkylaryl is alkylphenyl and phenyl or alkylphenyl is optionally independently substituted with 1, 2 or 3-halo, —CN, —OH, —OCH$_2$CH=CHCl, —$C_1$-$C_6$ alkyl, —O—$C_1$-$C_6$ alkyl, or —S—$C_1$-$C_6$ alkyl;

and at each occurrence alkyl, is optionally substituted with 1-5 halo, —CN, or —OH.

9. A method of claim 8 wherein

X is optionally independently substituted with 1, 2 or 3-halo, —CN, —OH, —OCH$_2$CH=CHCl, —$C_1$-$C_6$ alkyl, —O—$C_1$-$C_6$ alkyl, or —S—$C_1$-$C_6$ alkyl;

$R_2$ or $R_3$ is optionally independently substituted with 1 or 2-halo, —CN, —OH, —OCH$_2$CH=CHCl, —$C_1$-$C_6$ alkyl, —O—$C_1$-$C_6$ alkyl, or —S—$C_1$-$C_6$ alkyl;

Z is optionally independently substituted with 1, 2 or 3-halo, —CN, —OH, —OCH$_2$CH=CHCl, —$C_1$-$C_6$ alkyl, —O—$C_1$-$C_6$ alkyl, or —S—$C_1$-$C_6$ alkyl;

and at each occurrence alkyl, is optionally substituted with 1-5 halo, —CN, or —OH.

10. A method of claim 1 wherein the aryl is phenyl and phenyl is optionally substituted with 1-3 $R_{10}$, at any of the positions of any of the formula below; and $R_{10}$ is optionally independently substituted with one to five substituents independently selected from -halo, —CN, —OH, —OCH$_2$CH=CHCl, —$C_1$-$C_6$ alkyl, —O—$C_1$-$C_6$ alkyl, or —S—$C_1$-$C_6$ alkyl; and at each occurrence alkyl, is optionally substituted with 1-5 halo, —CN, or —OH;

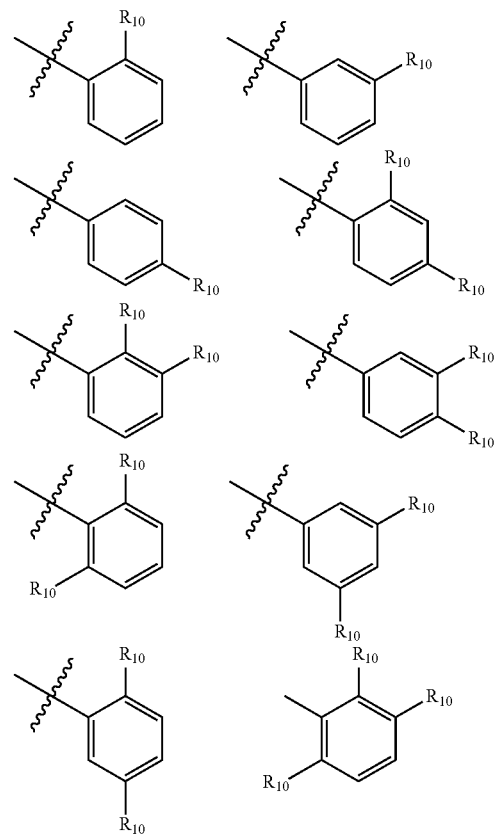

-continued

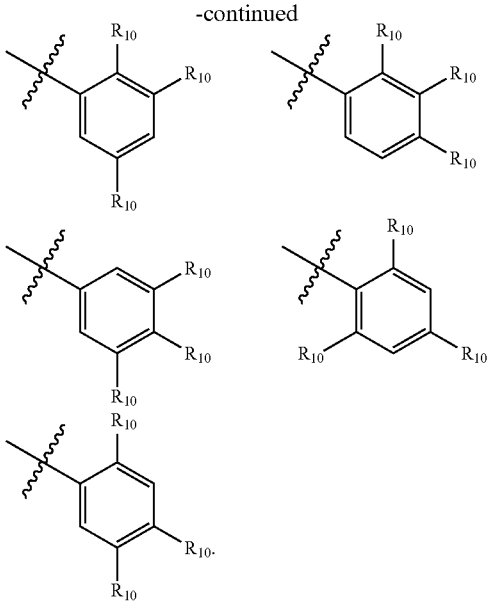

11. A method of claim 1 wherein

X, Z, R$_2$, and R$_3$ are independently a heterocyclic or alkylheterocyclic 5, 6 or 10 member saturated or unsaturated optionally substituted ring, optionally independently substituted with 1, 2 or 3, of —H, -halo, —CN, —OH, —OCH$_2$CH=CHCl, —C$_1$-C$_6$ alkyl, —O—C$_1$-C$_6$ alkyl, or —S—C$_1$-C$_6$ alkyl;

wherein at each occurrence, any —C$_1$-C$_6$ alkyl, is optionally independently substituted with 1-5-halo, —CN or —OH.

12. A method of claim 11 wherein

Z is -aryl, —C$_1$-C$_8$ alkylaryl, —C$_3$-C$_8$ cycloalkyl, or —C$_1$-C$_6$alkylC$_6$cycloalkyl;

X is heterocyclic or —C$_1$-C$_8$ alkylheterocyclic;

when R$_2$ is —H or —C$_1$-C$_8$ alkyl, then R$_3$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$;

when R$_3$ is —H or —C$_1$-C$_8$ alkyl, then R$_2$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$.

13. A method of claim 11 wherein

Z is heterocyclic or —C$_1$-C$_8$ alkylheterocyclic,

X is —H, —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, —NR$^i$R$^j$ or —C$_1$-C$_8$ alkylNR$^i$R$^j$;

when R$_2$ is —H or —C$_1$-C$_8$ alkyl, then R$_3$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$; and when R$_3$ is —H or —C$_1$-C$_8$ alkyl, then R$_2$ is —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl and —C$_1$-C$_8$ alkylNR$^i$R$^j$.

14. A method of claim 11 wherein

Z is -aryl, —C$_1$-C$_8$ alkylaryl, —C$_3$-C$_8$ cycloalkyl, or —C$_1$-C$_6$alkylC$_6$cycloalkyl;

X is —H, —C$_1$-C$_8$ alkyl, -aryl, —C$_1$-C$_8$ alkylaryl, —C$_3$-C$_8$ cycloalkyl, —C$_1$-C$_8$ alkylC$_3$-C$_8$ cycloalkyl, —NR$^i$R$^j$ or —C$_1$-C$_8$ alkylNR$^i$R$^j$;

R$_2$ is —H or —C$_1$-C$_8$ alkyl, when R$_3$ is heterocyclic and —C$_1$-C$_8$ alkylheterocyclic;

R$_3$ is —H or —C$_1$-C$_8$ alkyl, when R$_2$ is -heterocyclic and —C$_1$-C$_8$ alkylheterocyclic.

15. A method of claim 1 wherein Formula I is selected from Formulas II-CR1, III-CR1, and IV-CR1, Formula II-CR1

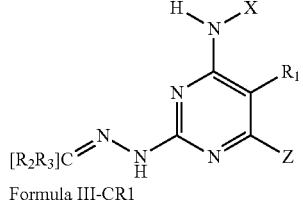

Formula III-CR1

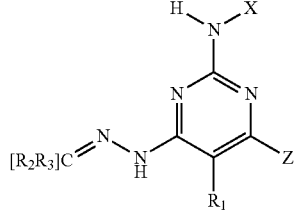

Formula IV-CR1

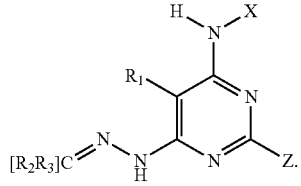

16. A method of claim 15 wherein R$_1$ is —H, —F or —CF$_3$.

17. A method of claim 1 wherein the compounds are selected from

Formula II-CR1

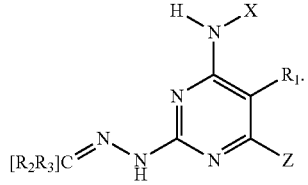

18. A method of claim 1 wherein

X, Z, R$_2$, and R$_3$ are independently a —C$_1$-C$_6$ cycloalkyl, —C$_1$-C$_6$ alkylC$_6$cycloalkyl, C$_6$ aryl, —C$_1$-C$_6$alkylC$_6$ aryl or C$_6$ heterocyclic or —C$_1$-C$_6$ alkylC$_6$-heterocyclic or saturated or unsaturated optionally substituted ring, wherein X, Z, and either R$_2$, or R$_3$ is optionally independently substituted with 1, 2 or 3, of —H, -halo, —CN, —OH, —OCH$_2$CH=CHCl, —C$_1$-C$_6$ alkyl, —O—C$_1$-C$_6$ alkyl, or —S—C$_1$-C$_6$ alkyl;

wherein at each occurrence, any —C$_1$-C$_6$ alkyl, is optionally independently substituted with 1-5-halo, —CN or —OH.

19. The method of claim 1 using a compound selected from:

N-(4-chlorophenyl)-2-phenyl-6-(2-(4-(trifluoromethoxy)benzylidene)hydrazinyl)pyrimidin-4-amine;

6-(2-chloro-6-fluorophenyl)-N-(4-chlorophenyl)-2-(2-(4-(trifluoromethoxy)benzylidene)hydrazinyl)pyrimidin-4-amine;

N-((6-chloropyridin-3-yl)methyl)-6-phenyl-2-(2-(4-(trifluoromethoxy)benzylidene)hydrazinyl)pyrimidin-4-amine;

N-(4-chlorophenyl)-6-phenyl-2-(2-(4-(trifluoromethoxy)benzylidene)hydrazinyl)pyrimidin-4-amine; N-(4-chlorophenyl)-4-phenyl-6-(2-(4-(trifluoromethoxy)benzylidene)hydrazinyl)pyrimidin-2-amine;

6-(2-chloro-6-fluorophenyl)-N-(6-chloropyridin-3-yl)-2-(2-(4-(trifluoromethoxy)benzylidene)hydrazinyl)pyrimidin-4-amine; and N-(4-chlorobenzyl)-6-phenyl-2-(2-(4-(trifluoromethoxy)benzylidene)hydrazinyl)pyrimidin-4-amine.

20. An insecticidal composition, with an optional phytologically-acceptable carrier comprising the compounds of Formula I, useful for the control of insects, mites and nematodes, where Formula I is:

Formula I

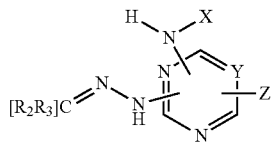

wherein:

Y is N;

$R_1$ is —H, Halo or —$C_1$-$C_4$ alkyl;

Z is -aryl, —$C_1$-$C_8$ alkylaryl, —$C_3$-$C_8$ cycloalkyl, —$C_1$-$C_6$ alkyl$C_6$cycloalkyl, heterocyclic, —$C_1$-$C_8$ alkylheterocyclic, X, is —H, —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, —NR$^i$R$^j$ or —$C_1$-$C_8$ alkylNR$^i$R$^j$;

$R_2$ and $R_3$ are independently —H or —$C_1$-$C_8$ alkyl, -aryl, —$C_1$-$C_8$ alkylaryl, —$C_3$-$C_8$ cycloalkyl, —$C_1$-$C_8$ alkyl$C_3$-$C_8$ cycloalkyl, heterocyclic, —$C_1$-$C_8$ alkylheterocyclic, and —$C_1$-$C_8$ alkylNR$^i$R$^j$, but $R_2$ and $R_3$ are not both H;

R$^i$ and R$^j$ are independently —H, or —$C_1$-$C_8$ alkyl;

wherein heterocyclic is a 5-10 member cyclic or bicyclic aromatic or saturated —$C_1$-$C_8$ cycloaliphatic ring moiety containing 1, 2, or 3 heteroatoms selected from N, O, or S;

wherein aryl, —$C_3$-$C_8$ cycloalkyl and heterocyclic are optionally independently substituted with one to five substituents independently selected from -halo, —CN, —OH, —OCH$_2$CH=CHCl, —$C_1$-$C_6$ alkyl, —O—$C_1$-$C_6$ alkyl, or —S—$C_1$-$C_6$ alkyl; and at each occurrence, alkyl is optionally substituted with 1-5 halo, —CN, or —OH.

21. The composition of claim 20 applied in the form of a spray, topical treatment, gel, seed coating, microcapsulation, bait, ear tag, bolus, fogger, aerosol or dust to the locus of an insect.

22. The composition of claim 20 where the insecticidal composition is in the form of water soluble, water-suspendable or emulsifiable formulation a wettable dry powder or a liquid in the form of an emulsifiable concentrate or aqueous suspension.

23. The composition of claim 20 wherein the concentration of the active compound is from about 10% to about 90% by weight.

24. An insecticidal composition of claim 20 wherein Formula I is combined with one or more insecticides fungicides or herbicides in order to control undesired pests.

* * * * *

UNITED STATES PATENT AND TRADEMARK OFFICE
CERTIFICATE OF CORRECTION

| | | |
|---|---|---|
| PATENT NO. | : 8,785,630 B2 | Page 1 of 1 |
| APPLICATION NO. | : 13/760925 | |
| DATED | : July 22, 2014 | |
| INVENTOR(S) | : Robert M. Kennedy et al. | |

It is certified that error appears in the above-identified patent and that said Letters Patent is hereby corrected as shown below:

In the Claims

In column 164, line 35, claim 16, after "–H," insert -- –Cl, --.

In column 166, line 27, claim 22, after "formulation" insert -- such as --.

Signed and Sealed this
Twenty-first Day of July, 2015

Michelle K. Lee
*Director of the United States Patent and Trademark Office*